(12) United States Patent
Denomme et al.

(10) Patent No.: US 11,598,771 B2
(45) Date of Patent: Mar. 7, 2023

(54) SELF-REFERENCING SENSOR FOR CHEMICAL DETECTION

(71) Applicant: Nicoya Lifesciences, Inc., Kitchener (CA)

(72) Inventors: Ryan Cameron Denomme, Kitchener (CA); John Alexander Gordon Dick, Kitchener (CA); Sarah Ann Leblanc, Waterloo (CA)

(73) Assignee: Nicoya Lifesciences, Inc., Kitchener (CA)

( * ) Notice: Subject to any disclaimer, the term of this patent is extended or adjusted under 35 U.S.C. 154(b) by 332 days.

(21) Appl. No.: 17/063,424

(22) Filed: Oct. 5, 2020

(65) Prior Publication Data
US 2021/0132055 A1 May 6, 2021

Related U.S. Application Data

(63) Continuation of application No. 15/134,843, filed on Apr. 21, 2016, now Pat. No. 10,794,904, which is a continuation-in-part of application No. 14/216,042, filed on Mar. 17, 2014, now Pat. No. 9,322,823.

(60) Provisional application No. 61/798,450, filed on Mar. 15, 2013.

(51) Int. Cl.
*G01N 33/543* (2006.01)
*G01N 21/552* (2014.01)

(52) U.S. Cl.
CPC ..... *G01N 33/54373* (2013.01); *G01N 21/554* (2013.01); *G01N 33/54346* (2013.01)

(58) Field of Classification Search
CPC .......... G01N 33/54373; G01N 21/554; G01N 33/54346
See application file for complete search history.

(56) References Cited

U.S. PATENT DOCUMENTS

| 7,079,250 B2 | 7/2006 | Mukai |
| 8,085,405 B2 | 12/2011 | Ogawa |
| 9,322,823 B2 * | 4/2016 | Denomme ........... G01N 21/554 |

(Continued)

FOREIGN PATENT DOCUMENTS

WO    WO 2013/048328 A1 * 9/2012

OTHER PUBLICATIONS

Dotzauer et al ., "Catalytic Membranes Prepared Using Layer—by Layer Absorption of Polyelectrolyte / Metal Nanoparticle Films in PorousSupports", Nano Letters , Vo . 6 , No. 10 , 2006 , pp. 2268 2272.

(Continued)

*Primary Examiner* — Brian J. Sines
(74) *Attorney, Agent, or Firm* — Wilson Sonsini Goodrich & Rosati

(57) ABSTRACT

Provided herein is a sensing apparatus comprising, at least one LSPR light source, at least one detector, and at least one sensor for LSPR detection of a target chemical. The sensor comprises a substantially transparent, porous membrane having nanoparticles immobilized on the surface of its pores, the nanoparticles being functionalized with one or more capture molecules. There is further provided a self-referencing sensor for distinguishing non-specific signals from analyte binding signals. The self-referencing sensor comprising one or more nanoparticles having at least two distinct LSPR signals.

19 Claims, 43 Drawing Sheets

(56) References Cited

U.S. PATENT DOCUMENTS

| | | |
|---|---|---|
| 10,324,034 B2* | 6/2019 | Chau .................... G01N 21/554 |
| 10,794,904 B2* | 10/2020 | Denomme ........... G01N 21/554 |
| 2002/0142480 A1 | 10/2002 | Natan |
| 2006/0194346 A1 | 8/2006 | Knoll et al. |
| 2007/0248987 A1 | 10/2007 | Imamura et al. |
| 2008/0096289 A1 | 4/2008 | Zhou et al. |
| 2008/0117423 A1 | 5/2008 | Ogawa et al. |
| 2008/0173093 A1 | 7/2008 | Wang et al. |
| 2008/0213814 A1 | 9/2008 | Gerion et al. |
| 2009/0009756 A1 | 1/2009 | Yamamichi et al. |
| 2009/0041404 A1 | 2/2009 | Stoddart |
| 2009/0169797 A1 | 7/2009 | Hayes et al. |
| 2009/0213368 A1 | 8/2009 | Roper et al. |
| 2009/0310140 A1 | 12/2009 | Smith et al. |
| 2009/0310902 A1 | 12/2009 | Smith et al. |
| 2009/0325211 A1 | 12/2009 | Fang et al. |
| 2011/0171749 A1 | 7/2011 | Alocilja et al. |
| 2012/0145532 A1 | 6/2012 | Smolyakov et al. |
| 2012/0184451 A1 | 7/2012 | Singamaneni et al. |
| 2012/0208174 A1 | 8/2012 | Galush et al. |
| 2013/0052638 A1 | 2/2013 | Tan et al. |
| 2013/0135617 A1 | 5/2013 | Pris et al. |
| 2013/0217598 A1 | 8/2013 | Ludwig et al. |
| 2014/0004528 A1 | 1/2014 | Albuquerque De Farias et al. |
| 2014/0135617 A1 | 5/2014 | Schoepp |
| 2014/0160218 A1 | 6/2014 | Tajima et al. |
| 2014/0249055 A1 | 9/2014 | Yamada et al. |
| 2014/0271366 A1 | 9/2014 | Denomme et al. |
| 2014/0308756 A1 | 10/2014 | Gautier et al. |
| 2015/0160218 A1 | 6/2015 | Demirci et al. |
| 2015/0293084 A1 | 10/2015 | Del Pino González De La Higuera et al. |
| 2015/0293088 A1 | 10/2015 | Mehra et al. |

OTHER PUBLICATIONS

Eftekhari et al., Nanoholes as Nanochannels Flow—through Plasmonic Sensing, Analytical Chemistry, vol. 81, No. 11, Jun. 1, 2009, pp. 4308-4311.

Govyadinov et al., ** Anodic Aluminum Oxide Microchannel Plates, Nuclear Instruments and Methods in Physics Research, vol. 419, 1996, pp. 667-675.

Shag et al., "Optical Fiber LSPR Biosensor Prepared by Gold Nanoparticle Assembly on Polyelectrolyte Multilayer, Sensors, Vo. 10, 2010, pp. 3585-3596."

Poinem et al., "Nano—hardness and elastic modulus of anodic aluminum oxide based Poly (2-hydroxyethylmethacrylate) composite membranes", AIMS Materials Science, Aug. 20, 2014, vol. 1, Issue 3, pp. 159-173.

Romero et al., "Effect of Porosity and Concentration Polarization on Electrolyte Diffusive Transport Parameters through Ceramic Membranes with Similar Nanopore Size", Nanomaterials 2014, vol. 4, pp. 700-711.

* cited by examiner

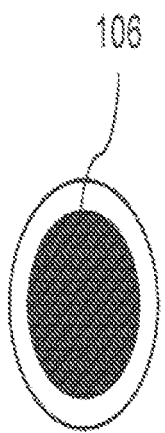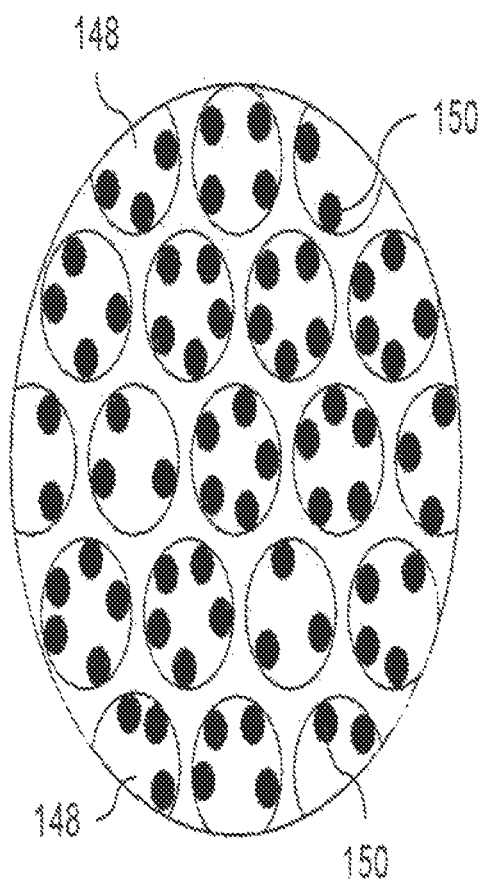
FIG. 4A
FIG. 4B

SELF-REFERENCING SENSOR FOR CHEMICAL DETECTION

CROSS REFERENCE TO PRIOR APPLICATIONS

The present application is a continuation application of U.S. application Ser. No. 15/134,843, filed on Apr. 21, 2016, which is a Continuation in Part Application of U.S. application Ser. No. 14/216,042 which claims priority under Paris Convention to U.S. application Ser. No. 61/798,450, filed Mar. 15, 2013, the entire contents of which are incorporated herein by reference.

TECHNICAL FIELD

The following relates generally to a method and apparatus for chemical detection. More particularly it relates to a self-referencing sensor and an apparatus comprising the sensor.

BACKGROUND

Determining the presence and concentration of bio-molecules and other chemicals in a fluid is important in many applications. For example, an instrument that can determine the concentration of one or more specific chemical targets in a gas or liquid containing various chemicals may have applications in medical diagnostics, high throughput drug development, environmental testing, defense and laboratory-based research. Such techniques are also important for biomolecular interaction analysis in which reaction kinetics (on and off rates), affinity, and specificity are determined, along with other important parameters.

A common strategy to detect a chemical target is to use an instrument with a capture molecule which binds to the target chemical of interest and a transducer that allows the user to observe the binding event. Preferably, the capture molecule preferentially or exclusively binds to the chemical target. In the case of bio-molecular targets, antibodies, aptamers and polymers are used as capture molecules.

Optical transduction of binding events is a common detection method. To optically observe a binding event between a capture molecule and a target, various spectrometric techniques can be employed. These techniques may require that capture molecules be labeled with a transducer or tag, such as a fluorescent molecule for fluorescence spectroscopy or a Raman tag for Raman spectroscopy. A technique used for medical diagnostics is enzyme linked immunosorbant assay (ELISA) that utilizes fluorescently-labeled antibodies to detect various target chemicals, including bio-molecules, in human biological fluids to detect disease.

Labeled assays may be disadvantageous because labeled capture molecules may have adverse effects on assay results due to steric hindrances. Assays comprising labeled capture molecules are also not compatible with real-time testing. Labeling capture molecules also increases device complexity and cost.

Label-free assays, which do not require the addition of a labeled capture molecule, are advantageous because the target chemical is not sterically hindered from binding to the capture molecule by a label. Label-free assays may also measure binding events in real time, which improves the performance and sensitivity of the assay. Label-free assays can also be used for biomolecular interaction analysis as they provide real time data.

Metal nanoparticles, between 1 nm and 1000 nm in various dimensions, may be used as transducers in diagnostic assays. Some nanoparticle based diagnostic assays are 'label-free'. Metal nanoparticle transducers can be used to monitor binding events in real time without additional labels through a phenomenon known as localized surface plasmon resonance (LSPR).

LSPR is a phenomenon associated with noble metal nanoparticles that creates sharp spectral absorbance and scattering peaks and produces strong electromagnetic near-field enhancements. These spectral peaks can be monitored using absorbance spectroscopy. The spectral peak changes with refractive index changes in the immediate vicinity of the nanoparticle surface. When chemical targets are bound near the surface of a metal nanoparticle, a shift in the spectral peak occurs due to changes in the local refractive index. This can be used to determine the concentration of a specific target in a complex medium.

LSPR sensors operate through the immobilization of metal nanoparticles onto a flat surface. The nanoparticles are functionalized with specific capture molecules, which may be an antibody. The sample fluid of interest is flowed over the top of the metal nanoparticles, the target chemicals of interest bind to their respective capture molecules, and the overall spectral peak of the sensor shifts according to the concentration of the chemical target on the capture molecules. In order to measure this shift, reflectance or transmission absorbance spectroscopy may be employed. Quantification is possible through comparing results to a previously-developed standard curve.

However, LSPR sensors suffer from low sensitivity and inadequate detection limits for a number of reasons.

LSPR sensors with nanoparticles on planar surfaces operate by flowing the sample longitudinally over the surface. In order for the sensor to determine the target concentration with the highest sensitivity and accuracy, the sensor must reach chemical equilibrium. Equilibrium occurs when the maximum fraction of capture molecule binding sites are occupied by chemical targets on the sensor surface, resulting in the largest sensor response in a reaction-limited assay. Lengthy incubation times are required to reach equilibrium.

Long incubation times are not suitable for many applications including point-of-care diagnostics. Long incubation times may be problematic for types of planar sensors other than LSPR sensors.

Reflectance LSPR signals from nanoparticles on a planar surface are also weak, leading to poor signal to noise ratios and poor detection limits. This may be addressed by using nanostructured surfaces to increase the surface area and nanoparticle density, resulting in a larger LSPR signal. However, this has the negative effect of increasing the time it takes to reach equilibrium and obtain the highest fraction of surface coverage since the number of surface sites is greatly increased. Essentially this improves signal to noise ratio but worsens the time to reach equilibrium, and overall does not greatly improve sensor performance. Moreover, these techniques rely on reflection measurement systems because the materials used are opaque at LSPR wavelengths and will not allow for transmission measurements.

For typical surface plasmon resonance (SPR) and localized surface plasmon resonance (LSPR) based devices used for the quantification of molecular binding interactions, a reference channel may be used to subtract interfering non-specific signals to produce a more accurate binding measurement. Sources of these nonspecific signals include but are not limited to, nonspecific binding interactions of target or non-target molecules with the sensor, solution phase bulk refractive index changes, as well as fluctuations in temperature or other experimental conditions. If these interfering signals can be quantified, they can be subtracted out from the sensing signal to obtain a more accurate response of the desired signal. The testing channel and testing sensor contain capture molecules on the sensor surface that bind specifically to the analyte of interest. To prevent the reference channel sensor from binding to the analyte of interest, the surface may be blocked with a neutral molecule. In this manner, all nonspecific changes such as those listed above will affect both sensors but the specific binding interaction will only affect the tested sensor. The difference in signal between the two sensors can then be used to subtract the non-specific effects from the effect of the analyte of interest.

The reference channel typically runs parallel or serial to the testing channel and is composed of a redundant sensor that may require separate light sources, detectors and microfluidics to be effective. Its presence increases the cost of the instrument, makes it more complicated and may require larger amounts of precious sample to operate. For the reference channel to perform correctly everything about it must be identical to the tested sensor. Since the reference channel requires a separate sensor and surface functionality than that of the testing channel, it is near impossible to produce a perfectly accurate reference signal. It also requires that the user design and produce a reference surface coating that is appropriate, adding to the experimental complexity.

LSPR-based molecular sensing using nanoparticles may also be carried out in solution phase, i.e. free floating nanoparticles not immobilized onto a substrate. Detection in solution phase is typically achieved by adding the analyte of interest to the solution of nanoparticles functionalized with capture molecules. This detection signal would normally include the nonspecific effect of the dilution of the nanoparticle solution along with any bulk refractive index shifts provided by the analyte and its buffer. These non-specific effects currently cannot be quantified without running additional control experiments, increasing the amount of sample to be used, time needed and complexity of the experiments. Similar to substrate-based SPR/LSPR sensing, it is near impossible to produce a perfectly accurate reference signal using this method.

SUMMARY

In one aspect, there is provided a sensor for LSPR detection of a target chemical. The sensor comprises a substantially transparent, porous membrane having nanoparticles such as metal nanoparticles immobilized on the surface of its pores, the nanoparticles being functionalized with one or more capture molecules.

In a further aspect there is provided an sensing apparatus comprising at least one LSPR light source; at least one detector and at least one sensor for LSPR detection of a target chemical located between the detector and the light source, the sensor comprising a substantially transparent, porous membrane, the membrane comprising nanoparticles immobilized on the surface of its pores, the nanoparticles being functionalized with one or more capture molecules.

In a further aspect of the invention there is provided a self-referencing sensor for LSPR detection of an analyte molecule in a sample and simultaneous detection of non-specific signal changes, the self-referencing sensor comprising one or more types of nanoparticles, the one or more types of nanoparticles having at least two distinct LSPR signals, wherein at least one nanoparticle type includes a capture molecule to bind to the analyte and whereby the non-specific signal changes can be distinguished from the analyte binding signal by a difference in a resulting optical spectrum change between the two distinct LSPR signals.

BRIEF DESCRIPTION OF THE DRAWINGS

Embodiments will now be described by way of example only with reference to the appended drawings wherein:

FIG. 4A is graphical representation of an enlarged top view of a sensor of FIG. 3;

FIG. 4B is an enlarged view of the graphical representation of the sensor of FIG. 4A depicting functionalized nanoparticles immobilized in pores;

FIG. 26A is a cross-section top view of a self-referencing sensor apparatus. FIG. 26B is a schematic depicting one nanoparticle type on one substrate. FIG. 26C is a schematic depicting another nanoparticle type on another substrate. Both substrates may interface with the same fluidic channel in the same optical path between the LSPR light source and the detector in the apparatus as shown in FIG. 26a.

FIG. 32A shows measured changes over time, of LSPR peak positions with addition of bulk refractive index changes (a) and a binding molecule (b). FIG. 32B shows the processed separated signals corresponding to specific binding and bulk refractive index changes.

FIG. 33A shows measured changes in LSPR peak position with addition of bulk refractive index changes (a) and a binding molecule (b). FIG. 33B shows the processed separated signals corresponding to specific binding and bulk refractive index changes.

DETAILED DESCRIPTION

It has now been realized that the long incubation times associated with existing LSPR sensors are due, at least in part, to the diffusion time required for target chemicals in a fluid to reach capture molecules on the sensor. One method to reduce the diffusion time of the chemicals in the fluid is to reduce the diffusion length. It has been realized that the diffusion length may be reduced by flowing a higher proportion of the sample a closer distance to the capture molecules. Specifically, it has been found that the diffusion time may be reduced by flowing a sample fluid through a relatively narrow-size pore having capture molecules immobilized on its surface. This causes the mean distance between target chemicals and capture molecules in a set volume of sample fluid to be reduced with respect to flowing the same volume of sample fluid over a planar surface comprising capture molecules.

Figure 1:
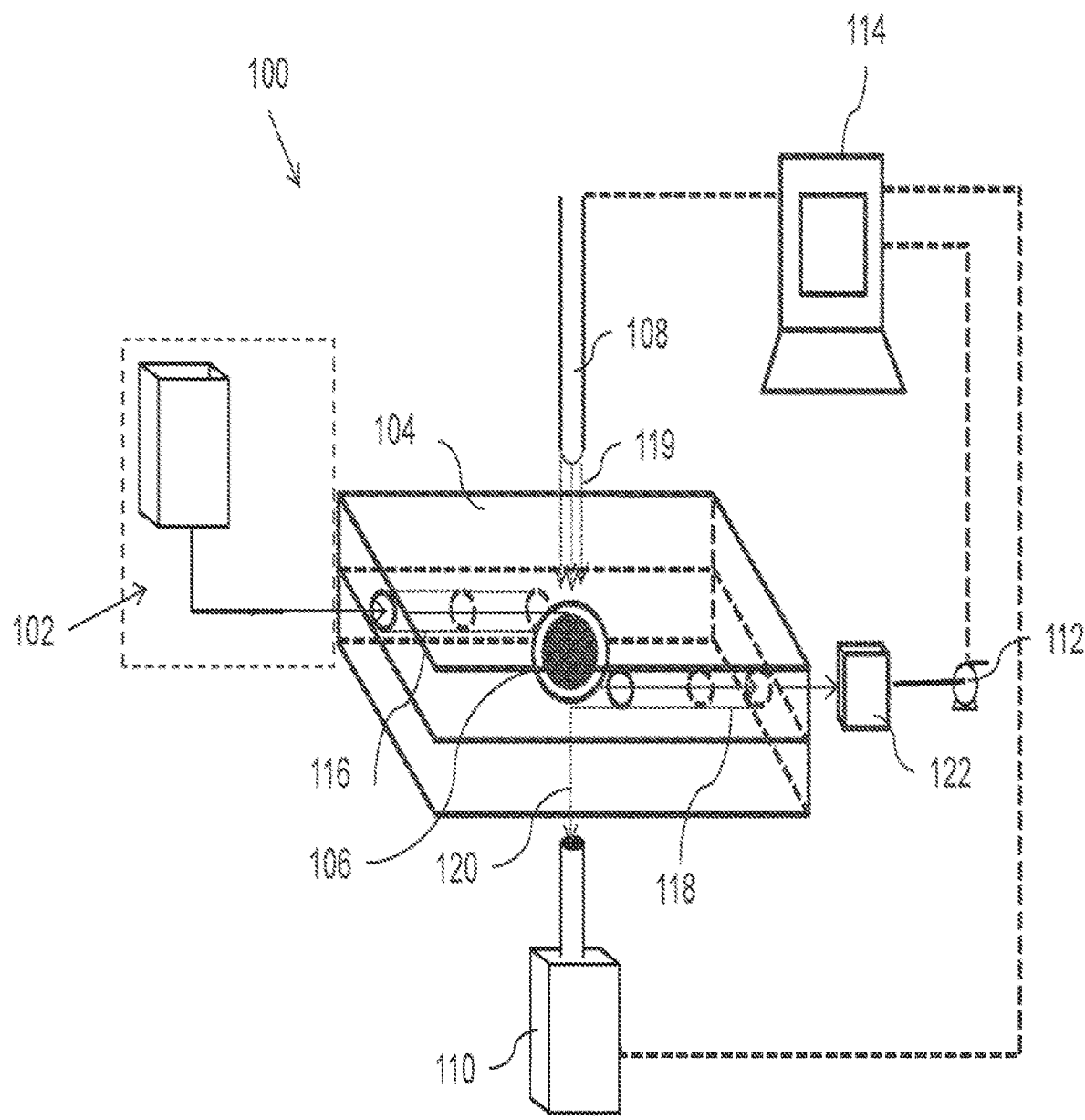
FIG. 1 is a diagram of a transmission-based three-dimensional chemical sensing system.

Referring now to FIG. 1, an example three-dimensional chemical sensing system 100 is provided. The chemical sensing system 100 comprises a fluidic cartridge 104, an inlet port 102, a signal processor 114, a light source 108 for LSPR measurement, and a detector 110. The chemical sensing system 100 may further comprise an outlet reservoir 122 and a fluid driving element such as a pump 112 or pressure source (not shown).

The pump 112, the light source 108, and the detector 110, may be electrically powered, for example, by a battery, a power outlet, or a combination of both. The chemical sensing system 100 may be located within a housing (not shown), for example, a portable housing such as a hand-held housing.

Inlet port 102, which is in communication with a fluid inlet 116, is operable to receive a fluid sample, for example from a syringe, and feed the fluid sample to the fluid inlet

116. The inlet port 102 may further comprise, or be linked to, a filter or mixing element to filter, pre-treat or mix a sample fluid.

The inlet port 102 may vary in form depending on the type of fluid sample that is being tested. For example, in the case of a blood sample for biological diagnostics, a sterile needle in a lancing device may be employed to obtain the sample similar to a glucose monitor. It will be appreciated that the inlet port 102 may comprise various other forms including Luer taper fittings, press fittings, or an open reservoir. It will be appreciated that the inlet port 102 may be built into the fluidic cartridge 104.

Figure 2:
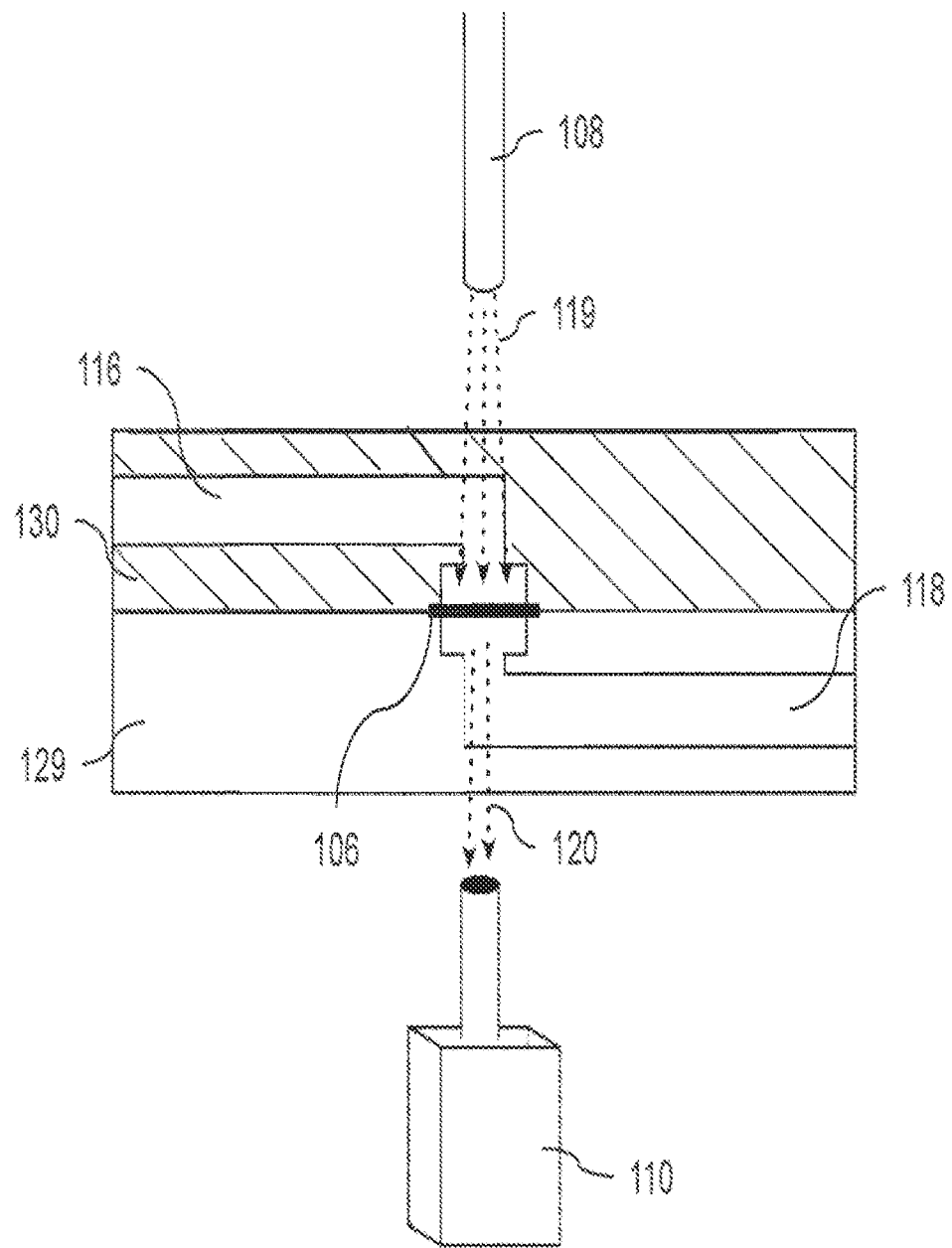
FIG. 2 is a side view of the fluidic cartridge of FIG. 1.
Figure 3:
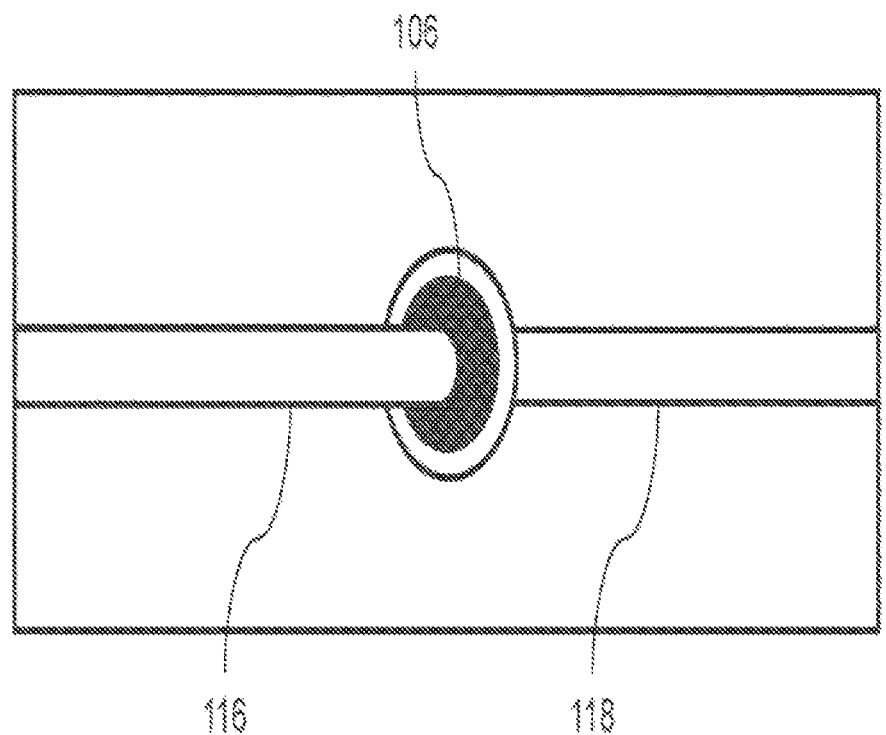
FIG. 3 is a top view of a fluidic cartridge of the chemical sensor of FIG. 1.

Referring now to FIGS. 2 and 3, the fluidic cartridge 104 comprises a fluid inlet 116, a sensor 106, and a fluid outlet 118. The fluid inlet 116 is fluidically connected to the sensor 106 and thereby, operable to deliver fluid to the sensor 106 to cause one or more target chemicals in the sample fluid to bind to capture molecules in the sensor 106, as is further described herein. It will be appreciated that the same sample may be transported to two or more sensors, for example, in a multiplexed design as demonstrated below with reference to FIG. 7.

The fluidic cartridge 104 may be disposable or designed for repeated use. The fluidic cartridge is composed of a material that is substantially optically transparent in the LSPR wavelengths being used. For example, polydimethylsiloxane (PDMS), is optically transparent over many LSPR wavelengths. In the example of FIG. 3, the sensor 106 is sandwiched between two layers of PDMS. Other transparent materials could be used to form the fluidic cartridge including, glass, poly(methyl methacrylate) (PMMA), cyclic-olefin polymer, or another material through which micro-channels may be formed to produce the fluid inlet 116 and the fluid outlet 118.

The fluid outlet 118 is also fluidically connected to the sensor 106 to receive fluid from the sensor 106 and allow fluid to egress from the sensor 106. Optionally, the fluid outlet 118 may deliver, to the outlet reservoir 122, fluid that has passed through the sensor 106. Alternatively, the fluidic cartridge 104 may retain the sample.

Although the fluid inlet 116 and fluid outlet 118 are shown in the simplest form in FIG. 3, the fluid inlet 116 and fluid outlet 118 may take different routes through the fluidic cartridge depending on specific requirements such as flow rate and sample volume or the need for mixing and pre-treatment steps. The dimensions and path of the fluid inlet 116 and fluid outlet 118 may be chosen depending on the desired fluid speed and mixing properties.

A pump 112, or other fluid driving element, may optionally drive the fluid from the inlet fluid channel 116, through the sensor 106 and out of the fluidic cartridge through the fluid outlet 118. For example, the fluid driving element may also comprise a pressure source or a vacuum source at the outlet port 118. The pump 112 can be controlled by the signal processor 114 or other controller. The direction of fluid flow can be rapidly and automatically switched via software control to move the sample back and forth transversely through a membrane in the sensor 106, allowing for prolonged interaction times with a small sample volume, thereby potentially increasing the performance of the sensor 106.

Alternatively, the fluid may be driven through the sensor 106 using, for example, electro-osmotic pumps, gravity, wicking of a membrane, or be driven by a syringe or other fluid source at the inlet port 102.

The signal processor 114 comprises, or is linked to, a memory, a processor, and a user interface which may include a display and an input device such as a touch screen or keyboard and mouse. The signal processor 114 may be linked to another input device, for example, a barcode scanner, an RFID scanner, or an NFC reader to identify a fluidic cartridge comprising an identifier, for example, a barcode, RFID tag, or NFC chip. It will be appreciated that other identification methods may be used including, for example, image analysis or a simple identification code which may be entered by the user. The identifier may comprise, or be linked to fluidic cartridge information such as relevant standard curves, the type of sensor being used, manufacturing date, etc.

The signal processor 114 may, in various examples, comprise a computer such as a laptop computer, desktop computer, microcomputer, cloud-based processor, or a mobile device. The memory of the signal processor 114 may contain fitting algorithms and standard curves. The signal processor 114 may be linked to one or more of the pump 112, light source 108, or detector 110 via a wired connection, for example a local area network or USB connection. Alternatively, or in addition, signal processor 114 may be linked to one or more of the pump 112, light source 108, or detector 110 via a wireless connection such as Bluetooth, Wi-Fi, or cellular connection. In some embodiments, the signal processor 114 may be located remotely from the fluidic cartridge 104.

The signal processor 114 may control the light source 108 to emit light into the sensor 106. An example light source 108 comprises a white light emitting diode (LED) and is coupled to a detector 110 comprising a UV-visible spectrometer. White light sources other than LEDs such as halogen bulbs and others such as red, green, and blue LEDs separate or combined together, may also be used. A light source for the visible range (400-800 nm) could be a white light source such as a halogen bulb or an LED, a combination of colored LED light sources such as red, blue, and green, a single colored LED light source, or a laser at a specific wavelength. For operation below the visible range (100-400 nm) of the spectrum, an ultraviolet (UV) light source such as a UV LED could be used. For operation above the visible range (800-2500 nm) an infrared (IR) source such as an IR LED could be used.

The detector 110 may comprise a charge coupled device, a photodetector, a spectrometer, a photodiode array, or a combination thereof, to obtain LSPR light intensity readings. The detector 110 may comprise a spectrometer or photodetector designed for parts of the electromagnetic spectrum outside the visible range, including the ultraviolet (UV) range, the near infrared (NIR), or IR range. The detector 110 may comprise a combination of two types of detectors, for example, a photodetector and a spectrometer. The detector 110 is selected in combination with an appropriate light source 108.

The light emitted by the light source 108 is transmitted though the fluidic cartridge 104 and sensor 106 and is received, at least in part, by a detector 110. As mentioned above, the fluidic cartridge 104 and sensor 106 must be at least partially transparent to the LSPR wavelengths emitted by the light source 108. The detector 110 generates a transmission signal, for example a digital transmission signal, based on the light transmitted through the sensor 106 and provides the signal to the signal processor 114. The signal processor 114 is operable to produce a spectrograph based on the transmission signal. The signal processor 114 may also be operable to select an output based on a predetermined transmission signal or a comparison between the transmission signal and one or more reference signals or thresholds. For example, the signal processor 114 may output the concentration of a target chemical based on a transmission signal that is consistent with one or more reference signals, or exceeds a threshold of an established reference signal. The signal processor may also be used to determine biointeraction analysis parameters between the target and capture molecule, which may include reaction kinetic information (on and off rates), affinity, and specificity. A simple photodetector may be used to measure intensity changes due to the spectra shifts.

In the example of FIG. 1, the sensor 106 is substantially planar and is located laterally between the path of the light source 108 and the detector 110. As a sample fluid flows through the sensor, the light source 108 emits light and the spectrometer 110 receives light continuously, or at predetermined intervals, to monitor changes in the resonance peak of the detected light. The light source 108 and detector 110 may be arranged for maximal illumination of the sensor and maximal capture of the light transmitted through the membrane, respectively. FIG. 1 shows a transmission based LSPR arrangement, wherein the light source 108 shines through the membrane and to the detector 110.

It has been found that to address, at least in part, the sensitivity of LSPR-based chemical detection, a three-dimensional porous membrane is used as a substrate for sensor 106. Functionalized metal nanoparticles are immobilized within the pores of the membrane and a sample is flowed through the pores. Such a sensor design may be referred to herein as a transmission-based three-dimensional sensor (T3D). The three-dimensional porous membrane is substantially transparent for the wavelengths of incident light that are used to obtain a signal.

Turning to FIGS. 4A and 4B, the sensor 106 comprises a nanoporous membrane. Pores 148 of the membrane comprise functionalized metal nanoparticles 150 immobilized on their surfaces. Specifically, the membrane is characterized by nanopores, which are channels 10 nm-1000 nm in diameter and can be up to 200 μm long. For example, the nanoporous membrane may comprise pores that are about 25, 50, 100, 150, 200, 250, 300, 350, 400, 450, and 500 nm in diameter, and about 1, 5, 25, 50, 75, 100, 150 and 200 μm in length.

A sample is flowed through the pores 148 of the membrane, which have relatively small diameters. The relatively small pore diameters, for example about 100 nm, limits the diffusion distance between the chemical targets and their corresponding capture molecules on the nanoparticle surface, thereby reducing the mean diffusion time required for a target chemical to reach a capture molecule. By reducing the diffusion time, the time required for the target-capture molecule system to reach equilibrium may be decreased. The nanoparticles may also be bound to the top and bottom surfaces of the nanoporous membrane.

The working area of a sensor is limited to the width of the coherent light source, which may be approximately 1-4 mm. It is therefore impractical to increase the sensitivity of sensors of the prior art simply by creating a larger planar (two-dimensional) sensor. However, because functionalized nanoparticles are immobilized onto pore surfaces in a three-dimensional membrane, the number of nanoparticles over a given sensor area can be increased with respect to a similar two-dimensional design. In many cases, the number of nanoparticles immobilized within a given sensor area may be increased substantially with respect to a two-dimensional design.

The membrane may be selected to optimize the thickness, pore size, and pore periodicity for a particular chemical sensing application. The diameter of the sensing membrane can be selected based on cost and performance. In an example, the diameter of the sensing membrane may be as small as 1 μm or as large as 13 mm. The light beam size may be close to the diameter of the sensing membrane to maximizing the strength of the absorbance signal. The diameter of the sensor may be small to reduce cost.

Anodized aluminum oxide (AAO) is an example nanoporous membrane material. The dimensions of nanopores in an AAO membrane may be controlled when producing the AAO material. The material is sufficiently optically transparent at LSPR wavelengths to allow for transmission-based spectroscopic measurements to be performed. The transmission of light through the membrane is dependent on several factors including pore size and thickness that impact the absorbance of the membrane material and the scattering it produces in the LSPR wavelengths of interest.

Figure 16:
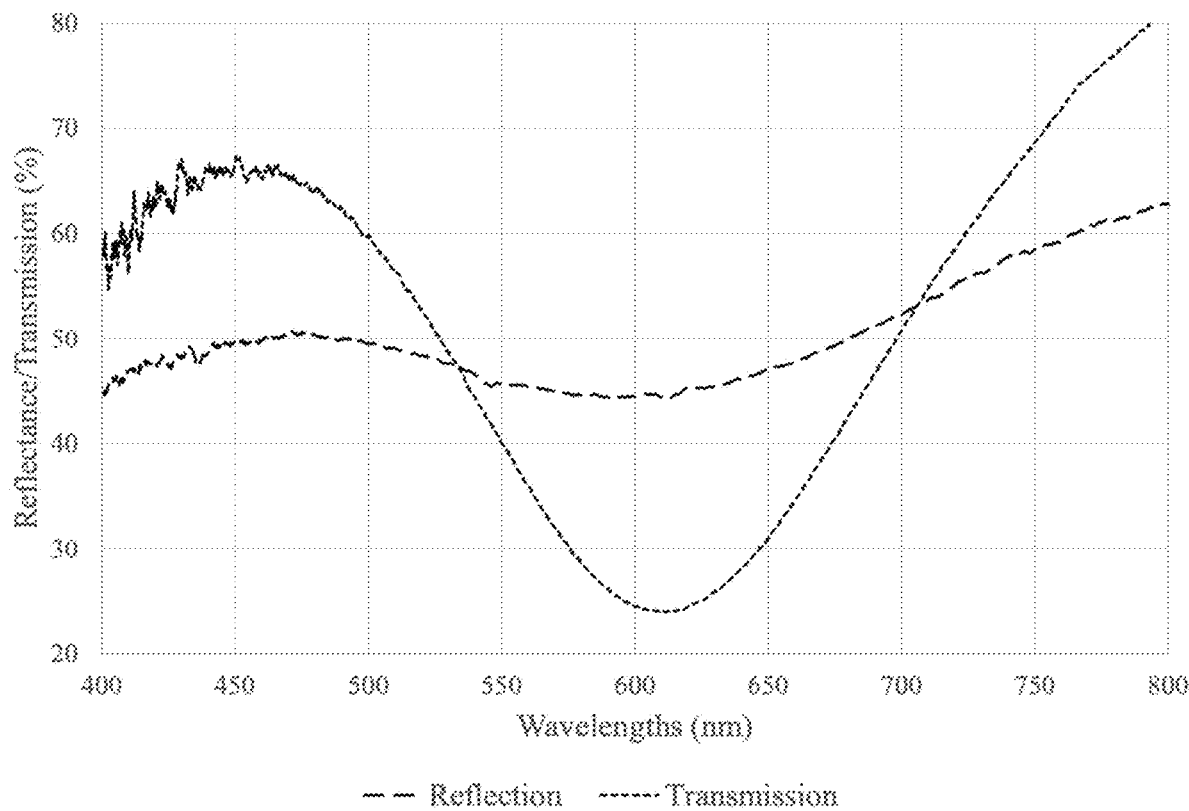
FIG. 16 is a graph showing a comparison of reflection and transmission signal of AAO membrane with 150 nm pores and 50 um thick, with 45 nm gold shell nanoparticles immobilized inside the pores. The LSPR peak is much larger and sharper in the transmission measurement.

Although both reflection and transmission measurements are possible with this system, is has surprisingly been found that transmission measurements provide better results than reflection measurements. In reflectance mode the reflection off of the top surface of the membrane is strong, and accounts for the majority of the signal returning to the detector. This reflected light carries very little nanoparticle absorbance information with it as it is only interacting with the nanoparticles on the top surface of the membrane. In transmission mode, the majority of the light passes through the entire thickness of the membrane before it reaches the detector, interacting with all of the nanoparticles throughout the entire thickness of the membrane. This greatly increases the absorbance component caused by the nanoparticles, increasing the signal to noise ratio and thereby increasing sensor performance. This also ensures that the measured signal is from target binding sites throughout the membrane rather than just those at the top surface. It has further been discovered that a larger proportion of scattering light reaches the detector in reflection mode versus transmission mode, increasing the noise. Also, the AAO pores act as a waveguide, allowing light to propagate within the pores and providing enhanced interaction with the nanoparticles, resulting in unexpectedly high transmission of light with a large LSPR absorbance component, providing further enhancements to the transmission signal which are not obtained when employing reflection signal. FIG. 16 illustrates the dramatic improvement in the LSPR signal when measuring in transmission versus reflection.

However, a transmission system is more difficult to build as the LSPR wavelengths must be matched to the AAO properties to allow sufficient light transmission. Variables such as pore size, and thickness may be tuned depending on the wavelengths used so as not to interfere with the optical signal generated by the immobilized metal nanoparticles. The transmission apparatus can be realized by having a light source on one side of the membrane and a detector on the other side of the membrane. It is also possible to make a pseudo-transmission setup with the light source and detector on the same side of the membrane, if a highly reflective surface is placed beneath the membrane. The reflective surface will cause the transmitted light to travel back through the membrane and to the detector on the opposite side, which is effectively a transmission measurement.

Figure 17:
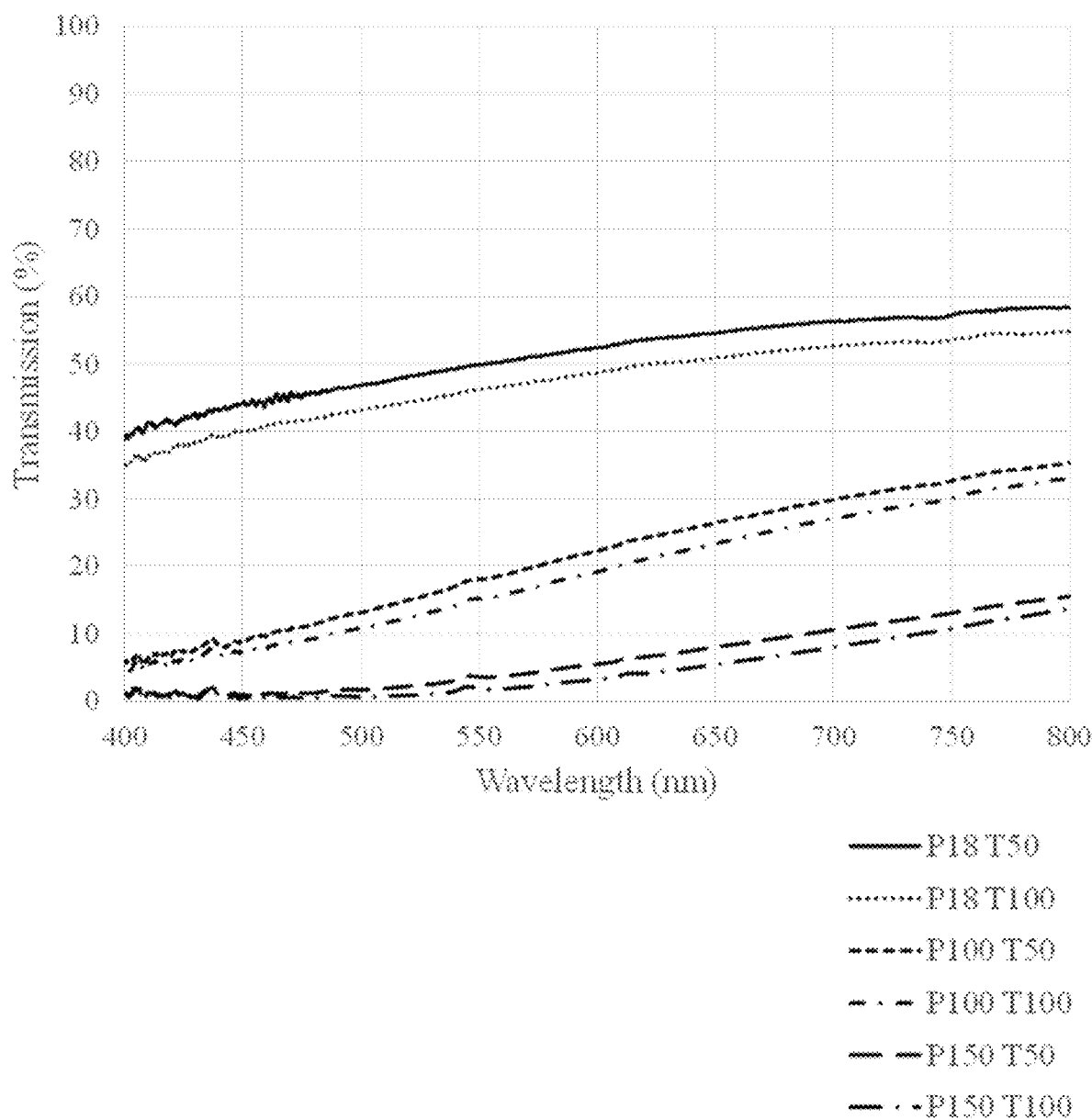
FIG. 17 is graph showing transmission of AAO membranes of various pore size (P, in nm) and thickness (T, in um). Membranes were measured dry in air.
Figure 18:
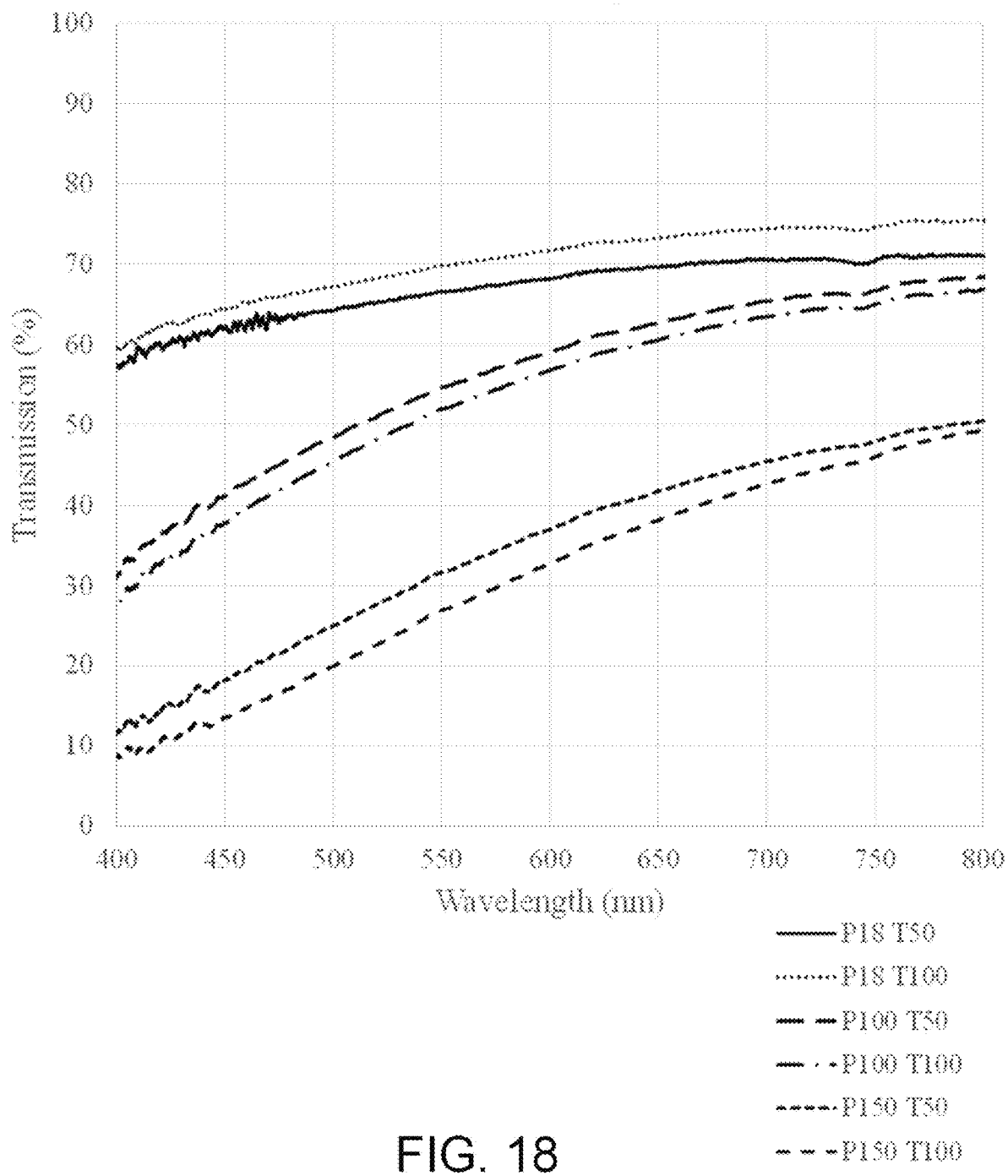
FIG. 18 is a graph transmission of AAO membranes of various pore size (P, in nm) and thickness (T, in um). Membranes were measured wetted with water in air.

In FIG. 17 and FIG. 18, the transmission of various AAO membranes with different pore sizes and thicknesses have been measured both dry and wet with water. In general, smaller pores result in higher transmission compared to larger pores. With respect to thickness, thinner membranes (50 μm) have higher transmission compared to thicker membranes (100 um), but the impact is not as significant as pore size. To use AAO as a material in this sensor, the pore size and thickness should be selected to be as small as possible while still allowing the nanoparticles to fit into the pores without blocking them. Now examining the dry vs wet membranes, the transmission through wet membranes is improved, due to refractive index matching, especially for membranes with larger pore sizes (100 and 150 nm). To get the best results, measurements should be taken while the membrane is wet. To further improve the transmission, a high refractive index solution can be introduced after the sample has passed through the sensor. The high refractive index solution will reduce scattering even further, improving the signal to noise ratio.

Any optical signal that is generated by the membrane itself can be removed from spectroscopic measurement by the signal processor 114 using baseline correction methods. A reference measurement of an area of the membrane which is not coated in nanoparticles may be taken to subtract out the optical signature of the membrane using the processor 114, which may enhance the signal produced by the nanoparticles. Pores of a membrane, for example an AAO membrane, can be chemically treated to allow metal nanoparticles 150 to be associated with its surface. For example, the chemicals used to treat AAO include, but are not limited to, polyelectrolytes such as polyallylamine hydrochloride (PAH) and poly-(succinyl-sulphonate) (PSS) that can create a positive or negative electrostatic charge on the AAO surface. Metal nanoparticles stabilized in water by charged surface groups can be associated to the membrane through electrostatic forces. Other methods to immobilize nanoparticles include using a silane based linker, which will covalently bind to the surface of the AAO. For example, a silane-thiol molecule could be used, with the silane covalently binding to the AAO pore wall and the thiol covalently binding to the nanoparticle. The thiol could be replaced with any chemical group that associates to the nanoparticle surface, such as an amine group, for example. The AAO may be pretreated to generate hydroxyl groups on the surface of the pores to promote silanization, through a procedure such as incubation in a 1:1 solution of hydrochloric acid and methanol for 30 minutes, or any other method that can be used to generate hydroxyl groups the surface.

It will be appreciated that various other nanoporous membrane materials may be used including various organic and inorganic membranes that are at least partially transparent at the LSPR wavelengths of interest. Advantageously, metal nanoparticles may be associated directly to these membranes if the membranes contain thiol-, amide-, phospho- or other functional groups.

The membrane material could also be chemically treated with polyelectrolytes such as PAH, PSS or other charged polymers to associate the metal nanoparticles to the surface through electrostatic interactions. Reaction chemistry such as N-Hydroxysuccinimide/ethyl(dimethylaminopropyl) carbodiimide (NHS/EDC) coupling among other coupling chemistries may also be used to bind the metal nanoparticles to the surface. It will be appreciated that there exist other methods of immobilizing functionalized metal nanoparticles 150 to an optically transparent nanoporous material.

Figure 4C:
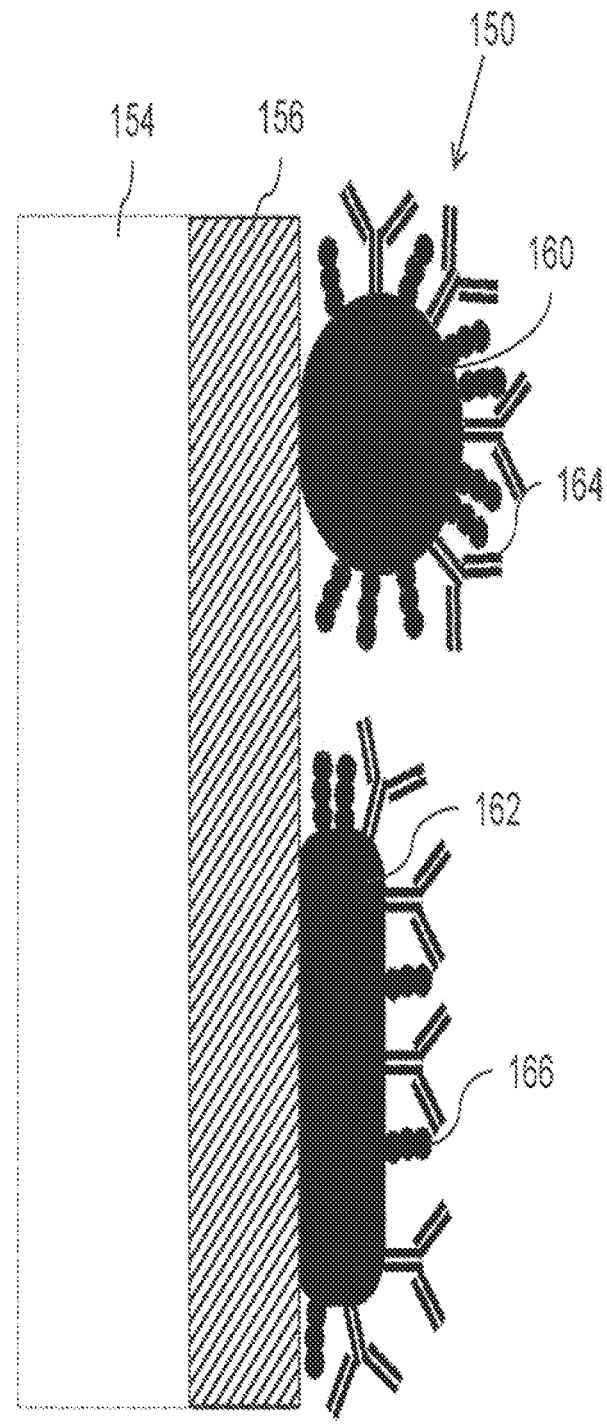
FIG. 4C is an enlarged side view of a pore of FIG. 4A depicting functionalized metal nanoparticles.

Turning now to FIG. 4C, an example of functionalized metal nanoparticles 150 functionalized to a pore surface of an AAO membrane is provided. The AAO membrane 154 has a bilayer of charged polyelectrolyte 156 on its surface that facilitates the association of charged metal nanoparticles 150 to the walls of the pores.

The metal nanoparticles shown in the example of FIG. 4C have two different metal core shapes, a sphere 160 and a rod 162, which may be used together or independently. Both are functionalized with antibodies 164 as the capture molecule with their distinctive Y-shape and form a self-assembled monolayer (SAM) on the surface of the nanoparticle. Blocking molecules 166 prevent non-specific binding to empty binding sites on the metal surface. The capture molecules may also comprise aptamers, polymers, or DNA The SAMs may comprise an antibody, aptamer, polymer, DNA or other capture molecule that is bound to the nanoparticle 150 surface and capable of selectively binding to the chemical of interest. In the case of gold nanoparticles, this binding typically occurs spontaneously between the gold surface and thiol groups that are natural to the capture molecule or have been chemically added to the capture molecule or nanoparticle surface.

To prevent non-specific binding of non-target chemicals, inert blocking molecules are used to pacify empty binding locations on the nanoparticle and pore surfaces. Blocking molecules for metal nanoparticles may comprise thiolated compounds with inert end groups that provide aqueous stability such as carboxyl, methyl, or polyethylene glycol (PEG). For the pores, blocking molecules may be silane based compounds with inert end groups such as carboxyl, methyl, or PEG. Bovine serum albumin (BSA) is another example of a possible blocking molecule that may be used on nanoparticle and pore surfaces. Together, the capture and blocking molecules form a SAM that imparts functionality onto the metal nanoparticle.

To create a functional sensor 106, the metal nanoparticles are first immobilized on the nanoporous membrane surface then the nanoparticle is functionalized with a SAM. Alternatively, the particle may first be functionalized with a SAM and the nanoparticles may be immobilized on the membrane.

The size, shape and elemental composition of metal particles affect the location and intensity of the LSPR absorbance peak in the electromagnetic spectrum. As such, the size, shape, and composition of nanoparticles are selected to allow for a measureable transmission signal through the nanoporous membrane. The size and shape of the nanoparticles are also selected to avoid physical clogging of the pores of the selected sensor membrane.

Various metal nanoparticles have different bulk refractive index sensitivities and electromagnetic decay lengths, which may be tuned to produce the optimal LSPR sensor response for a given capture-target system. Decay length and sensitivity are typically not independent parameters, and both can be tuned with the size, shape, and composition of the nanoparticle. For example, increasing the size of a spherical nanoparticle increases both the sensitivity and the decay length. Other nanoparticle shapes may have different trends with respect to size, sensitivity, and decay length. Preferably, a nanoparticle will have the highest sensitivity with a decay length that is similar to the thickness of the capture molecule-target complex. For example if the total size of the capture molecule-target complex is 8 nm, the optimal decay length would be near 8 nm. As such, the size, shape, and composition of the nanoparticle can be tuned based on the sensitivity and decay length parameters for a particular capture molecule-target complex. This also must correspond with the necessary optical properties to allow sufficient transmission of the LSPR signal through the membrane.

Therefore the nanoparticles can be selected depending on the one or more specific chemical target being investigated by the sensor 106.

Compositions of metal nanoparticles that can be used for LSPR include gold, silver, platinum, gold coated silver, silver coated gold, combinations of these metals, and others. The shape of the nanoparticles used can also vary. Useful nanoparticle shapes include but are not limited to, rods, stars, urchins, decahedra, hexagons, triangles, shells, prisms, platelets, spheres, rice, plates, cubes, cages, stars and bipyramids. The dimensions of the metal nanoparticles can range between about 1 nm and 1000 nm with a variety of area to volume ratios.

Figure 4D:
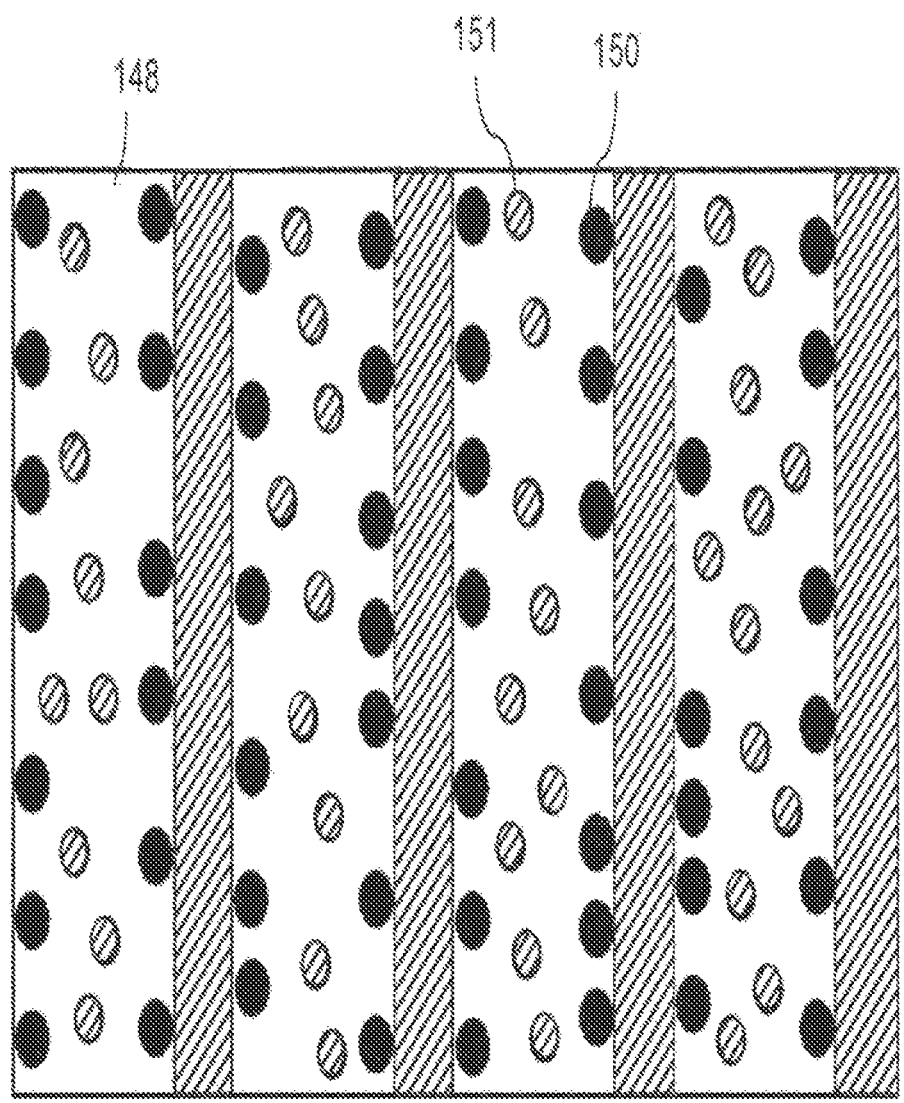
FIG. 4D is another enlarged view of a pore depicting various types of functionalized metal nanoparticles immobilized the pore.

Referring now to both of FIGS. 4C and 4D, a combination of two or more types of nanoparticles may be immobilized on the surface of a single membrane. Each of the nanoparticle types may have been functionalized with a specific capture molecule. For example, nanoparticle 150 may be functionalized with capture molecules to capture a first target chemical whereas nanoparticle 151 may be functionalized with capture molecules to capture a second target chemical.

Figure 19:
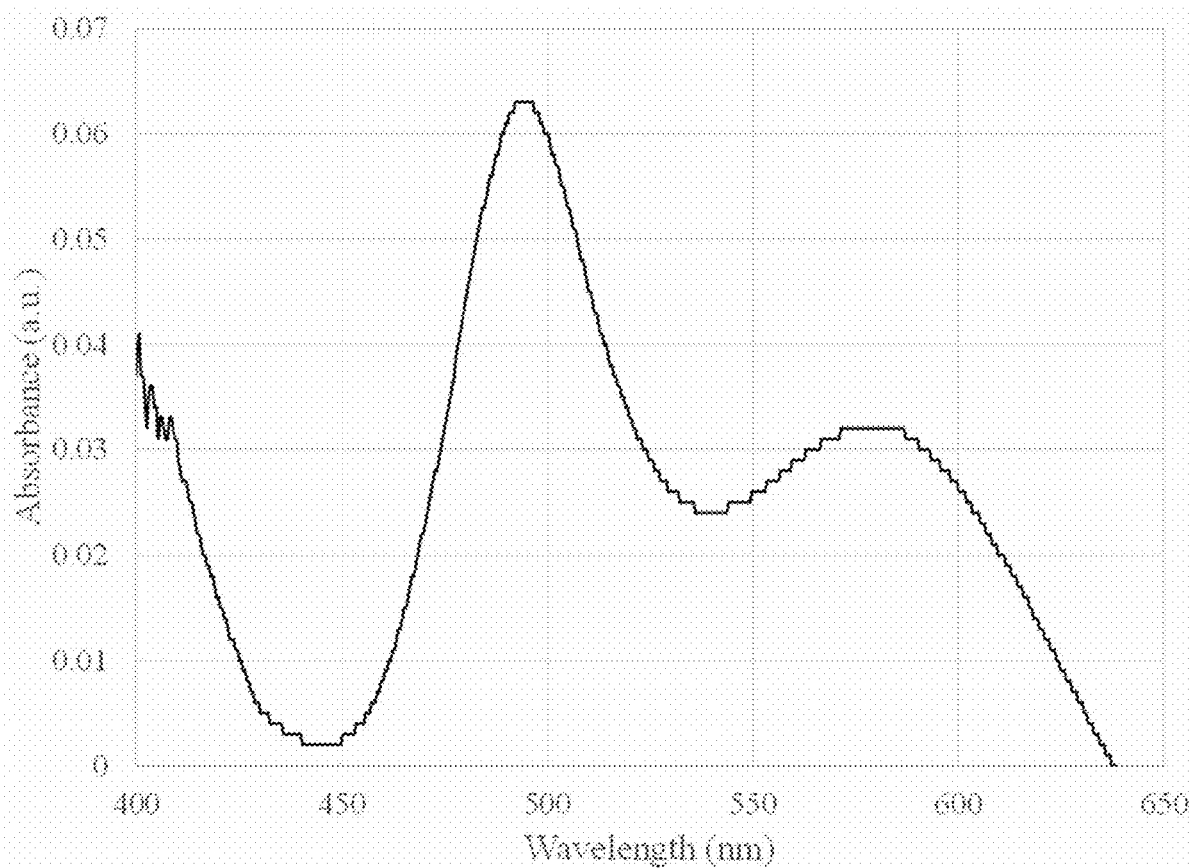
FIG. 19 is an absorbance spectrum of an AAO membrane containing nanoparticles with two different LSPR peak positions, one located at approximately 495 nm and the other at approximately 580 nm.

With a combination of different nanoparticles (shapes, sizes and/or metals) functionalized to capture different targets, antibodies on the spherical nanoparticle may be selective to different targets from antibodies on the rod nanoparticle, each nanoparticle producing a distinct signal. Therefore, the concentration of each target can be determined from a single absorbance spectrum if the spectrum from each of the different particles does not overlap to such a degree that deconvolution of the peaks is impossible. Various particles are used to allow the detection of multiple targets on a single membrane. FIG. 19 shows two different particles immobilized in the same membrane, one with a resonance at approximately 495 nm and the other with a resonance at approximately 580 nm. The two peaks are clearly distinguishable and can be used for generating two independent signals from a single sensor. Any combination and any number of nanoparticles with different LSPR peak positions may be used to achieve multiple measurements. The incorporation of multiple particles with different LSPR peak positions within a membrane allows for a higher density of each particle to be present compared to the case if multiple particles were incorporated onto a planar substrate. Higher particle densities may offer better sensor performance due to high signal to noise ratios. This system may allow detection of multiple targets using a small initial sample which may be very advantageous in the case where sample is limited or difficult to obtain. Detecting multiple targets in tandem may also speed the time to obtaining results.

Various particles could also be attached to distinct areas of the same membrane using a tool similar to a protein spotter or various microchannels to allow geometrical separation of the particles. This is advantageous if using a photodetector rather than a spectrometer, or if cross reactions may occur between particles due to their chemically modified surfaces. The use of different particles on a single membrane can also facilitate the use of a control sensor to compensate for errors induced by non-specific binding, temperature change, bulk refractive index change, or other factors. This could be achieved by functionalizing one nanoparticle with a capture molecule and blocking molecule, and functionalizing a second particle with only a blocking molecule similar to the blocking molecules used in the first nanoparticle. Any peak changes that are detected from the second nanoparticle are erroneous, and as such, the second nanoparticle acts as a control. The different nanoparticles may be spectrally distinct or geometrically distinct.

Nanoparticles are immobilized onto the membrane walls through contact between the walls and a colloidal nanoparticle mixture. To permeate the nanoparticles throughout pores of the membrane, a variety of techniques may be employed. The nanoparticles may be physically pumped through the membrane, they can be driven into the membrane through the use of electrical potential, and they could enter by diffusion among, other methods.

Figure 22:
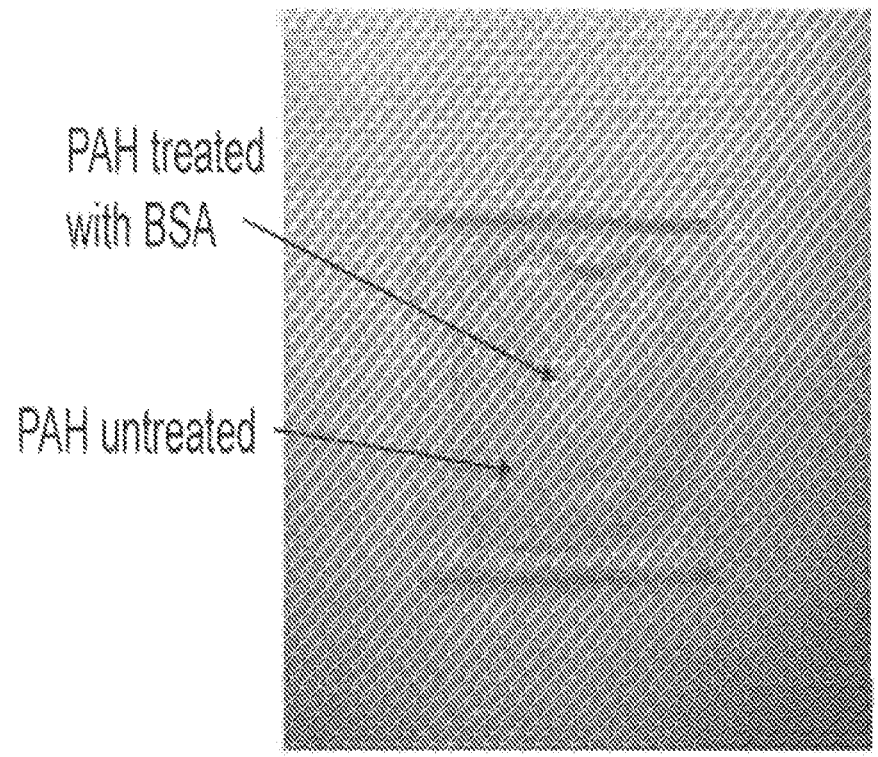
FIG. 22 shows that BSA prevents nanoparticles from binding to a PAH treated surface, on a glass slide.

The metal nanoparticles must remain relatively dispersed while immobilized in the pores, as extensive aggregation will affect the quality of the measurements due to peak broadening or pore clogging. It has been discovered that in order to improve the penetration and dispersion of the nanoparticles throughout the membrane pores, surface stabilizing additives can be included in the colloidal nanoparticle mixture. Alternatively, or in addition, the additives may be applied before the nanoparticles are immobilized on the membrane by pumping or incubating the additives through the membrane before the colloidal nanoparticle mixture is applied. It has been discovered that surface blocking additives are especially important in order to immobilize large nanoparticles into small pores. For example, AAO membranes with 100 nm pores were treated with PSS then PAH to render the surface positively charged. Gold nanoparticles 20 nm in diameter and coated in negatively charged citrate were pumped through the PSS/PAH coated membrane. No gold particles were observed to bind to the AAO pores. Upon addition of 0.01% BSA to the 20 nm gold colloidal solution and pumping through the membrane, gold nanoparticle binding was observed on the AAO pores. It is hypothesized that the zwitterionic nature of BSA acts to help stabilize the nanoparticles, possibly by screening the charges at the top surface of the AAO membrane, allowing the nanoparticles to more easily enter and travel through the membrane. In another experiment, a PSS/PAH modified 150 nm AAO membrane was dipped into a 1% BSA solution and rinsed with water. A 20 nm gold colloidal solution, without any BSA additive, was pumped through the membrane, and nanoparticle binding was observed. Binding was observed in the pores at a high density, with a low density of binding on the membrane surface. Increasing the BSA dip concentration to 10% caused a reduction in the binding density of the nanoparticles within the pores, with almost no nanoparticles present on the surface of the membrane. A control experiment was done on glass with a coating of PAH. BSA at 0.01% was incubated in a small droplet on the surface of the glass and rinsed away. A 20 nm gold colloid solution was then applied to the glass. Nanoparticle binding was observed to occur in areas in which there was no BSA, demonstrating that BSA may prevent the nanoparticles from binding to the PAH treated surface. This is shown in FIG. 22. A final experiment was performed with a PSS/PAH modified 150 nm membrane dipped in 1% BSA. 0.001% BSA was added to the gold colloid solution and pumped through the membrane. Binding was observed in the pores and on the surface but at a lower density than without the BSA additive. BSA, acting as a surface blocker, can be used to reduce membrane surface binding, helping to prevent agglomeration. BSA can also act as a stabilizer, allowing larger particles to more easily enter smaller pores. As we have demonstrated, smaller pore sizes are more transparent and so may be preferable to use. Also, larger nanoparticles have higher sensitivities, so they may also be preferable to use. So the use of surface stabilizing additives may allow a better sensor to be fabricated. Other possible additives include various inorganic salts, various surfactants such as Tween 20 or Triton X, or PEG, along with a variety of other potential molecules and combinations. It is also assumed that these additives will have similar effects when other nanoparticle binding methods are used other than charge interactions based on PSS/PAH, such as covalent methods using thiol chemistry as described previously.

The nanoparticles may be functionalized with capture molecules before or after they are immobilized on the pore walls. If they are immobilized prior to being functionalized, they can be immobilized on the pore walls through electrostatic interactions or using functional groups bound to the membrane that would be capable of binding to the nanoparticles, for example, in the case of a gold surface of a nanoparticle a thiolated polymer may be used. If the nanoparticles are functionalized prior to being immobilized, as they may be in the case of a multiplexed sensor, for example, a functional group would be used.

Alternatively, nanoparticles 150 and 151 may be functionalized to capture the same target chemical and any difference in signal could be used to generate a baseline signal, thereby removing uncertainty in the signal.

Figure 5:
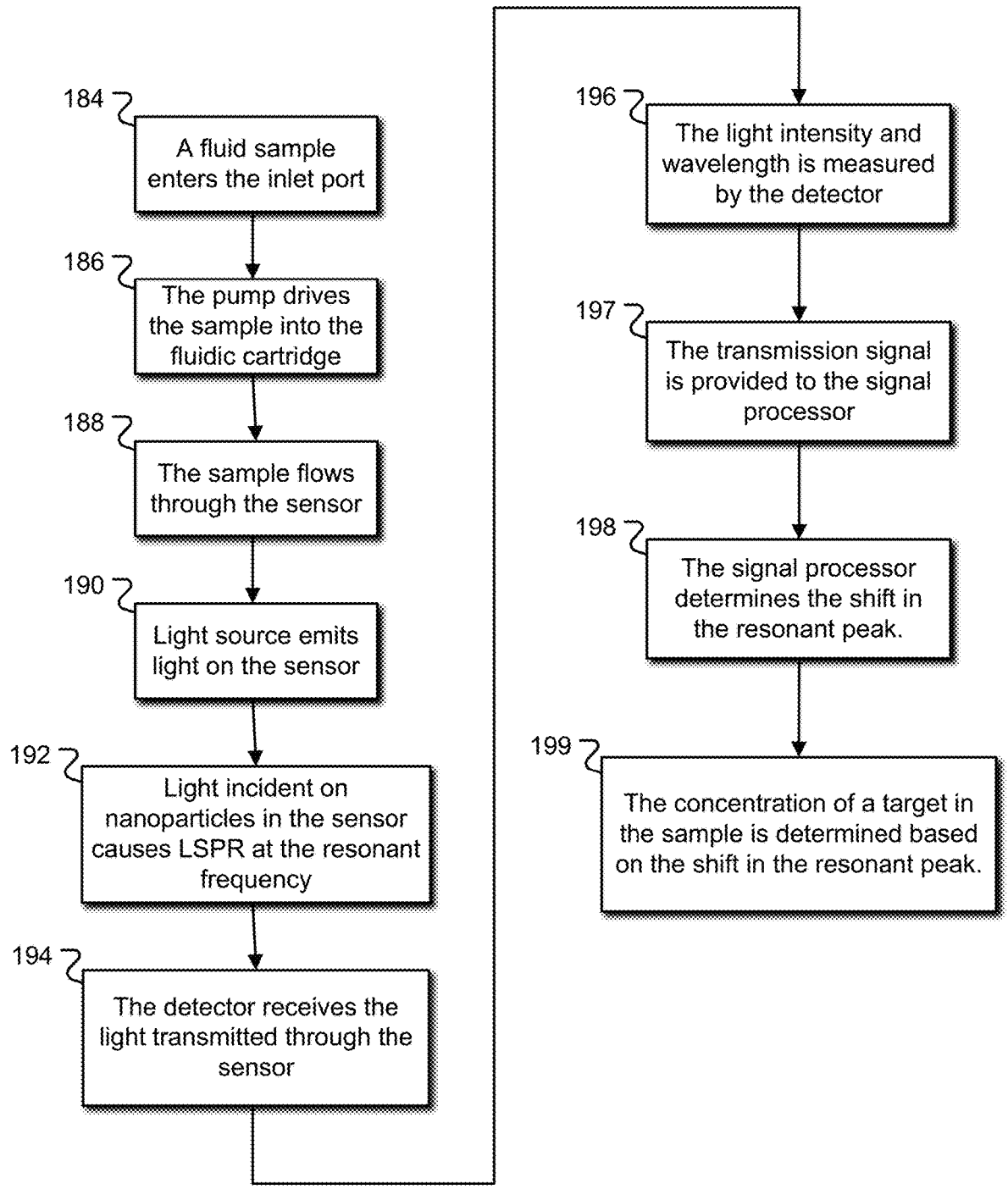
FIG. 5 is an process flow diagram outlining an example for obtaining a reading from the chemical-sensing system of FIG. 1.

Turning to FIG. 5, an example process for sampling a fluid is provided. In step 184, a sample fluid enters the inlet port 102. In 186, the pump 112 drives the sample into the fluidic cartridge 104 and the sample flows through the sensor 106 in step 188. In step 190, the light source 108 emits light onto the sensor 106 in the fluidic cartridge 104, which causes LSPR interactions in 192. In 194, the detector receives light transmitted though the sensor 106, measures the light intensity and wavelength in 196 and generates a transmission signal in 197. In 198, the signal processor 114 determines whether a shift in the resonant peak is observed and in 199, detects the presence and/or determines the concentration of the target chemical in the sample based on the resonant peak shift, as described above.

Figure 6:
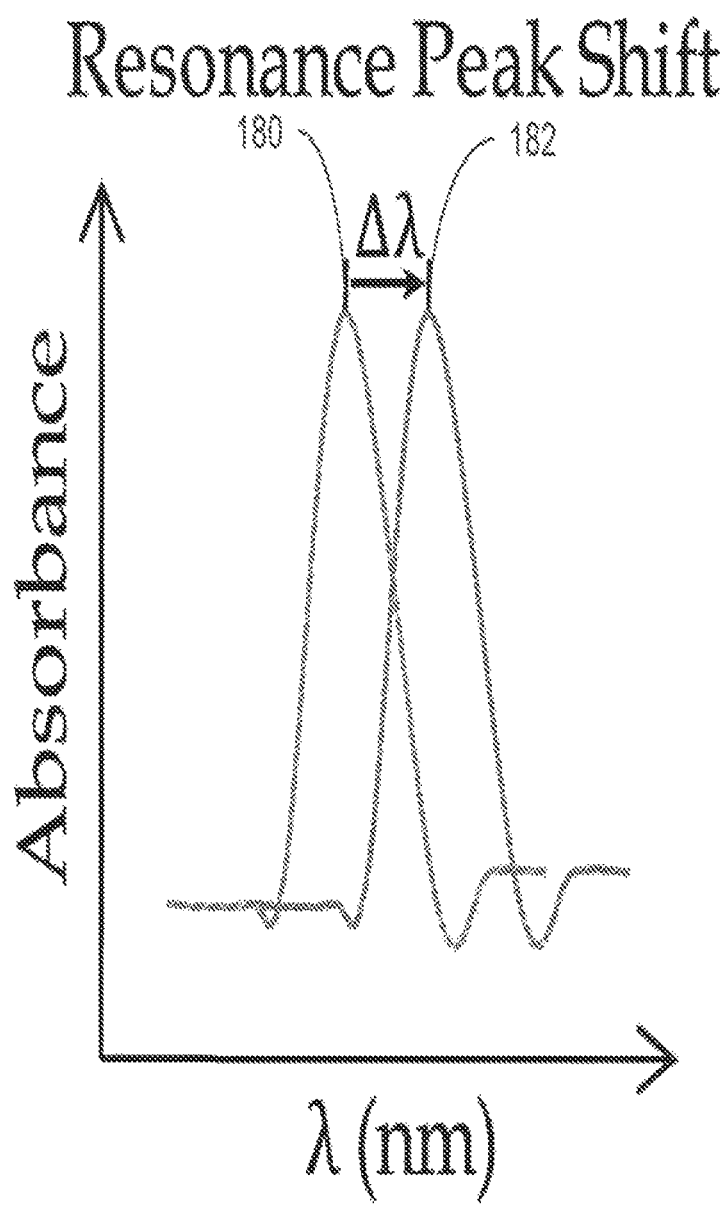
FIG. 6 is a plot showing the resonance peak shift due to binding of the target chemical with capture molecules on a sensor.

Referring now to FIG. 6, the change in peak position or intensity induced by binding of the target chemical to the capture probe can be monitored in real time or by comparing the peak position prior to the target chemicals binding to the capture molecules in the sensor 106 with the peak position after the target chemical has bound to the capture molecules in the sensor 106. This binding may be referred to as a binding event.

The change in peak position can be compared to data obtained from a standard curve of peak change vs. concentration by the signal processor 114, and using a fitting algorithm the presence of a target chemical in a sample may be detected, and the concentration of the target in the sample may be determined, by the signal processor 114. Alternatively, or in addition, the rate of change (the slope) of the signal may be used to more rapidly determine the concentration by comparing the calculated slope to data obtained from a standard curve of slope vs. concentration. Various data processing mechanisms may be employed by the signal processor 114 during data collection to improve the signal to noise ratio of the optical signal, such as smoothing and averaging functions. High speed acquisition is used to facilitate real time averaging and smoothing. Various peak fitting algorithms may be employed that offer a high level of stability in the peak position.

An indication of whether a target chemical was detected may be output by the signal processor 114. The indication may be output, by way of example, on a display, as an indicator light, as a warning signal, or as an electronic message. Alternatively, or in addition to the indication, the concentration of the target chemical may be output by the signal processor 114 or on a display linked to the signal processor such as the display of a cellular phone. Results of assays can be stored in built in memory on the device, on peripheral devices, or stored in a cloud-based server.

The spectrometric optical measurements taken through the membrane expose the surface area of the membrane and all of the particles contained therein, and hence, the sensor may be referred to as a three-dimensional sensor. A single sensor 106 may be adapted to detect multiple targets within a single fluid sample through the inclusion of multiple membranes or functionalized particles with different shapes, sizes or metals.

Figure 7:
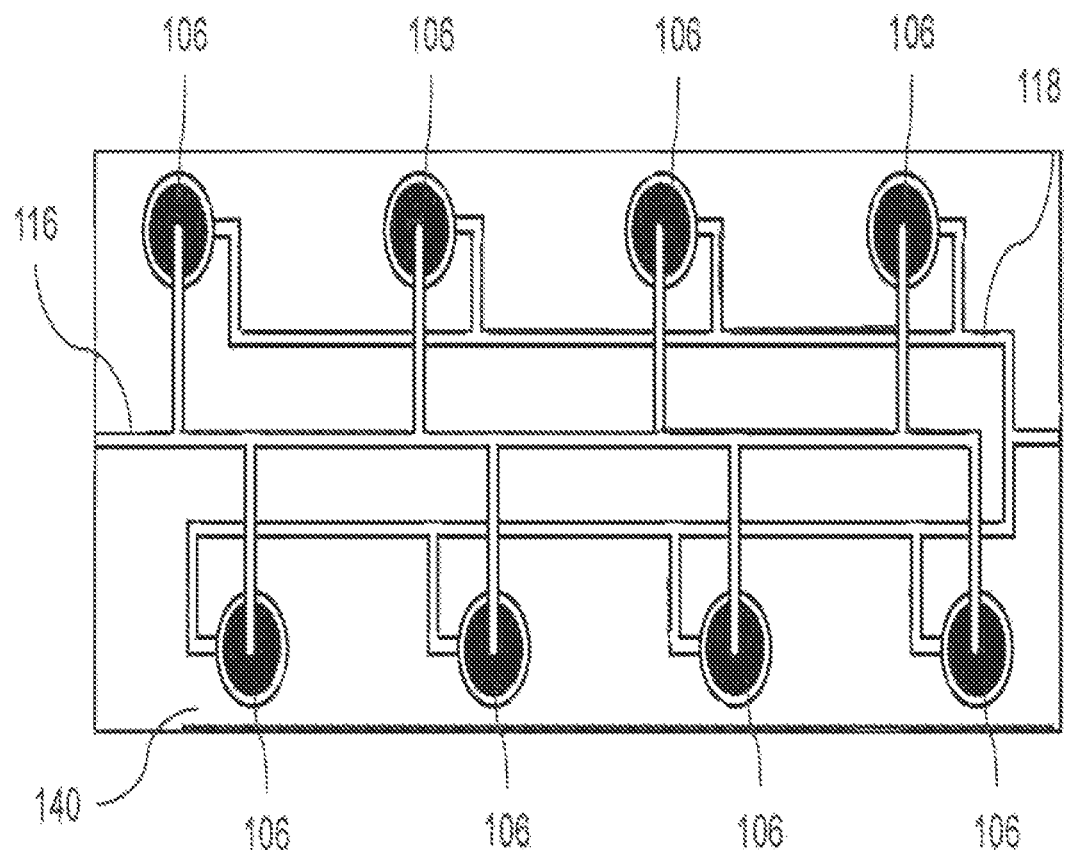
FIG. 7 is an overhead view of a fluidic cartridge similar to that of FIG. 3 comprising multiple sensors.

A multiplexed design for the fluidic cartridge is provided in FIG. 7. The inlet 116 is split and leads through several independent sensors 106, which are fluidically connected to the outlet 118. The sensors 106 are oriented to allow light transmission and spectrometric measurement. A multiplexed design can also be achieved using several fluidic microchannels coming from a single channel that carry the sample through different areas of the same membrane that have been functionalized for the same or different targets.

Multiplexed measurements can be taken with multiple light sources and spectrometers (or other light measurement mechanisms such as a photodetector), a multiplexed spectrometer such as a hyperspectral imager, or by moving the chip to align each sensor under a single light source using the chemical sensing system 100 shown in FIG. 1. The flow through a multiplexed fluidic cartridge may be controlled by a single pump 112, however, designs that employ multiple pumps or other components to facilitate flow may also be used.

Figure 8:
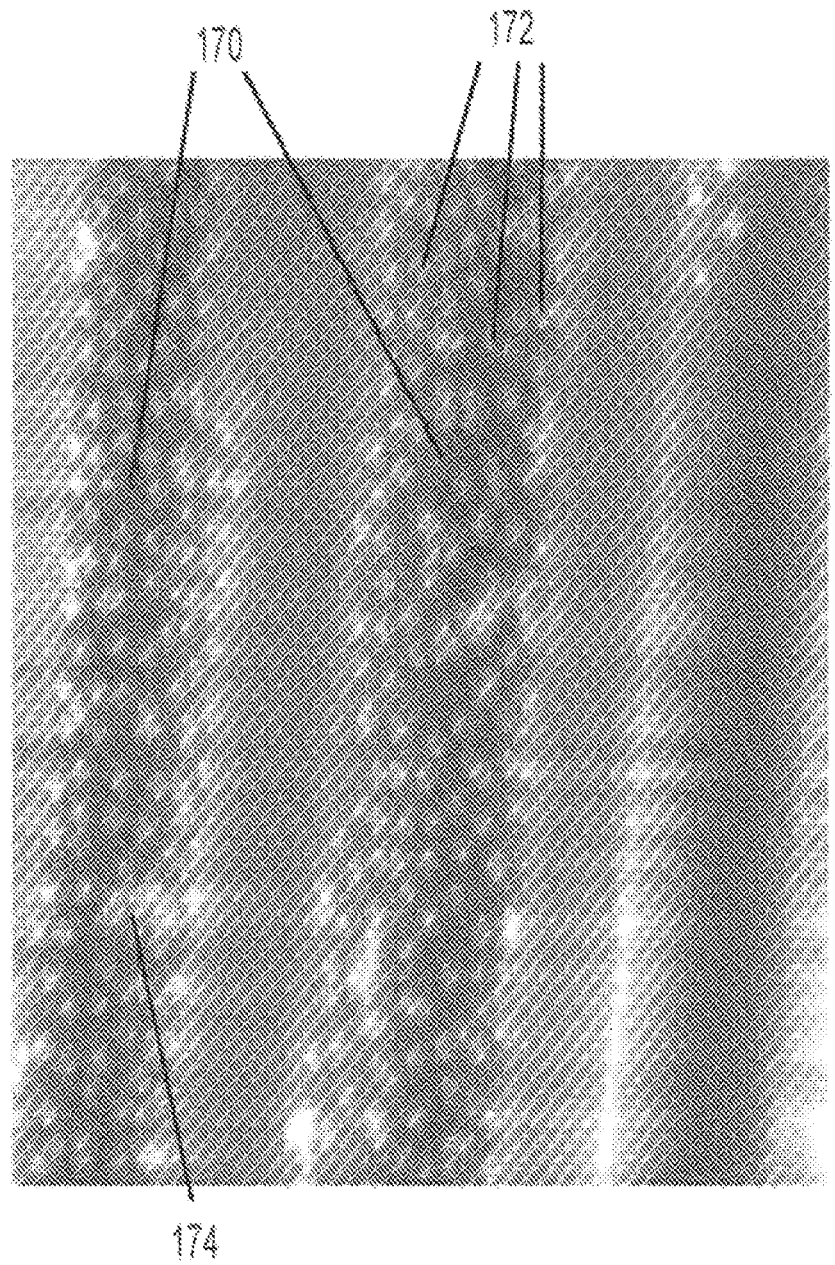
FIG. 8 is scanning electron microscope (SEM) image of 20 nm gold nanoparticles immobilized on an anodized aluminum oxide (AAO) membrane with a 200 nm pore diameter.

FIG. 8 is a scanning electron microscope (SEM) image of 20 nm gold nanoparticles 172 immobilized in the pores 170 of a 200 nm pore size AAO membrane. This figure demonstrates that the metal nanoparticles 172 may be immobilized throughout the pores 170 in a substantially dispersed manner. An agglomeration 174 is also shown on the surface of the pore 170 which may result if surface stabilizing additives are not employed.

Figures 9A, 9B:
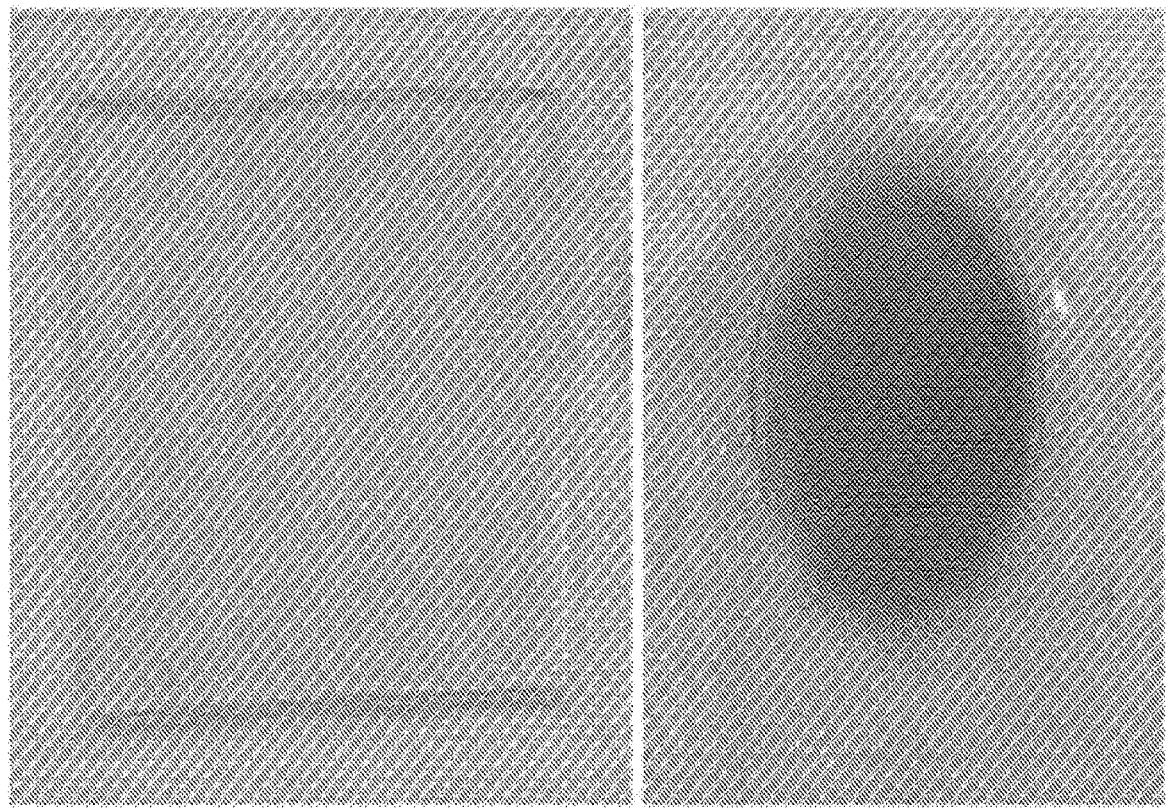
FIG. 9A is a photograph of gold nanoparticles (GNP) immobilized on a glass slide.
FIG. 9B is a photograph of gold nanoparticles immobilized on an AAO membrane.

FIGS. 9A and 9B, 10, 11, 16, 20, and 21 illustrate advantages of an example three-dimensional AAO membrane in comparison with conventional two-dimensional sensors. The glass slide of FIG. 9A comprises gold nanoparticles immobilized onto its surface. In contrast, the membrane of FIG. 9B is an AAO membrane comprising gold nanoparticles immobilized on the surface throughout its pores. The red appearance of both images is due to the LSPR of the immobilized gold nanoparticles. The AAO membrane appears as a very dark red in comparison to the glass slide due to the larger number of immobilized gold particles per given unit of sensor surface area. Therefore, for each given unit of surface area, there is a stronger LSPR interaction due to the greater number of immobilized nanoparticles.

Figure 10:
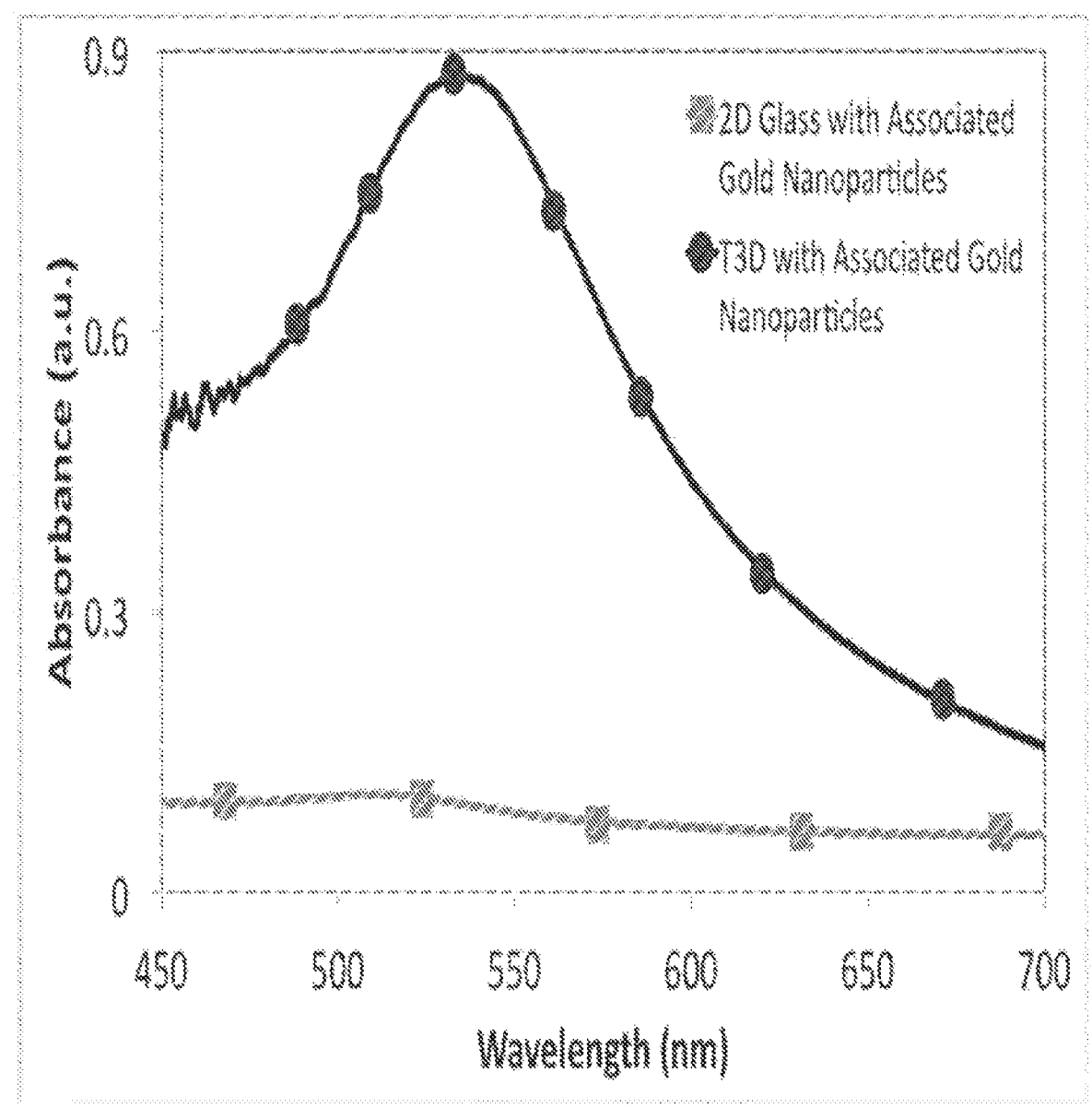
FIG. 10 is an example plot showing the relationship between absorbance and wavelength for an AAO membrane having gold nanoparticles immobilized in its pores with respect to a glass slide having gold nanoparticles immobilized on its surface.

FIG. 10 is a chart of the absorbance spectrums of the glass slide with respect to the AAO membrane of FIGS. 9A and 9B, respectively, taken in absorbance mode. The absorbance peak of the AAO membrane is approximately 6 times larger than the glass slide absorbance peak, which demonstrates that an AAO membrane may accommodate a higher number of gold nanoparticles, and therefore, may accommodate a higher number of accessible capture molecules with respect to a planar glass slide.

Figure 11:
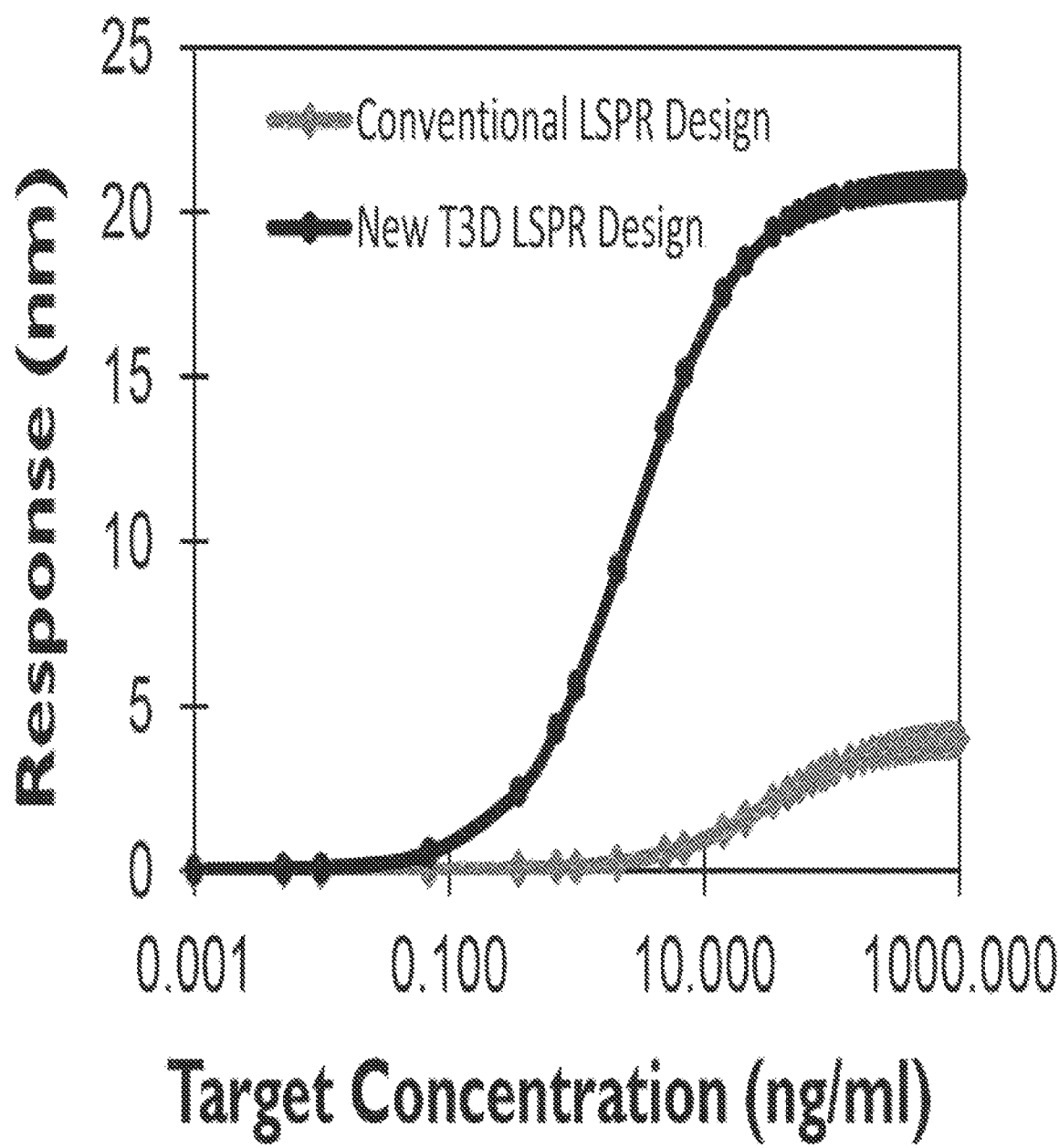
FIG. 11 is an example plot showing resonance peak shift with respect to target concentration in a solution.

FIG. 11 is a plot showing the simulated response of a sensor based on a glass slide (the conventional LSPR design) with respect to a sensor based on an AAO membrane, which may also be referred to herein as a transmissive three-dimensional (T3D) LSPR design (New T3D LSPR Design). Although not directly visible from the plot of FIG. 11, the detection limit of the sensor comprising the AAO membrane at (2 pg/ml) has been predicted by computer simulations to be improved by approximately 1000 times when compared with the 2D arrangement (2000 pg/ml).

Figure 12:
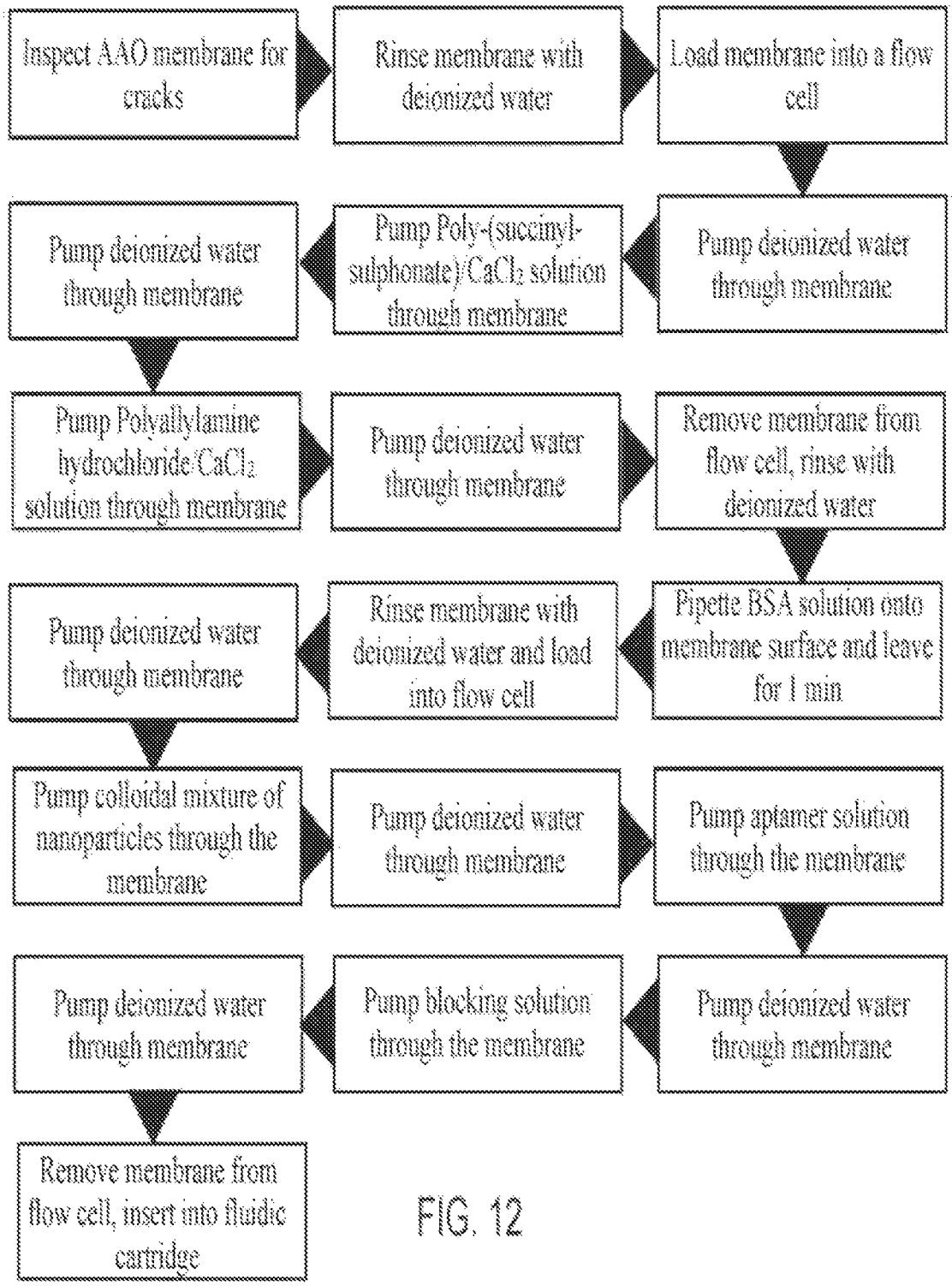
FIG. 12 is a process flow diagram of an example process for GNP immobilization on the pores of an AAO substrate and subsequent functionalization with capture molecules and blocking molecules.
Figure 13:
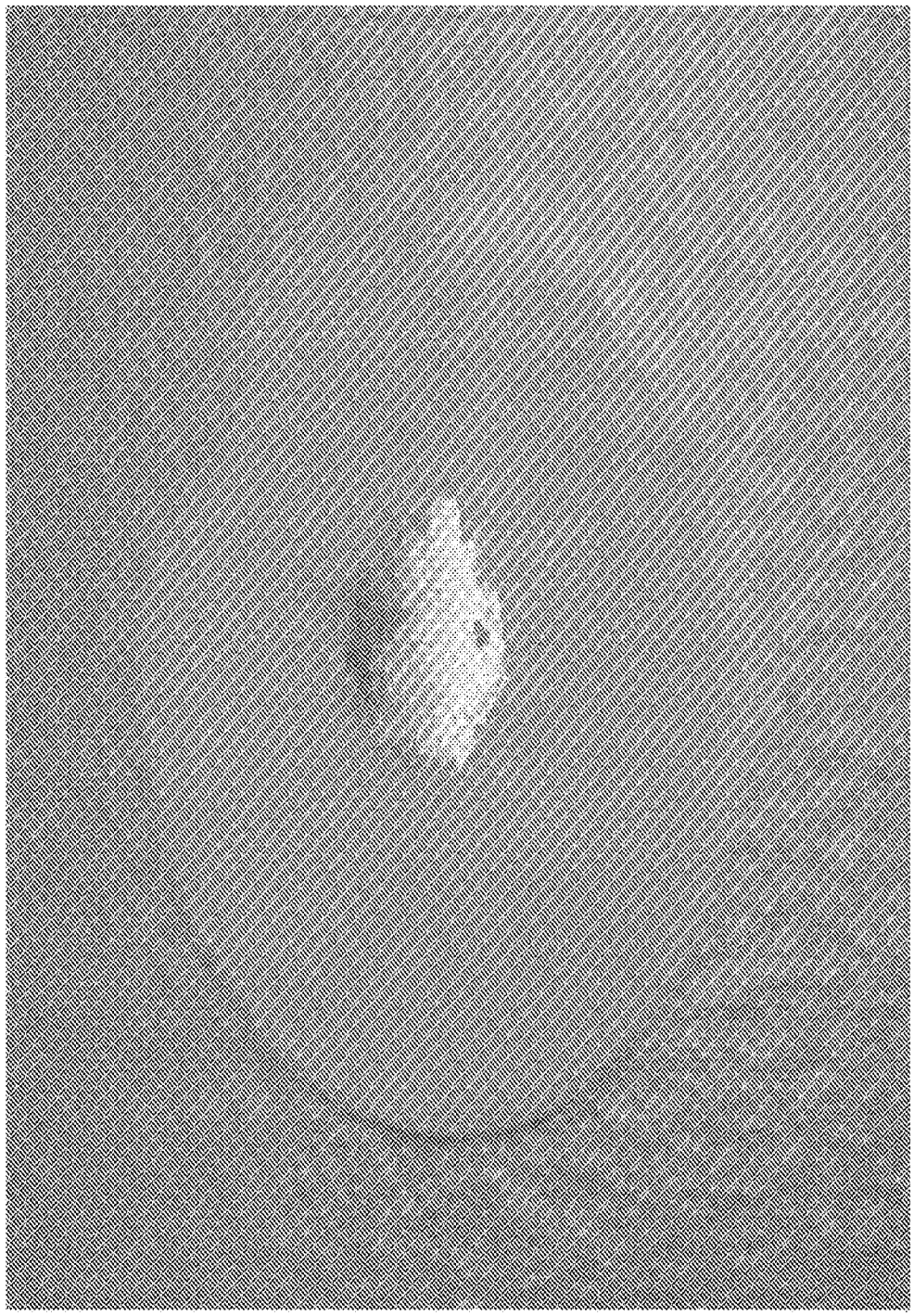
FIG. 13 is an image of AAO membrane with gold nanoparticles immobilized thereon without the use of BSA additive or coating.
Figure 14:
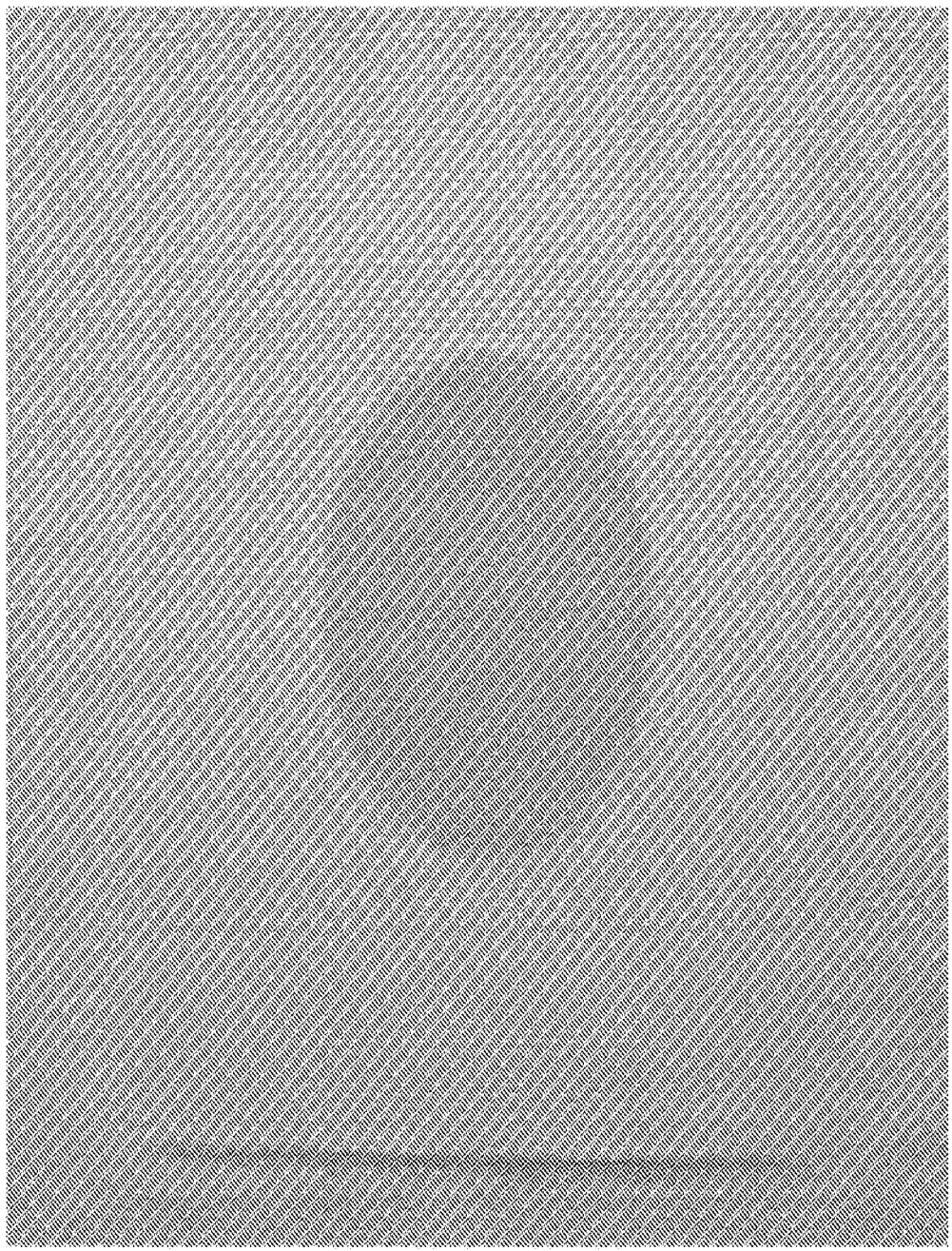
FIG. 14 is a photograph of a clean AAO membrane.

FIG. 12 is an example procedure for immobilizing gold nanoparticles on an AAO membrane. FIG. 13 shows the effect of immobilizing gold nanoparticles on a 13 mm AAO membrane without the use of surface stabilizing additives to prevent agglomeration. Agglomeration is particularly apparent on the outer surfaces of the membrane surface, i.e., the portions of the membrane between the pores. The gold nanoparticles agglomerate on the exterior surface of the membrane. The surface agglomeration makes the membrane ineffective. For reference, FIG. 14 is an example AAO membrane that has not been immobilized with gold nanoparticles. FIG. 14 may be compared with FIG. 9B to observe the differences between a clean AAO membrane and an AAO membrane with gold nanoparticles properly immobilized according to the procedure provided herein.

Figure 15:
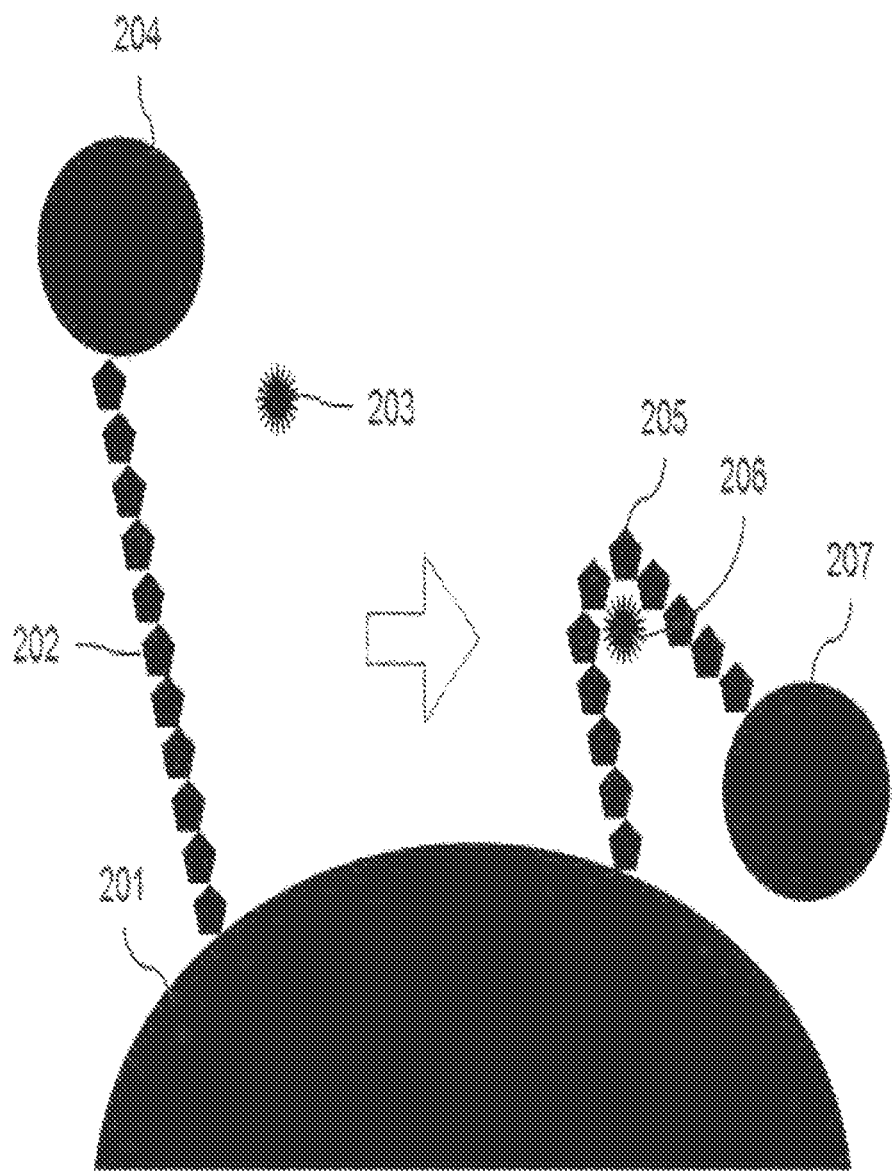
FIG. 15 is a diagram showing an example method to enhance the LSPR shift for small molecule targets.

Referring to FIG. 15, a method to enhance the LSPR shift for small molecule targets is outlined. For small molecular weight chemical target detection, for example ions or hormones, chemicals, DNA, RNA, aptamers or polymers 202 may not be effective without modification. However, a heavy molecule 204, such as a globular inert protein (bovine serum albumin), an inert heavy chained polymer or a surface inactivated small nanoparticle could be bound to the free end of the capture molecule 202 which may comprise, for example, an aptamer or capture polymer. When the target 203 comes into contact with the capture molecule 202, the capture molecule changes its conformation at 205, thereby bringing the heavy molecule 207 closer to the immobilized nanoparticle 201 surface. This enhances the LSPR effect that will be detectable by the spectrometer and allow for the detection of small chemical targets.

Another method of enhancing the LSPR signal for the detection of very small targets or targets at very low concentrations is the inclusion a signal-enhancing molecule that can be pumped into the mixture after target binding has taken place or mixed with the target prior to target binding. This is similar to the sandwich assay concept used in ELISA, where an immobilized antibody captures the target of interest and then a second molecular dye-labelled antibody is added to bind to the now immobilized target and signal its detection through fluorimetry. To adapt this concept to the sensor 106 as described herein, the sample fluid is pumped through the sensor and capture molecules on the nanoparticles bind the target chemicals. A secondary mixture of solution-based molecular dye labelled capture molecules are pumped through the sensor and bind to the captured targets. An energy transfer process occurs to enhance the LSPR effect due to the dye molecules being brought into close proximity with the metal nanoparticles. This may produce a larger absorption peak shift to be measured by the detector 110.

The incorporation of shift enhancers can also be used to improve the detection of chemicals. For example, a secondary capture molecules could be introduce to bind to the target after it has bound to the nanoparticle surface through the primary capture molecule. This would enhance the LSPR shift due to the enhanced localized change in the refractive index due to the additional mass. Another alternatives to potentially enhance the shift of the resonance peak is the addition of other enhancer entities, such as free-floating polymer or metal nanoparticles functionalized with secondary capture molecules, after the target chemicals are bound to the capture molecules in the sensor 106. Such entities would be made of materials with a high refractive index and molecular weight to allow a significant enhancement of the signal shift when they bind to the target. Metal particle enhancer entities could be made of an LSPR generating material to further enhance the resonance shift by resonance coupling. The entities could also be a magnetic material such as iron oxide, which has a very high refractive index and molecular weight. They could also be metal coated polymer particles, polymer coated metals particles, polymers particles, or metal particles.

Another method to enhance the performance of the LSPR sensor is to choose nanoparticle and pore sizes that cause the particles to be close enough together so that their three dimensional electromagnetic fields overlap. When this occurs, a single binding event on the surface of one nanoparticle will result in changes to its own electric field in addition to changes in the electromagnetic fields of those neighbouring nanoparticles close enough to have their fields overlap. This will result in a larger response from a single binding event, increasing the signal change.

In one embodiment of the invention there is provided a self-referencing sensor for simultaneously sensing analyte and reference signals. The reference signal can then be used to subtract out the non-specific effects observed in the detection signal obtained from the analyte.

In one embodiment the nanoparticles are supported on a substrate in another embodiment the nanoparticles are in a solution, suspension or dispersion.

In one embodiment, the invention is directed to a self-referencing sensor apparatus employing a sensor composed of at least one nanoparticle type that is capable of providing multiple signals simultaneously. Specifically, the nanoparticle type(s) are selected such that at least two distinct LSPR peaks are produced and can be measured by a single detector. The nanoparticles can be functionalized with a combination of various capture molecules and blocking molecules to provide both a specific detection signal as well as a reference signal simultaneously.

In one embodiment the self-referencing sensor comprises a first type of nanoparticle having a distinct LSPR signal functionalized to bind to an analyte and a second type of nanoparticle having a distinct LSPR signal that is different than the signal of the first type of nanoparticle. The second nanoparticle is functionalized to block binding with the analyte, thereby acting as a reference signal. A signal processor may then be used to subtract the reference signal from the analyte signal.

Figure 23:
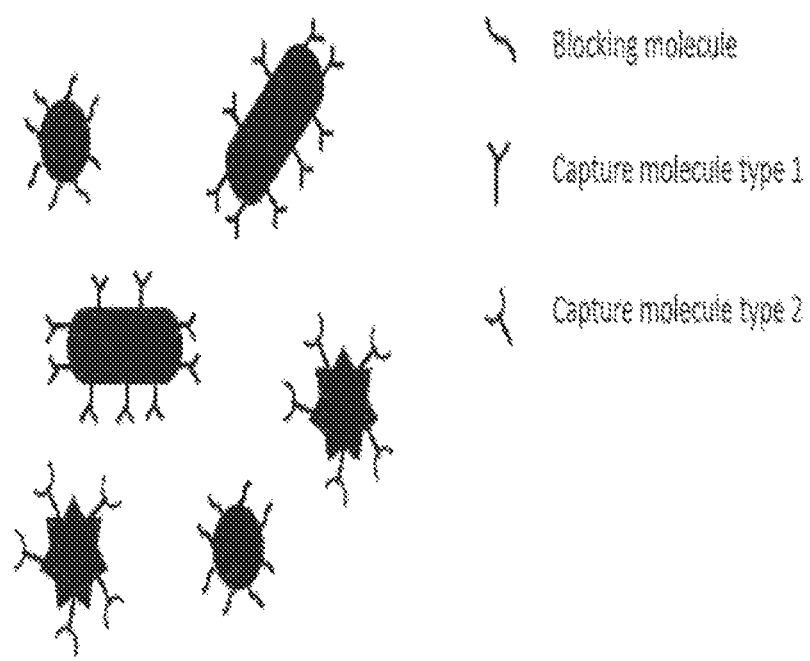
FIG. 23 is a schematic depicting a self-referencing sensor comprising nanoparticles in solution functionalized with capture molecules and blocking molecules.

Referring to FIG. 23, an example of a sensor containing nanoparticles in solution is shown. The sensor contains one or more nanoparticle types in a colloidal dispersion that would produce at least two distinct LSPR peaks. Each nanoparticle type can be non-functionalized, functionalized with capture molecules, functionalized with blocking molecules, or functionalized with a combination of any capture molecules and blocking molecules. At least one nanoparticle type must be able to specifically bind to an analyte of interest. In the example shown in FIG. 23, the sensor contains three nanoparticle types, each functionalized with a unique capture molecule or blocking molecule. The two nanoparticles with capture molecules would be capable of detecting two different types of free molecules through specific interactions, whereas the blocked nanoparticle would provide the reference signal.

Figure 24:
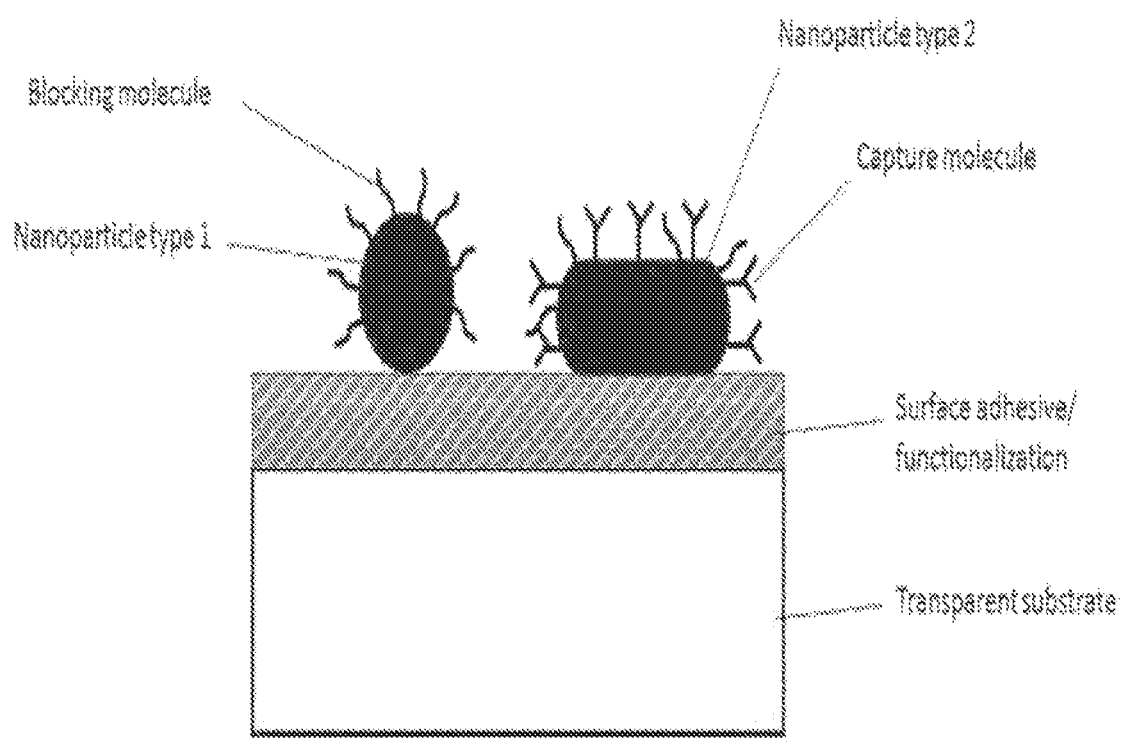
FIG. 24. Is a schematic depicting a self-referencing sensor comprising nanoparticles on a substrate surface containing one particle type functionalized with capture molecules and a second particle type functionalized with only blocking molecules.
Figure 25:
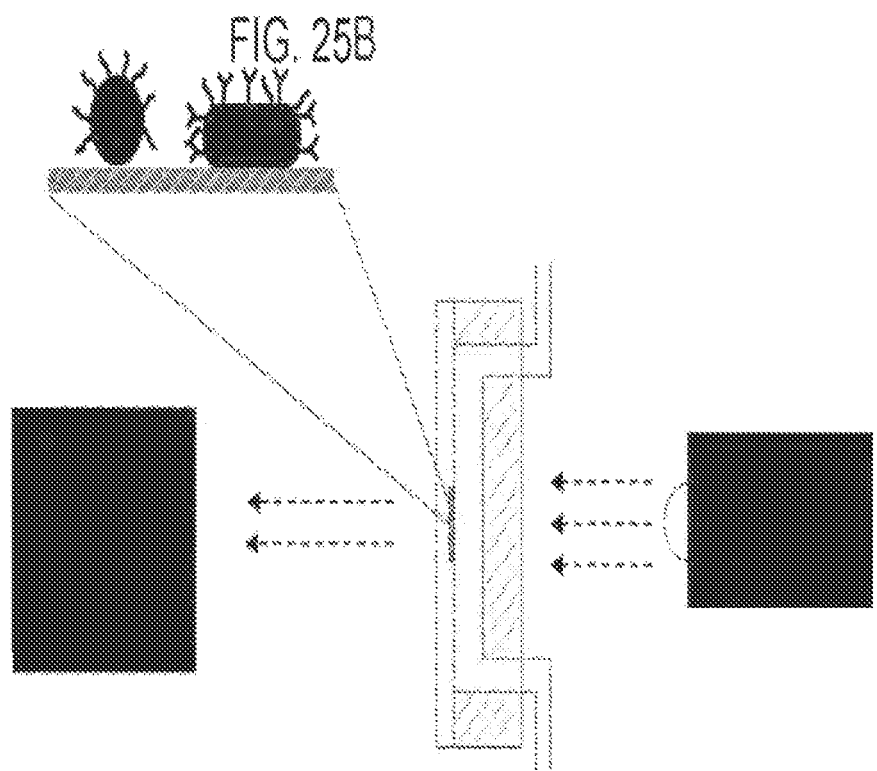
FIG. 25A is a cross-section top view of a self-referencing sensor apparatus setup.
FIG. 25B is a schematic depicting more than one nanoparticle type with different functionalization on the same substrate which may be interfaced with a fluidic channel between the LSPR light source and the detector.

Referring now to FIG. 24, an example of a sensor containing nanoparticles on a substrate is shown. The sensor may contain one or more nanoparticle types that are immobilized onto a substrate that would produce at least two distinct LSPR peaks. In FIG. 24 two nanoparticle types are shown, each nanoparticle type can be non-functionalized, functionalized with capture molecules, functionalized with blocking molecules, or functionalized with a combination of any capture molecules and blocking molecules. At least one nanoparticle type must be able to specifically bind to an analyte of interest. FIG. 24 shows a first nanoparticle type with blocking molecules and a second nanoparticle type with capture molecules and blocking molecules. In this example the first nanoparticle type would provide a reference signal and the second nanoparticle type acts as an analyte sensor.

When used in transmission mode, the sensor substrate will be at least partially transparent to allow for the light source to pass through the material and reach the detector such that the LSPR response of the nanoparticles can be measured. The substrate can be, but is not limited to, a planar surface such as glass, plastic, quartz, titania or silica-based materials, or can be a three-dimensional porous material such as anodized aluminum oxide.

The nanoparticles may be immobilized onto the substrate by direct deposition, or through the use of an adhesive layer on the surface or a surface functionalization as shown in FIG. 24. This includes but is not limited to immobilization through covalent bonds, electrostatic interactions, hydrophilic/hydrophobic interactions and/or Van der Waals forces between the nanoparticles and the surface. The nanoparticles can be deposited in a monolayer or multi-layer structure on a variety of surface morphologies. The nanoparticles can also be fabricated using top down processing methods such as nanoimprint lithography, UV lithography, or electron beam lithography.

Different nanoparticle types refer to nanoparticles that vary either in composition, size and/or shape. Typically metal nanoparticles are used to produce an LSPR signal. Compositions of metal nanoparticles that can be used for LSPR include but are not limited to gold, silver, platinum, copper, gold coated silver, silver coated gold, combinations of these metals, and combinations of metal-coated non-metal nanoparticles. Useful nanoparticle shapes include but are not limited to, rods, stars, urchins, decahedra, hexagons, triangles, shells, prisms, platelets, spheres, rice, plates, cubes, cages, stars and bipyramids. The dimensions of the nanoparticles can range between about 1 nm and 1000 nm with a variety of surface area to volume ratios.

The nanoparticles can be functionalized with capture molecules to provide specific detection of another molecule or chemical of interest (analyte). Capture molecules that can be used include but are not limited to chemical functional groups, aptamers, antibodies, DNA, nucleic acids, proteins, small molecules, or polymers. The surface of the nanoparticle may also act as capture molecules.

The nanoparticles can also be functionalized with blocking molecules. Blocking molecules are used to prevent nonspecific binding to the nanoparticle surface. They may often comprise thiolated compounds with inert end groups such as carboxyl, methyl, or polyethylene glycol (PEG) that provide aqueous stability. Bovine serum albumin (BSA) is another example of a possible blocking molecule that may be used on nanoparticles.

Nanoparticle types can be functionalized with both capture molecules and blocking molecules. In this situation, the blocking molecules are used to pacify empty binding locations on the nanoparticle surface, thus preventing unwanted nonspecific binding.

There are many methods to immobilize and functionalize multiple nanoparticle types to create the sensors. These methods include, but are not limited to: deposition of a colloidal mixture of multiple nanoparticle types in one step followed by selective or non-selective particle functionalization, functionalization of the nanoparticles in solution prior to one-step deposition, functionalization of the nanoparticles in solution followed by multi-step deposition, or multi-step deposition and functionalization of the nanoparticles. The use of such methods would be familiar to one of skill in the art.

Referring now to FIGS. 25A-B and FIG. 26A-C, showing the top view of an example of a self-referencing sensor systems. The system is provided in a transmission based measurement setup. The sensor system is composed of a light source, detector, and sensor which is interfaced with a fluidic cartridge. The fluidic cartridge comprises a fluid inlet, channel, and a fluid outlet to deliver and egress the sample fluid containing one or more target molecules to and from the sensor. The fluidic cartridge is composed of a material that is substantially optically transparent in the LSPR wavelengths being used. The fluid inlet is fluidically connected to the sensor and thereby operable to deliver fluid to the sensor to cause one or more target molecules in the sample fluid to bind to capture molecules in the sensor, as is further described herein.

In the example of FIG. 25A, a single sensor substrate is interfaced with the fluidic channel. The single substrate contains at least one type of nanoparticle, with at least one nanoparticle type being functionalized with a specific capture molecule. In the case where multiple nanoparticle types are used, the different nanoparticle types can be immobilized onto the same area of the substrate, or onto distinct areas of the substrate within the optical path. FIG. 25B is an expanded view of the substrate shown in FIG. 25A. The expanded view is a schematic depicting the substrates with two types of nanoparticles.

Figure 26:
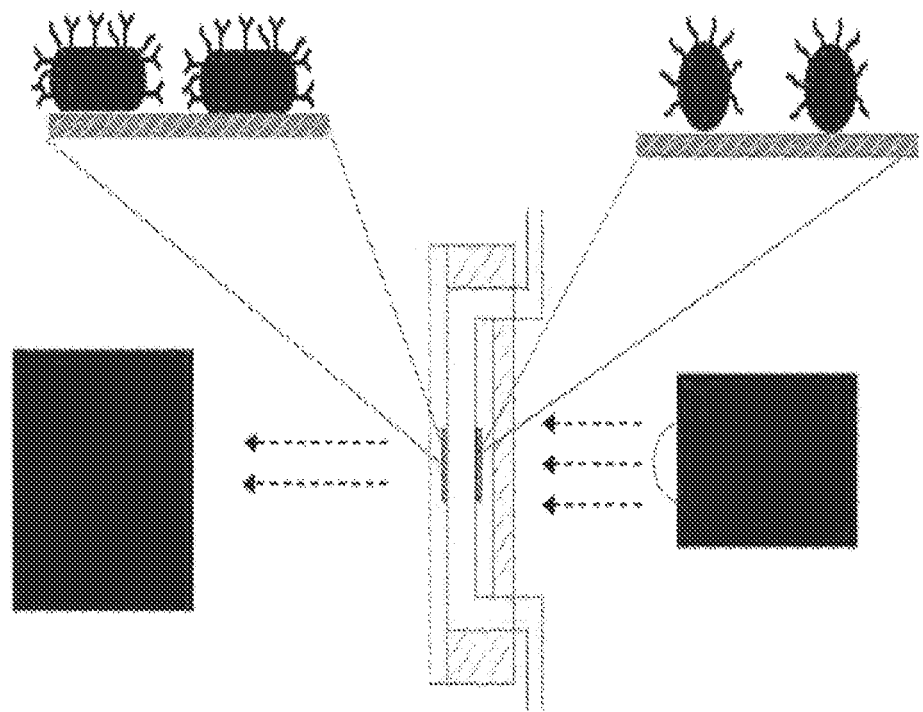

In the example of FIG. 26, multiple sensor substrates are interfaced with the fluidic channel and are located on the same optical path. Each substrate can contain one or more nanoparticle types immobilized onto the same or distinct areas. In the example depicted in FIGS. 26B and 26C, each substrate contains different nanoparticle types, one being functionalized with a combination of specific capture molecules and blocking molecules, while the other with blocking molecules only.

The above components described for a transmission based measurement apparatus can also apply for reflection based measurement apparatus, with the exception that the light source and the detector are located on the same side of the sample for a reflectance measurement.

Multiplexed designs of the self-referencing sensor systems mentioned herein are also possible. For example, in a multiplex design several independent sensors may be interfaced with one or several fluidic microchannels, or several fluidic channels may pass over different areas on the same sensor containing nanoparticles. Multiplexed measurements can be taken with multiple light sources and/or detectors.

To obtain two or more LSPR peaks, either a single nanoparticle type can be used or a combination of multiple nanoparticle types. The composition, size and shape of the nanoparticle type, effects the position and intensity of the LSPR absorbance peak(s). As such, the nanoparticle type, or combination of nanoparticle types, should be selected such that the LSPR peaks do not overlap to a degree that would prohibit distinction of the peaks. In one embodiment at least two distinct LSPR peaks having similar intensities, narrow full-width-half-maxima and minimal (or no) spectral overlap, are selected.

Figure 27:
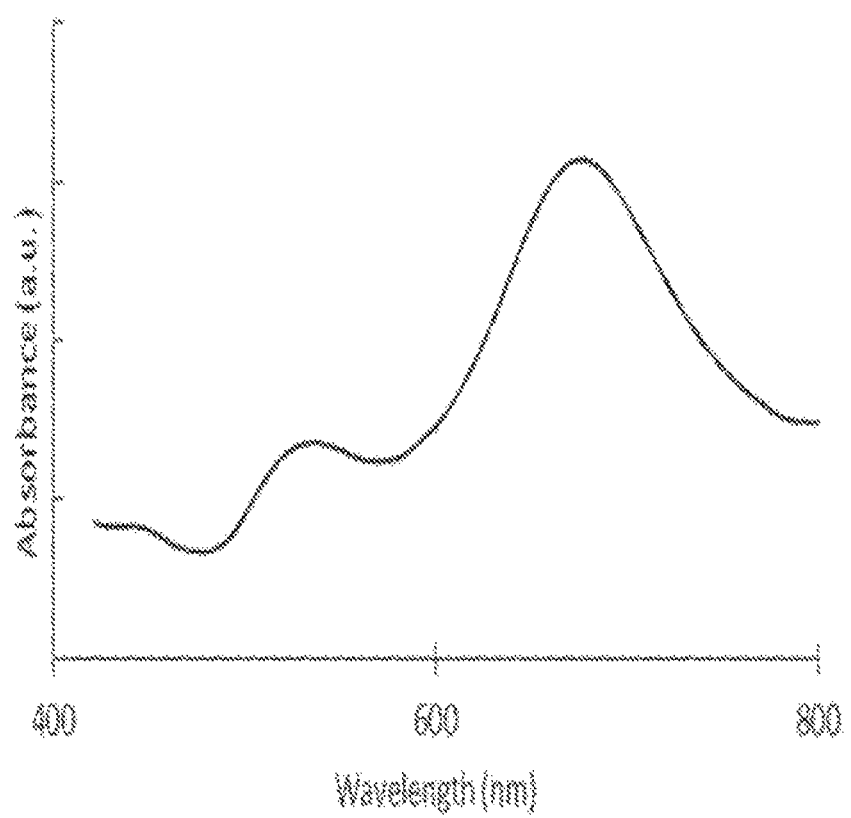
FIG. 27 is a graph showing the absorbance spectrum of a sensor containing a single particle type immobilized onto the substrate, which produces two distinct LSPR peaks.

Referring now to FIG. 27, an example absorbance spectrum of a single nanoparticle type immobilized onto a glass substrate is shown. This nanoparticle type produces two LSPR peaks due to the longitudinal and transverse resonant modes of the rod particle shape. The two peaks are distinct and can be individually tracked, therefore can be used for the sensor system.

Figure 28A:
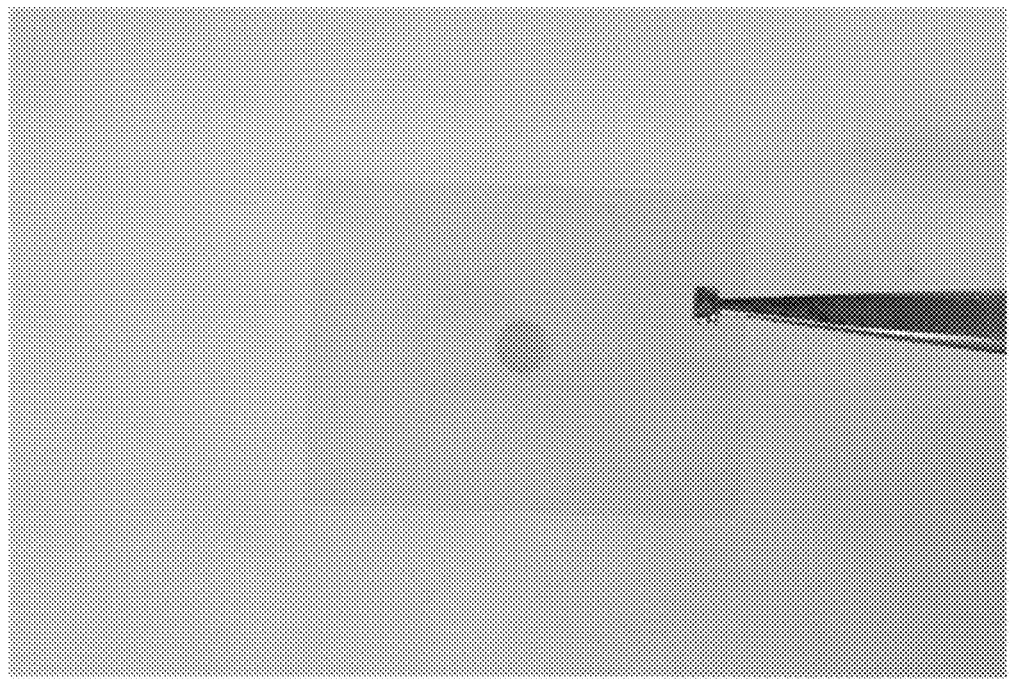
FIG. 28A is a photograph of a self-referencing sensor containing two types of nanoparticles immobilized within the same area on a glass substrate.
Figure 28B:
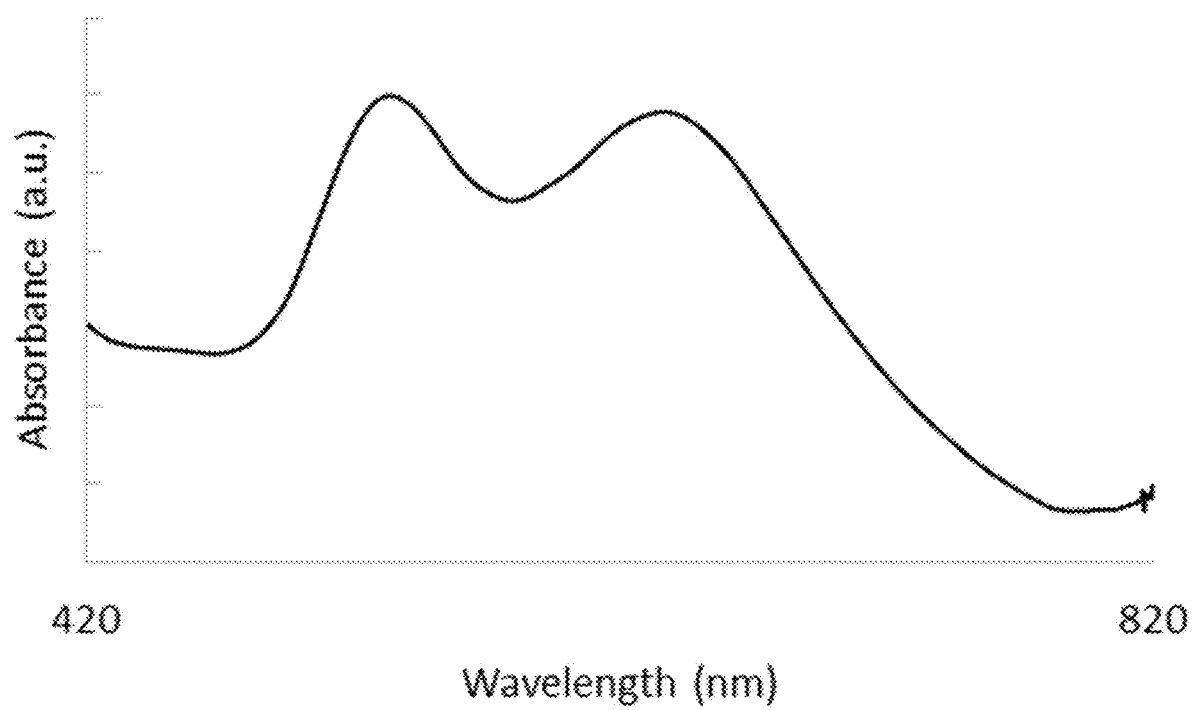
FIG. 28B is a graph showing the absorbance spectrum of the sensor of FIG. 28A containing two distinct LSPR peaks.

In FIG. 28A, a photograph of the sensor containing two nanoparticle types immobilized onto the same area of the glass substrate is shown. The resulting absorbance spectrum of the sensor is shown in FIG. 28B. The absorbance spectrum contains two distinct LSPR peaks, each of which is contributed from the different particle types. The two peaks are distinct and can be individually tracked and therefore can be used in a self-referencing sensor system.

The LSPR responses of the nanoparticles can be tracked by measuring the LSPR peak positions, peak intensities, the peak full-width-half-maximum (FWHM), peak shape, and/or any other property of the nanoparticles that are sensitive to the surrounding environment. A single measurement type, or a combination of any thereof can be used.

Figure 29:
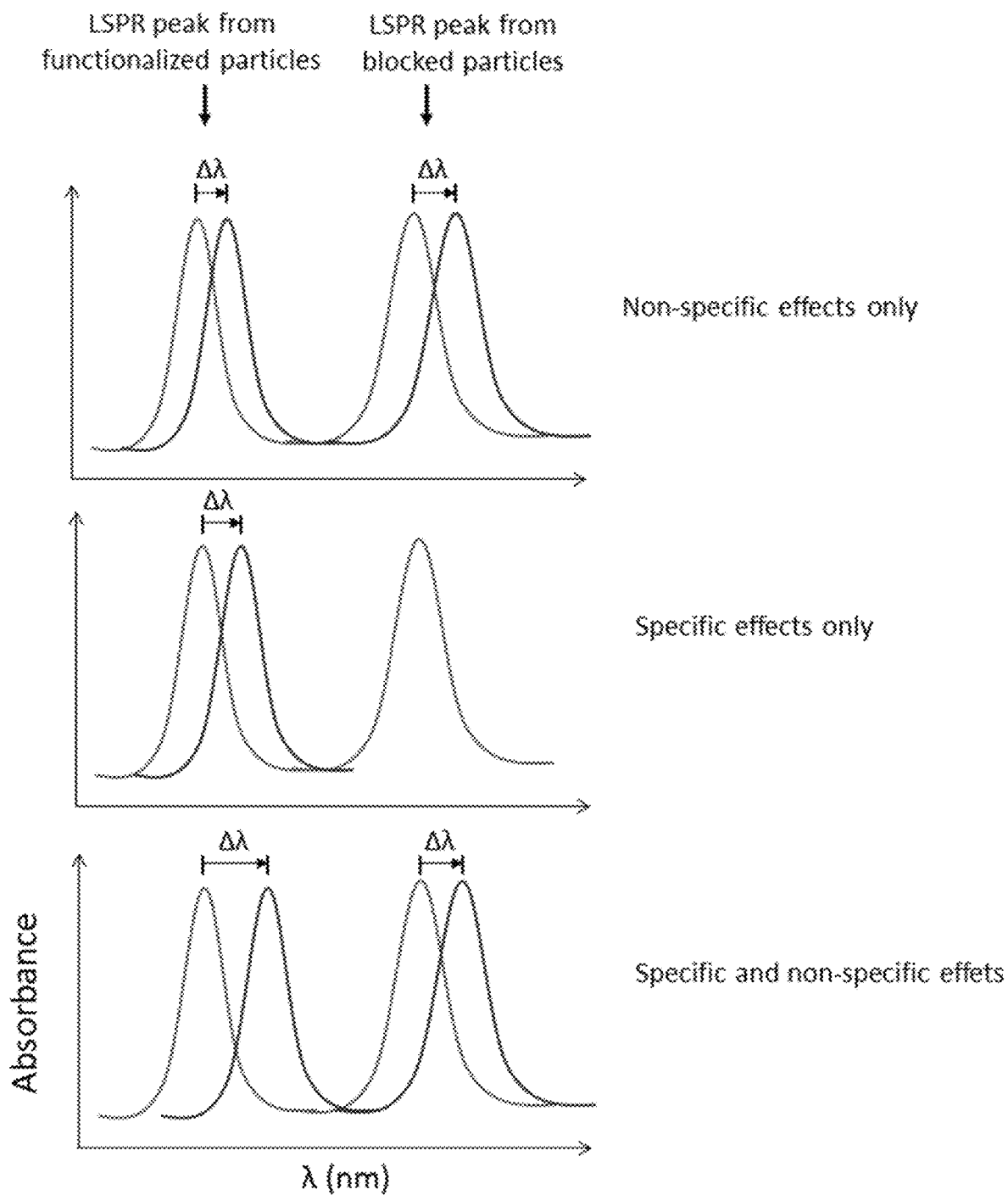
FIG. 29 is a series of graphs showing the resonance peak shifts observed with a self-referencing sensor with (top) detection of bulk effects, middle detection of specific molecule only, and (bottom) detection of specific molecule with bulk effects using a combination of two nanoparticle types, one functionalized with capture molecules and the other with blocking molecules.

In FIG. 29, a diagram outlining an example sensor response is provided. This example sensor system uses two nanoparticle types to produce the two distinct LSPR peaks as seen in the absorbance spectra. The nanoparticle type producing the LSPR peak at the shorter wavelength is functionalized with the specific capture molecule (the functionalized particles), whereas the second nanoparticle type producing the higher wavelength LSPR peak is functionalized with blocking molecules (the blocked particles). The LSPR response is being tracked by measuring the change in the LSPR peak positions. In the scenario where the sensor is detecting nonspecific effects only (top graph), a change in LSPR peak position is observed with both peaks as they are both susceptible to these events. In the scenario where the sensor is detecting specific binding effects only (middle graph), a change in LSPR peak position is only observed with the functionalized particles. If both specific binding effects and nonspecific effects are present simultaneously (bottom graph), both LSPR peak positions will change; the functionalized particles will see both the specific and non-specific binding events, whereas the blocked particles will only see the nonspecific binding events.

In one embodiment the self-referencing sensor may comprise a nanoparticle type functionalized with only blocking molecules used in combination with another nanoparticle type being functionalized with capture molecules. Using a self-referencing sensor of this type, it is possible to correct the specific binding signal to remove any contributing nonspecific effects. This is realized by subtracting the signal sensed by the blocked nanoparticle from the signal sensed from the nanoparticle functionalized with capture molecules. A calibration of the signals may have to be performed prior to signal correction to account for any differences in the sensitivities or other properties that may differ between the nanoparticle types.

In another embodiment, the self-referencing sensor includes the use of one or more nanoparticle types producing at least two distinct LSPR peaks, with all particle types being functionalized with the same capture molecules. In one example two or more different nanoparticle types functionalized with the same capture molecules may be used. In this case both particles will sense both the specific binding and nonspecific binding effects. The contributions of the specific binding and nonspecific binding effects on the sensor signal can then be separated using the LSPR sensing characteristic equations of each nanoparticle type. In another example the self-referencing sensor comprises a single nanoparticle type which produces at least two distinct LSPR peaks. Since each LSPR peak usually corresponds to different dimensions of the nanoparticle, each LSPR peak has its own characteristic equation, which together can be used to separate the specific binding and bulk effects.

Although examples are provided with reference to LSPR detection techniques, the above may also be adapted to other spectrometric detection assays, for example, ELISA.

EXAMPLES

Example 1: Comparison of 2D Design to T3D Design

Figure 20:
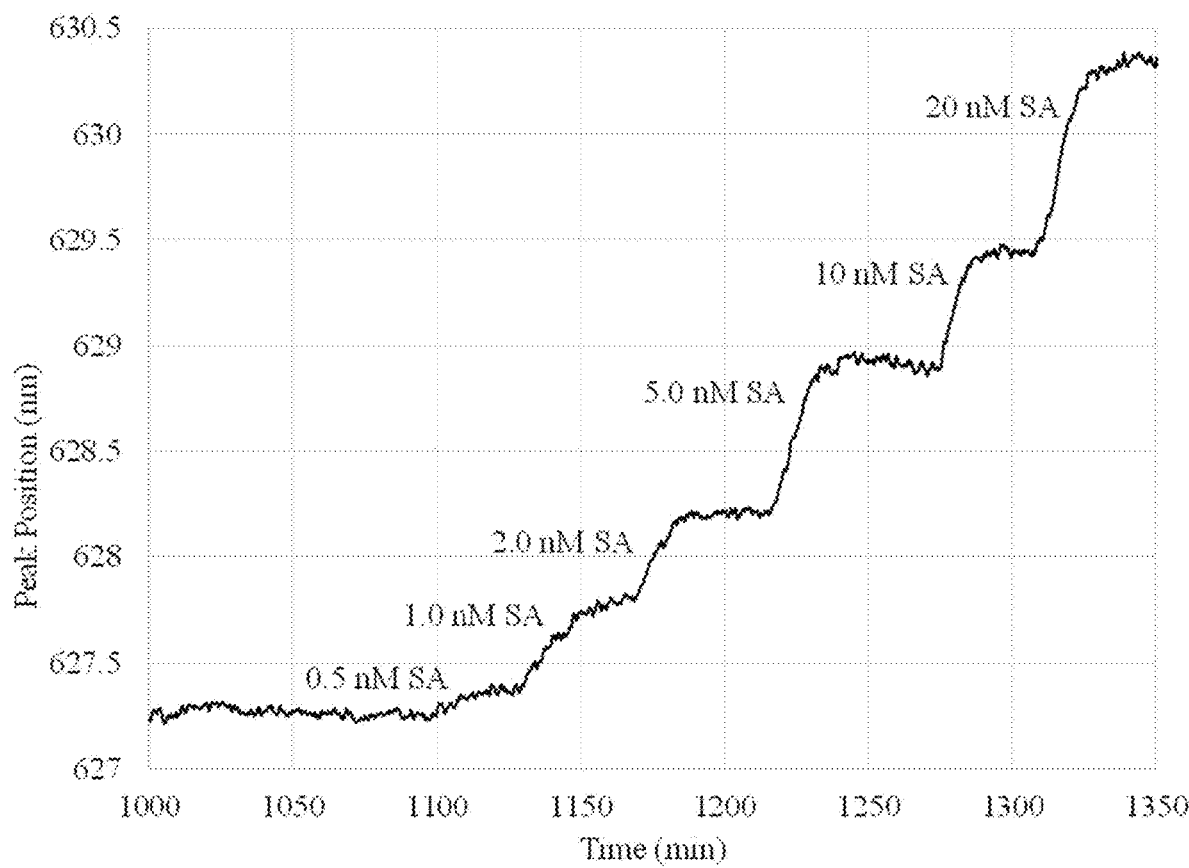
FIG. 20 shows the response of the T3D sensor to serial injections of the streptavidin (SA) protein, from 0.5 nM to 20 nM. The streptavidin binds to the biotinylated surface of the nanoparticles inside the AAO membrane.
Figure 21:
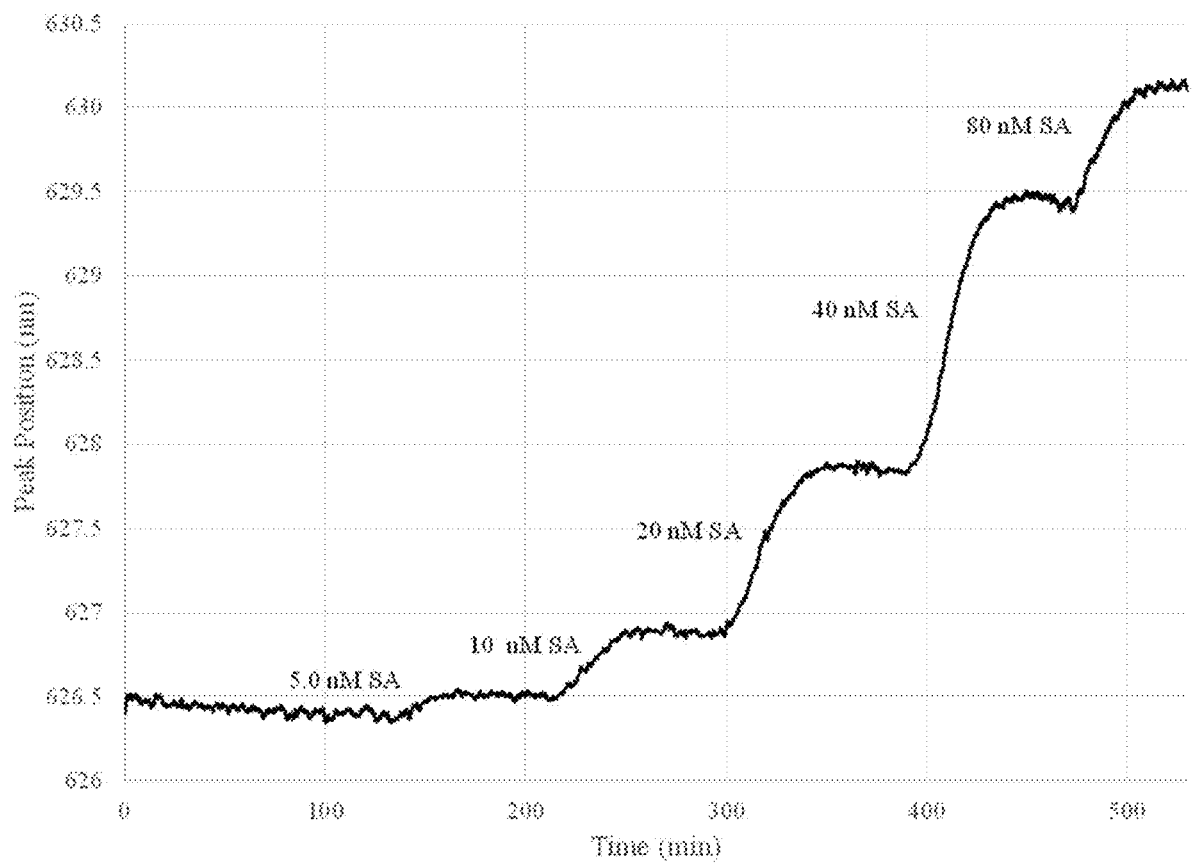
FIG. 21 shows the response of the conventional 2D sensor to serial injections of the streptavidin (SA) protein, from 5 nM to 80 nM. The streptavidin binds to the biotinylated surface of the nanoparticles which are immobilized onto a glass surface.

An example of the improvements offered by the T3D design versus the traditional 2D design is shown by comparison of FIG. 20 and FIG. 21. FIG. 20 shows serial additions of the protein streptavidin into an AAO membrane with 150 nm pores and 50 μm thick. Nanoparticles are immobilized in the pores and have an LSPR peak around 627 nm. The nanoparticles are functionalized with a biotin capture layer, with biotin being chemically bound to the nanoparticles via a thiol bond. The non-specific sites are blocked with PEG. The sensor shows a response at 0.5 nM streptavidin up to 20 nM in this case. 200 μL of streptavidin is introduced at 20 μL/min. The detection limit is approximately 0.5 nM for this system. Serial additions of streptavidin are made over a glass substrate with the same nanoparticles immobilized on the surface of the glass. Biotin is attached to the surface of the nanoparticles using the same chemistry as the T3D sensor. Streptavidin is injected serially at 20 μL/min in volumes of 200 μL. The sensor shows a response at 5.0 nM up to 80 nM in this case. The detection limit is approximately 5.0 nM. This demonstrates that the T3D sensor exhibits a 10× improvement in detection limit over the traditional 2D sensor, in this example case.

Example 2: Test Protocol for Fibronectin LSPR Sensor Testing

Preparation Steps
Buffer Preparation ("Tris")
Buffer: 20 mM Tris, 100 mM NaCl, 0.005% Tween20, in nuclease free water, pH 7.4
1. Autoclave glassware and pipette tips (200 μL and 1000 μL) to ensure nuclease free conditions.
2. For a 500 mL mixture weigh: 1.21 g Tris, 2.92 g NaCl and 0.025 g Tween 20 dissolve into 500 mL of $dH_2O$ then measure the pH of the solution. Adjust the pH up or down to 7.4 using a NaOH or HCl solution.
3. Store in a sealed container at 4° C.

Fibronectin Protein Preparation
Stock: 0.5 mg/ml already dissolved in buffer
1. Aliquot into 54 μL volumes at 0.5 mg/ml in Tris Buffer (Aliquot concentration=1.14 μM)
2. Stored in −20° C. Freezer BSA Preparation
1. Take 10.5 mg BSA, add to 2 ml vial, add 1 ml Tris buffer. This gives a 1% BSA solution. For a 0.1% solution add 70 uL of 1% BSA to 630 uL Tris buffer.
2. Store in a sealed container at 4° C.

Fibronectin Aptamer Preparation
Stock: 0.2 umol lypholized aptamer powder
1. Add 2 ml of Tris buffer to dry aptamer (makes 0.1 mM stock concentration).
2. Aliquot into 50 uL vials at 0.1 mM.
3. Stored at −20° C.

Functionalization and Testing Procedure
1. Thaw one aptamer aliquot to room temperature. Add 430 µL of Tris buffer to the aptamer aliquot to obtain a final concentration of 10 µM (once the 20 µL of TCEP is added in the next step). Vortex for 30 seconds to mix.
2. Make 2 ml of 40 mM stock TCEP by adding 20 mg TCEP to 2 ml of Tris buffer and mixing well. From this stock add 20 µL to the aptamer vial to give a final volume of 500 µL. Vortex for 30. Leave at room temperature for 2 hours.
3. Fill up a 20 ml beaker with water and place on the hot plate set at 90° C. Place the aptamer vial into the water bath for 3.5 minutes. Allow the aptamer to cool to room temperature.
4. Connect the T3D sensor and flow cell to the flow injection analysis system which consists of a 6 port injection valve, sample loop, and syringe pump. Set the pump speed to pump Tris buffer at 0.01 ml/min. Load 500 µL of aptamer solution into a 1 mL syringe ensuring no bubbles are present. Load the aptamer into a 500 µL sample loop and inject the solution via the injection valve. The interaction time between the gold nanoparticles and the aptamer will be approximately 50 minutes.
5. Once the solution has been fully pumped through the flow cell, pump fresh Tris buffer through the system for 30 minutes.
6. Turn the injection valve back to "load", and rinse out the sample loop using Tris buffer. Use a 1 ml syringe and load 500 µL of 0.1% BSA into the sample loop. Inject at a pumping speed of 0.01 ml/min.
7. Once the solution has been fully pumped through the flow cell (after 50 minutes hour), pump fresh buffer through the system for 30 minutes.
8. Disconnect the flow cell from the flow injection analysis system and remove the T3D sensor. Dry the sensor gently with nitrogen gas. If storing, store in a sealed container back filled with nitrogen.
9. Load the dry T3D sensor into the testing flow cell. Insert the flow cell into the reader unit and fill the cell with Tris buffer. Begin acquiring optical transmission spectra and begin tracking the LSPR peak position using the software. Acquire a baseline peak position in Tris buffer.
10. Add 550 µL of Tris buffer to a Fibronectin protein aliquot. This gives a Fibronectin concentration of 0.1 µM. Use a 1 ml syringe and load 200 µL of the Fibronectin sample into the inlet port of the flow cell. Activate the pump at 0.01 ml/min. The protein sample will pump through the membrane interact with the aptamer functionalized surface for 20 minutes.
11. Once the solution has been fully pumped through, acquire another peak baseline in Tris. Find the difference between the peak baseline from before and after the test. Using this value and the standard curve of concentration vs. peak shift, find the experimentally determine concentration of Fibronectin in the sample.
12. Dispose of the sensor and flow cell.

Example 3: Test Protocol for Streptavidin LSPR Sensor Testing

Functionalization and Testing Procedure

Pump 10 mM 11-MUA (11-mercaptoundecanoic acid) and 1-OT (1-octanethiol) mixture (in a 3:1 ratio) in ethanol through the flow cell for 60 minutes at 0.01 ml/min.

Pump 13 mM PBS (phosphate buffered saline) through the flow cell for 30 minutes at 0.1 ml/min.

Pump a 5 mM EDC/NHS solution through the flow cell for 60 minutes at 0.01 ml/min.

Rinse with PBS for 30 minutes at 0.1 ml/min.

Pump 1 mM of Amine-PEG3-Biotin in 13 mM PBS at pH 6.5 at 0.01 ml/min for 50 minutes. (PEG—polyethylene glycol)

Rinse with 13 mM PBS at 0.1 ml/min for 30 minutes.

Pump 500 µL of 25 µM low molecular weight PEG at 0.01 ml/min.

Pump 13 mM PBS through the flow cell for 30 minutes at 0.1 ml/min.

Disconnect the flow cell from the flow injection analysis system and remove the T3D sensor. Dry the sensor gently with nitrogen gas. If storing, store in a sealed container back filled with nitrogen.

Load the dry T3D sensor into the testing flow cell. Insert the flow cell into the reader unit and fill the cell with PBS buffer. Begin acquiring optical transmission spectra and begin tracking the LSPR peak position using the software. Acquire a baseline peak position in buffer.

Load 200 µL of the streptavidin sample at 10 nM in PBS into the inlet port of the flow cell. Activate the pump at 0.01 ml/min. The protein sample will pump through the membrane interact with the functionalized surface for 20 minutes.

Once the solution has been fully pumped through, acquire another peak baseline in buffer. Find the difference between the peak baseline from before and after the test. Using this value and the standard curve of concentration vs. peak shift, find the experimentally determine concentration of streptavidin in the sample.

Dispose of the sensor and flow cell.

Example 4: Immobilization of Gold Nanoparticles into AAO Membrane Pores Procedure Take AAO membrane from storage, inspect for cracks, chips or weak points Rinse AAO membrane with deionized $H_2O$ ($dH_2O$)

Load AAO membrane into flow cell and attach syringe connected to syringe pump

Pump 3 mL of $dH_2O$ through the membrane at 0.1 mL/min

Pump 2 mL of 2 µM poly-(succinyl-sulphonate)/0.4 µM $CaCl_2$) solution at pH 3.1 through the membrane at 0.1 mL/min Pump 6 mL of $dH_2O$ through the membrane at 0.1 mL/min Pump 2 mL of 2 µM polyallylamine hydrochloride/0.4 µM $CaCl_2$) solution at pH 3.1 through the membrane at 0.1 mL/min Pump 6 mL of $dH_2O$ through the membrane at 0.1 mL/min Remove membrane from flow cell, examine for cracks and rinse surface with $dH_2O$ Pipette 0.01% w/v bovine serum albumin solution onto the surface of the AAO membrane, leave for 1 minute then rinse with $dH_2O$ Load AAO membrane into flow cell in reverse orientation as previous and attach syringe connected to syringe pump Pump 3 mL of $dH_2O$ through the membrane at 0.1 mL/min Pump 10 mL of 0.1 nM gold nanoparticle mixture through the membrane at 0.05 mL/min Pump 6 mL of $dH_2O$ through the membrane at 0.1 mL/min If imaging: remove membrane from the flow cell, rinse with dH₂O If testing: keep in flow cell and proceed to capture probe functionalization steps. Connect flow cell to flow injection analysis system.

Although examples are provided with reference to LSPR detection techniques, the above may also be adapted to other spectrometric detection assays, for example, ELISA.

Example 5: Self-Referencing Sensor Two-Nanoparticle System, One Particle Functionalized with Capture Molecule, the Other with Blocking Molecule (Streptavidin Detection)

Figure 30:
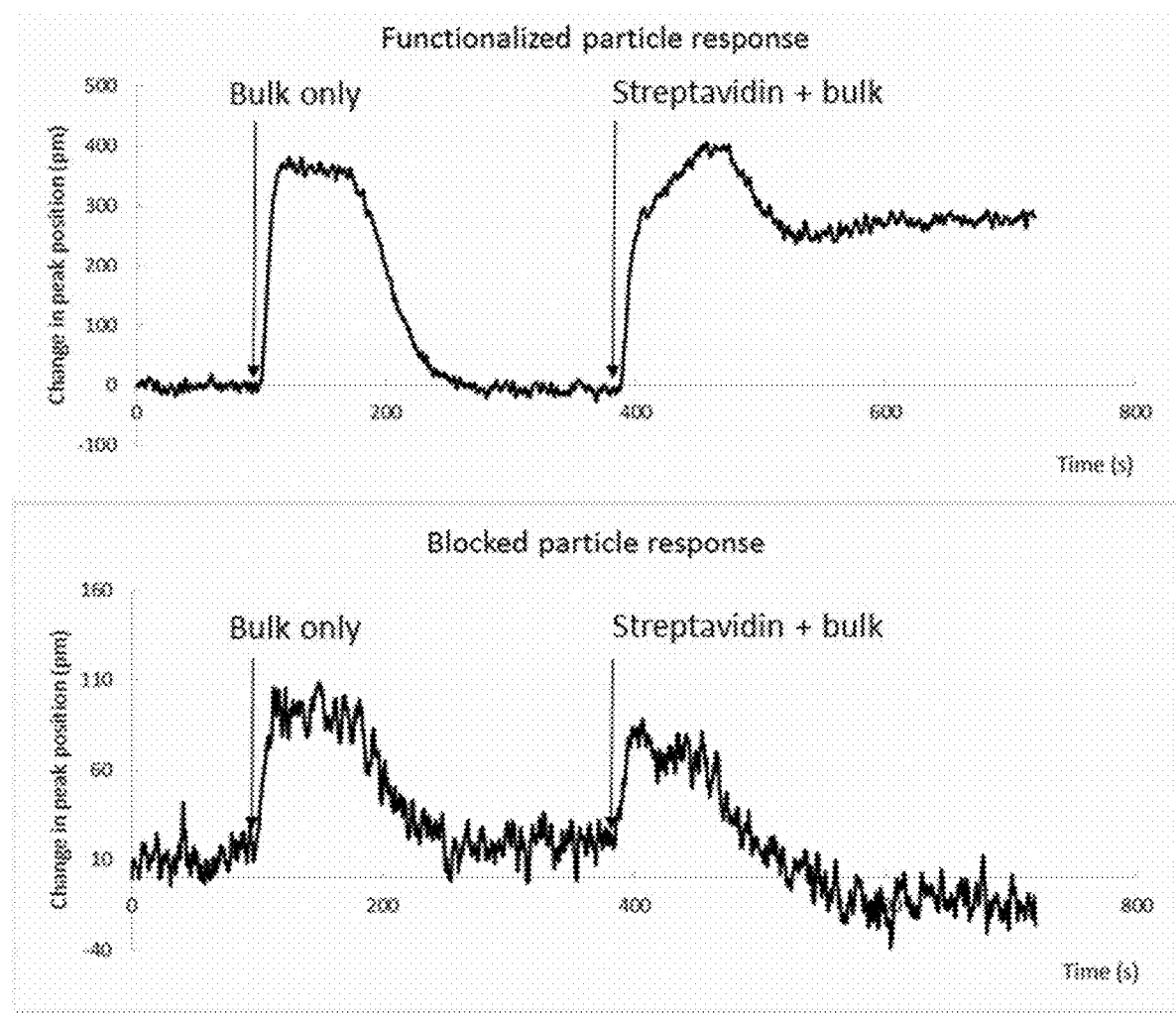
FIG. 30 is a series of graphs showing experimental results of resonant peak shifts observed when tracking both functionalized and blocked particles of a two nanoparticle type self-referencing sensor.

FIG. 30 presents experimental data taken from a self-referencing sensor apparatus as described herein, using a sensor comprising two different types of nanoparticles immobilized onto a glass substrate. The two nanoparticle types included gold spheres with a diameter of 40 nm and gold NanoUrchins with a diameter of 90 nm, with optical properties of LSPR peak wavelengths around 530 nm and 630 nm respectively. Both nanoparticle types were immobilized onto the same area of the glass substrate as shown in FIG. 28A, and produced two LSPR peaks at 536 nm and 635 nm as shown in FIG. 28B. The LSPR peaks were distinct with some spectral overlap, and could be individually tracked to monitor the LSPR sensing properties of each particle type. The 90 nm NanoUrchins were functionalized with a thiol-containing Biotin capture molecule (functionalized particle) to act as the specific sensing particle. The 40 nm spheres were functionalized with a dithiolalkanearomatic-PEG3-OH blocking molecule (blocked particle). The experiment was carried out using an LSPR apparatus in transmission mode similar to that described in FIG. 25. As a running buffer, 1x phosphate buffered saline (PBS) at pH 7.4 with 0.05% Tween20 and 0.1% BSA was used. Streptavidin at a concentration of 3 nM diluted in running buffer was used as the analyte, and 1.5% glycerol (w/w) in running buffer was used to produce nonspecific bulk refractive index shifts. To measure the LSPR sensing response of the nanoparticles, both peak positions were simultaneously measured and recorded over time. First, the glycerol solution was exposed to the surface for approximately 100 seconds, followed by introduction of the same glycerol solution containing streptavidin for the same amount of time. Upon the introduction of just the glycerol solution (bulk only), a similar shape of response is seen for both nanoparticle types. When exposed to the streptavidin-glycerol solution (streptavidin+bulk), the response of the functionalized particle showed a permanent peak shift indicating streptavidin binding with an apparent distortion of the binding curve due to the glycerol bulk. The response of the blocked particle however remained the same for that of the bulk only, thus providing a reference signal for the nonspecific component of the glycerol-streptavidin mixture.

Figure 31:
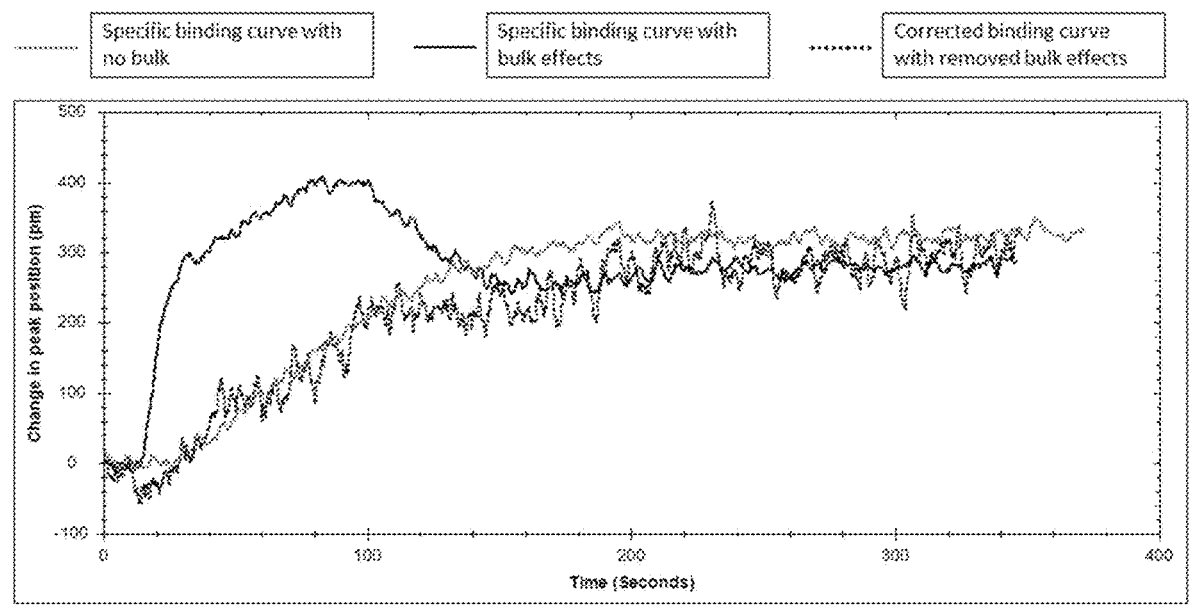
FIG. 31 is a graph showing experimental results demonstrating the ability to correct a specific binding curve that has been convoluted with bulk effects with a self-referencing sensor.

FIG. 31 contains the experimental raw and corrected biotin-streptavidin binding curves from the data presented in FIG. 30. The initial curve (black-solid) contains an obvious bulk distortion compared to the bulk-free reference curve shape (grey). The signal from the blocked particle was used as the reference as it measured only the nonspecific effects. As the sensitivities of both particle types used were different, the reference signal was calibrated to that of the detection signal by normalizing the sensitivity of the blocked particle to that of the functionalized particle. Using the calibrated reference signal provided by the blocked nanoparticle, the bulk effects were able to be subtracted and effectively removed from the distorted signal (black-dashed), resulting in a binding curve similar to that of the reference.

Example 6: Self-Referencing Sensor Two-Nanoparticle System, One Particle Functionalized with Capture Molecule, the Other with Blocking Molecule (His-Tagged Molecule Detection)

Figure 34A:
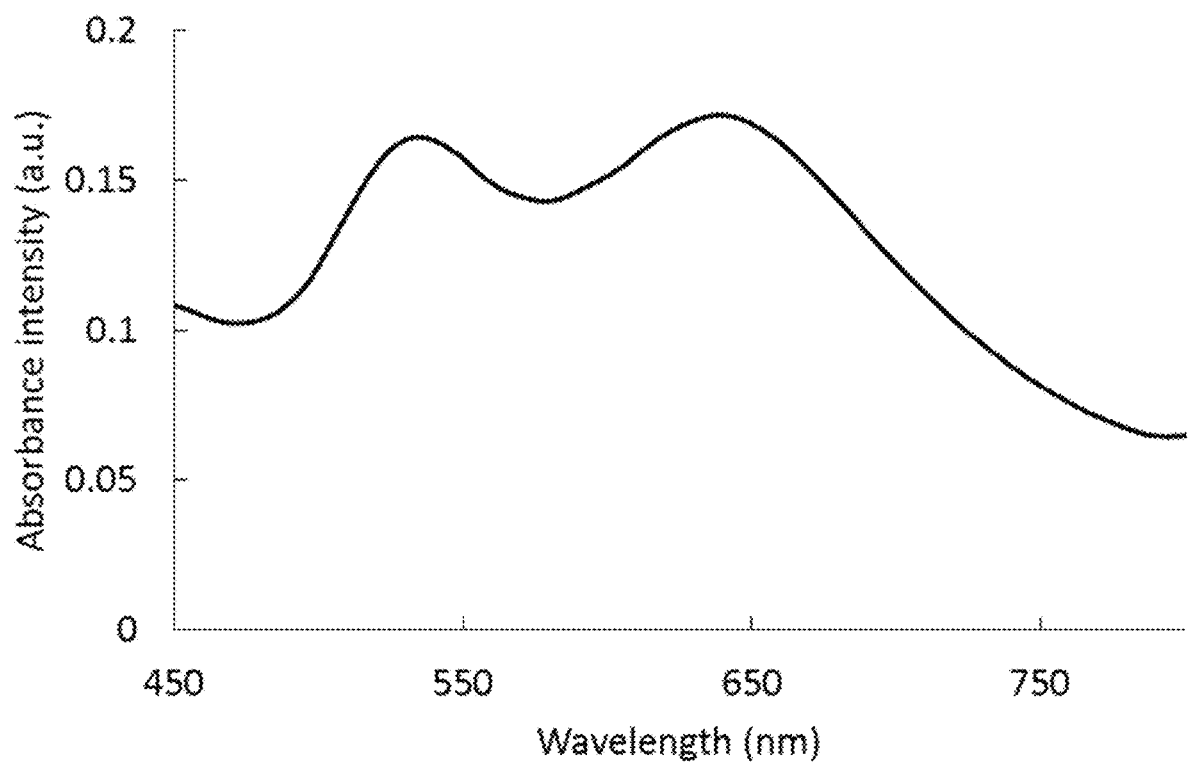
FIG. 34A is a graph of an absorbance spectrum showing two LSPR peaks of a two nanoparticle type self referencing sensor.
Figure 34B:
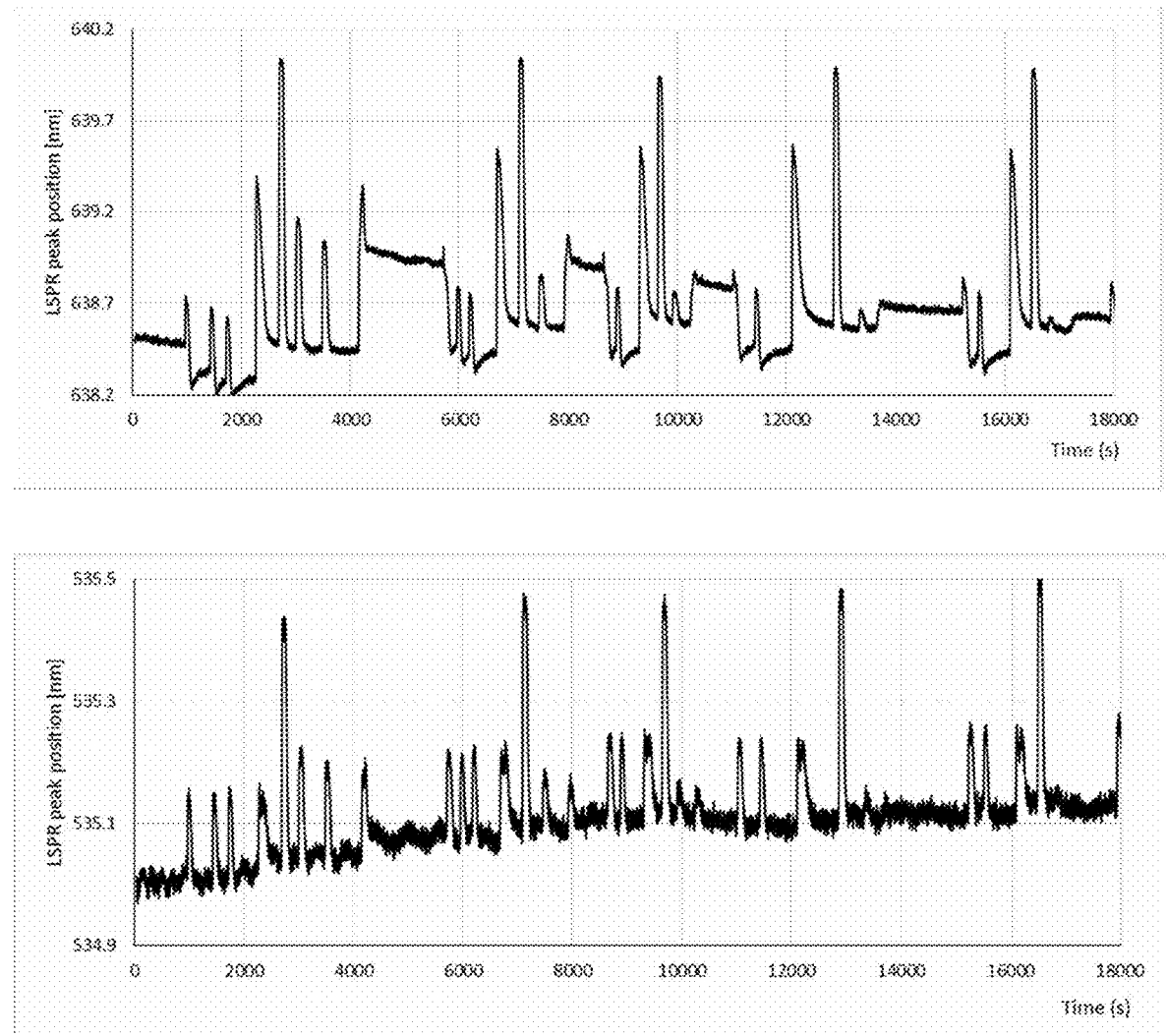
FIG. 34B are graphs showing the self-referencing sensor response over time for the functionalized and blocked particles.

FIG. 34 presents another example of experimental data obtained from a self-referencing sensor comprising two different types of nanoparticles immobilized onto a glass substrate. The two nanoparticle types included gold spheres with a diameter of 40 nm and gold NanoUrchins with a diameter of 90 nm, with optical properties of LSPR peak wavelengths around 530 nm and 630 nm respectively. Both nanoparticle types were immobilized onto the same area of the glass substrate, and produced two LSPR peaks at 535 nm and 638 nm as shown in FIG. 34A. The LSPR peaks were distinct with some spectral overlap, and could be individually tracked to monitor the LSPR sensing properties of each particle type. The 90 nm NanoUrchins were functionalized with a thiol-containing NTA capture molecule (functionalized particle) to act as the specific sensing particle. The 40 nm spheres were functionalized with a dithiolalkanearomatic-PEG3-OH blocking molecule (blocked particle). The experiment was carried out using an LSPR apparatus in transmission mode similar to that described in FIG. 25. As a running buffer, 1x HEPES buffered saline (HBS) at pH 7.4 with 0.005% Tween20 and 0.1% BSA was used. Polyhistidine tagged (His6) streptavidin was used as the analyte at a concentration of 1000 nM containing 3.5% glycerol to produce a non-specific bulk signal in addition to specific binding. The His6-streptavidin with glycerol underwent serial dilution with running buffer to produce additional concentrations at 500 nM, 250 nM, 125 nM and 62.5 nM. To measure the LSPR sensing response of the nanoparticles, both peak positions were simultaneously measured and recorded over time. First, the surface was primed with several exposures of imidazole (200 mM) and NiCl₂ (40 mM) for approximately 100 s each, before being exposed to solutions of glycerol (bulk) and 1000 nM His6-streptavidin+ 3.5% glycerol (Analyte+bulk) for the same amount of time. At least 600 s after the analyte+bulk exposure, imidazole was used 2-3 times to regenerate the NTA surface chemistry on the functionalized particle, followed by NiCl₂ exposure and glycerol solutions prior to the next lower concentration of analyte+bulk. This process was repeated for all analyte concentrations. The full sensor response of the functionalized particle and blocked particle is given in FIG. 34B. Upon analyte+bulk exposure, a prolonged shift in the LSPR peak position is observed with the functionalized particle whereas only a short temporary shift is observed with the blocked particle indicating that the blocked particle is not detecting specific binding but only the bulk shifts.

Figure 35A:
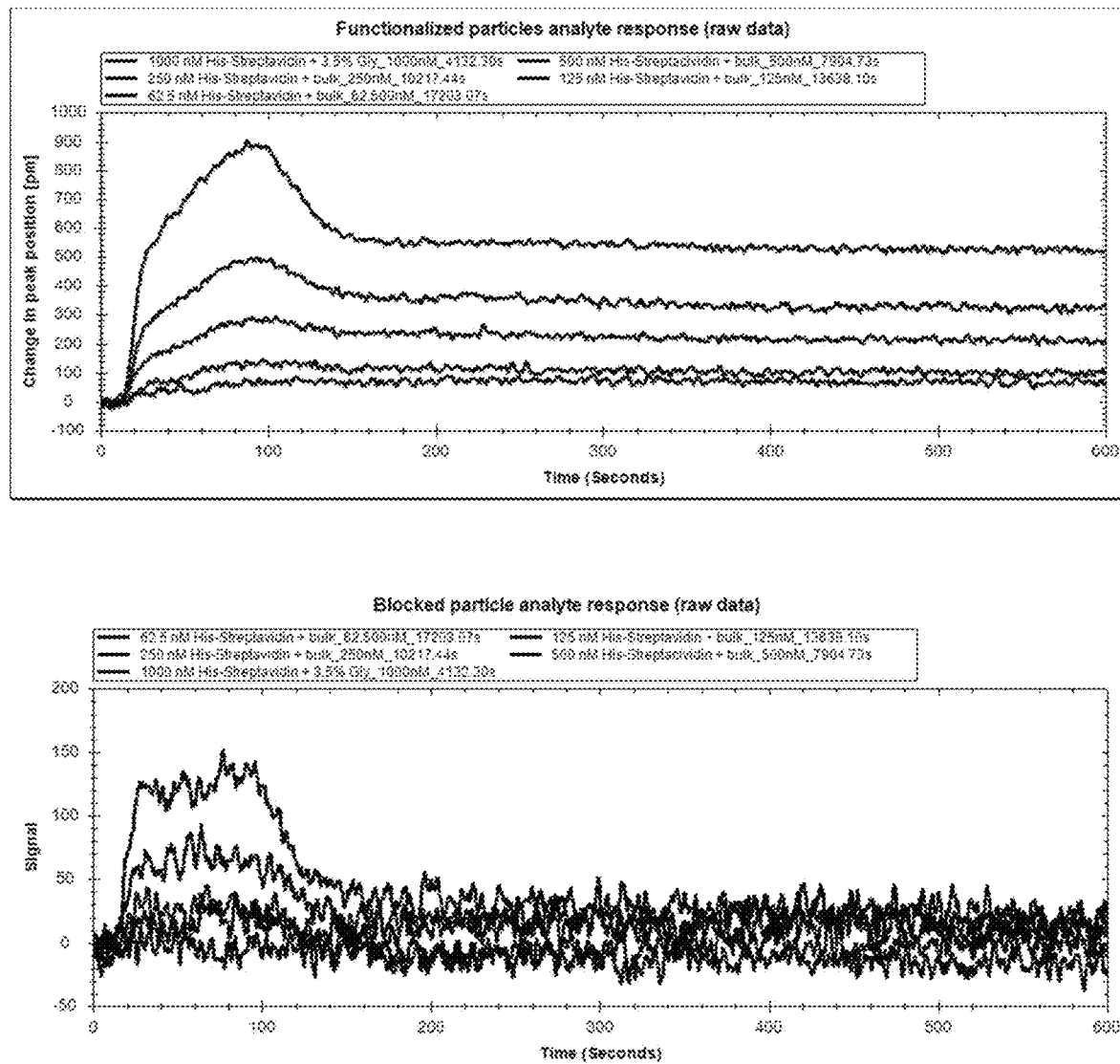
FIG. 35A are graphs showing the raw signals obtained from functionalized particles and blocked particles upon exposure to analyte with bulk background.
Figure 35B:
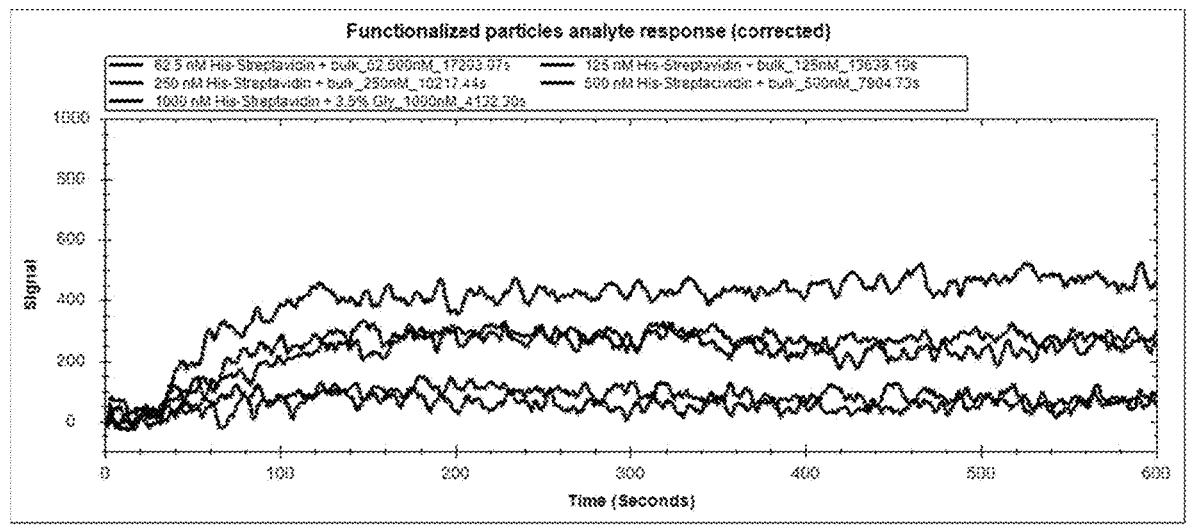
FIG. 35B is a graph showing the corrected binding responses with the bulk background removed.

FIG. 35 contains the experimental raw and corrected NTA-His6-streptavidin binding curves from the data presented in FIG. 34. FIG. 35A presents the raw signals obtained from the functionalized particles and the blocked particles upon analyte exposure. The binding curves from the functionalized particle contains an obvious bulk distortion (top graph), whereas no binding curves are seen with the blocked particle, as it only detected bulk effects acting as the reference signal (bottom graph). As the sensitivities of both particle types used were different, the reference signal was calibrated to that of the detection signal by normalizing the sensitivity of the blocked particle to that of the functionalized particle. To reduce the noise of the reference signal, a moving average with n=21 was implemented. Using the calibrated reference signal provided by the blocked nanoparticle, the bulk effects were able to be subtracted and effectively removed from the distorted signal. The corrected binding responses are shown in FIG. 35B.

Example 7: Self-Referencing Sensor Two-Nanoparticle System, One Particle Functionalized with Capture Molecule, the Other with Blocking Molecule (Streptavidin Detection with Different Nanoparticle Combination)

Figure 36A:
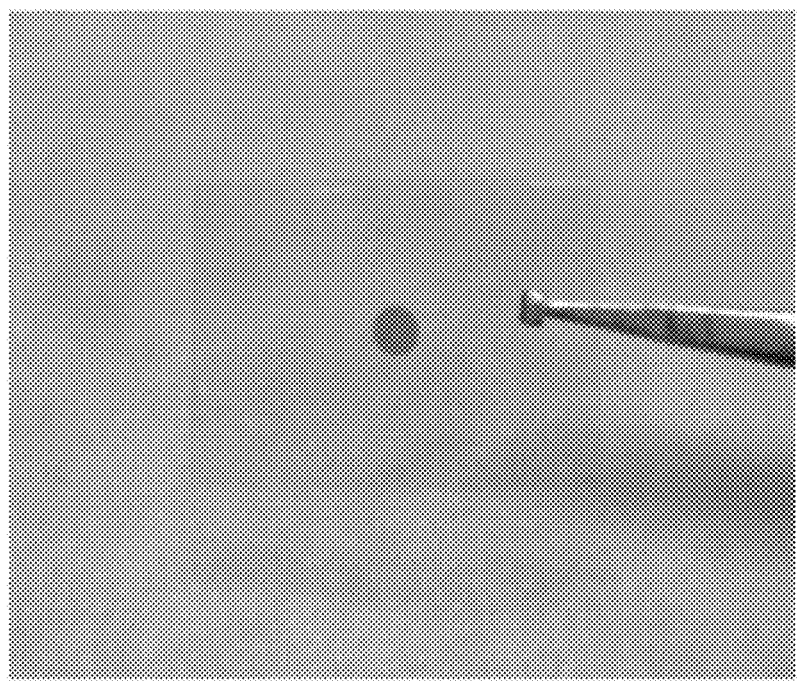
FIG. 36A is a photograph of a self-referencing sensor comprising two nanoparticle types immobilized onto the same area of a glass substrate.
Figure 36B:
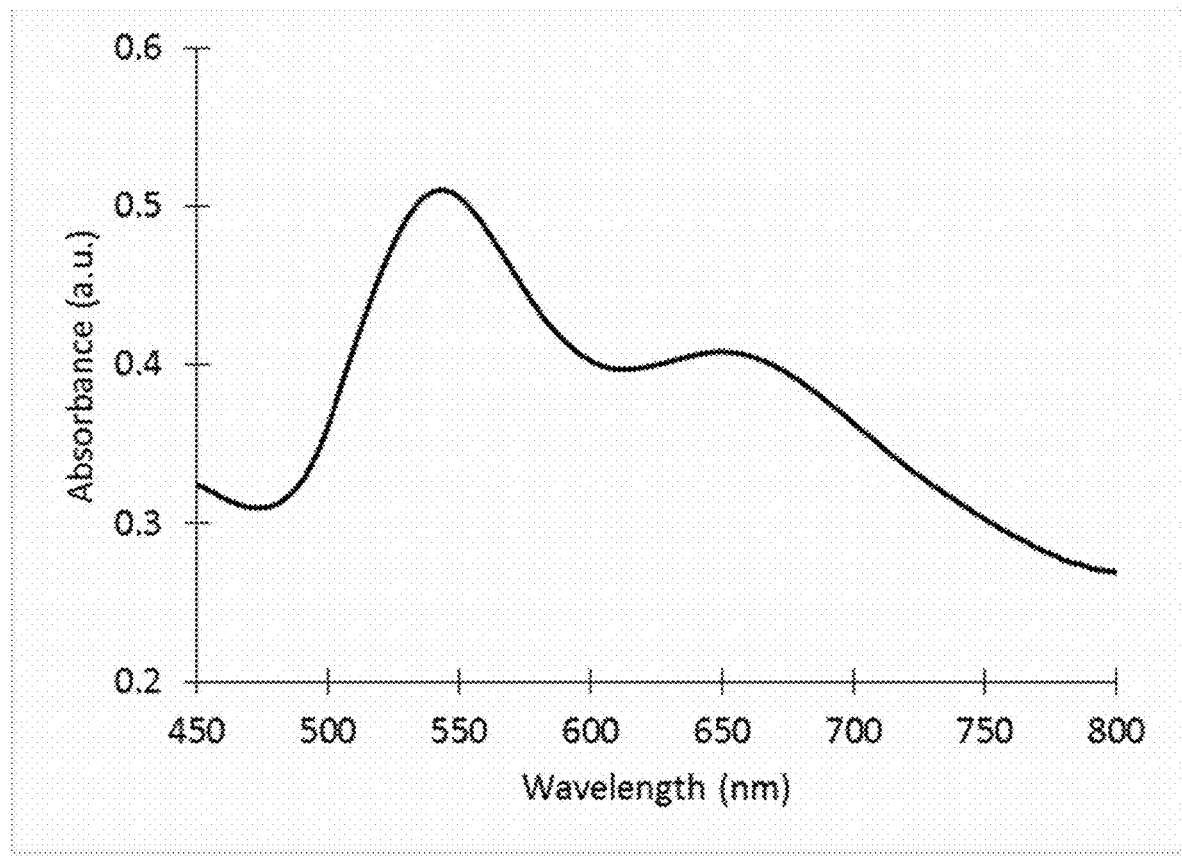
FIG. 36B is the absorbance spectrum of the self-referencing sensor.
Figure 36C:
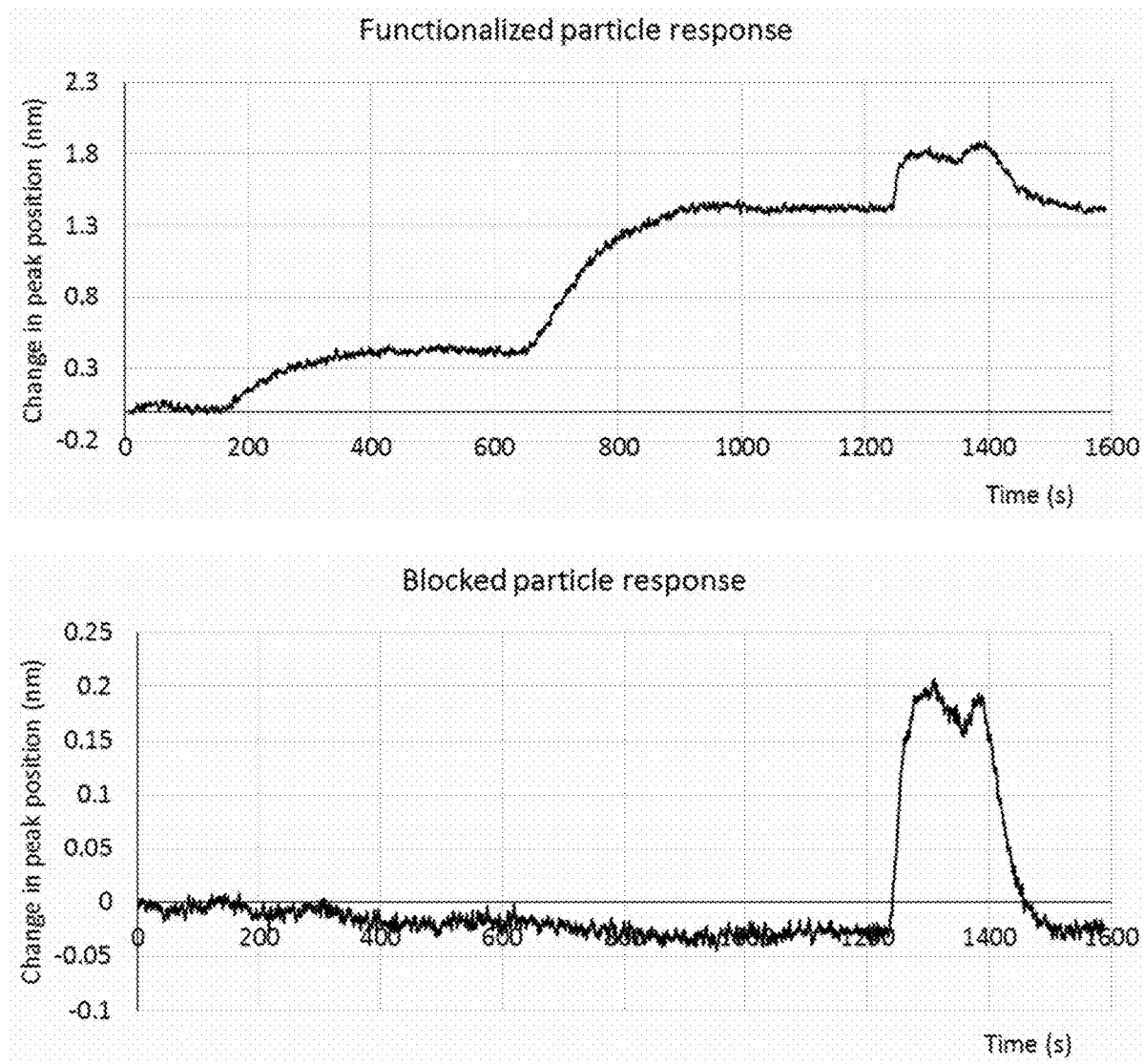
FIG. 36C are graphs showing the LSPR sensor response over time for both the functionalized and blocked nanoparticles.

FIG. 36 presents experimental data taken from a self-referencing sensor apparatus as described herein, using a sensor comprising a different combination of two nanoparticle types immobilized onto a glass substrate. The two nanoparticle types included gold spheres with a diameter of 80 nm and gold NanoUrchins with a diameter of 100 nm, with optical properties of LSPR peak wavelengths around 550 nm and 648 nm in solution respectively. Both nanoparticle types were immobilized onto the same area of the glass substrate as shown in FIG. 36A, and produced two LSPR peaks at 543 nm and 650 nm after functionalization as shown in FIG. 36B. The LSPR peaks were distinct and could be individually tracked to monitor the LSPR sensing properties of each particle type. The 100 nm NanoUrchins were functionalized with a thiol-containing Biotin capture molecule (functionalized particle) to act as the specific sensing particle. The 80 nm spheres were functionalized with a dithiolalkanearomatic-PEG3-OH blocking molecule (blocked particle). The experiment was carried out using an LSPR apparatus in transmission mode similar to that described in FIG. 25. As a running buffer, 1x phosphate buffered saline (PBS) at pH 7.4 with 0.05% Tween20 was used at a constant flow rate of 75 µL/min. Streptavidin diluted in running buffer was used as the analyte, and 25 mg/mL of sugar dissolved in distilled water was used to produce nonspecific bulk refractive index shifts. To measure the LSPR sensing response of the nanoparticles, both peak positions were simultaneously measured and recorded over time. First, streptavidin at a concentration of 11.1 nM was exposed to the surface for approximately 100 seconds, followed by introduction of 33.3 nM Streptavidin, then 25 mg/mL sugar to produce a bulk refractive index change for the same amount of time. FIG. 36C shows the responses of both nanoparticle types. Upon the introduction of just the sugar solution (bulk), a similar temporary signal change is seen for both nanoparticle types. When exposed to the streptavidin solutions, the response of the functionalized particle showed a permanent peak shift indicating streptavidin binding and detection. For the blocked particle, no response was observed upon introduction of streptavidin, indicating no binding or specific detection from this particle type. Therefore the blocked particle was able to provide a reference signal for only the non-specific interactions.

Figure 32A:
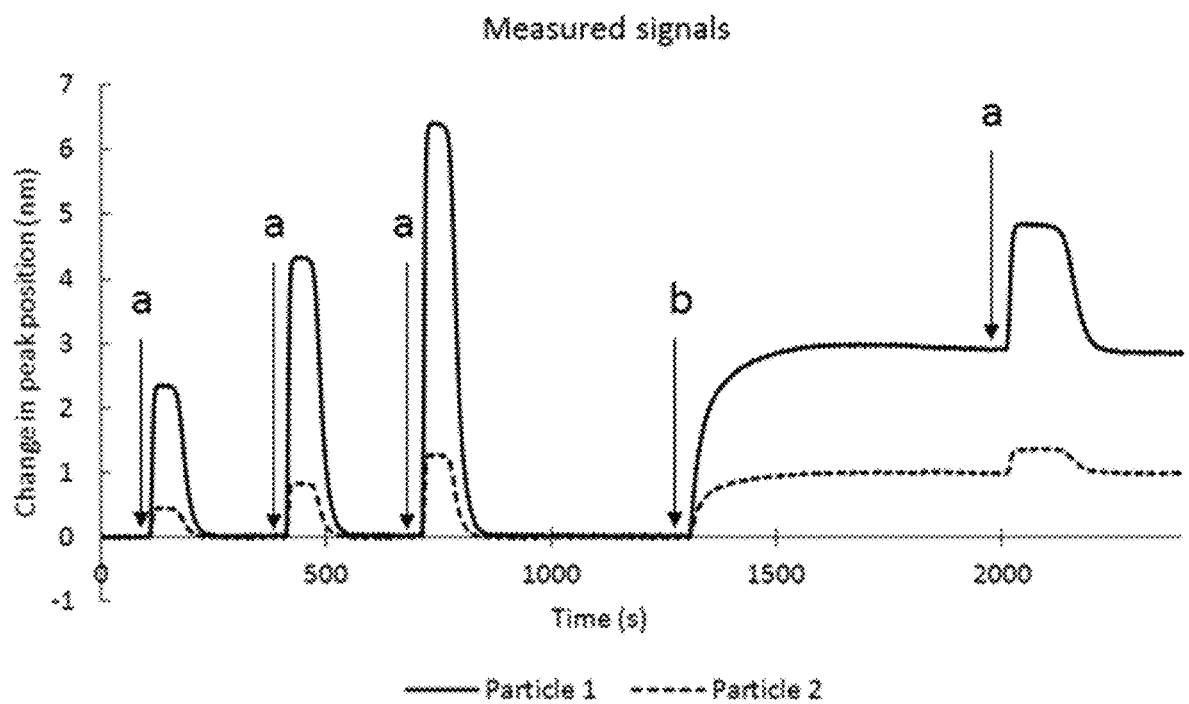
FIG. 32A and FIG. 32B are graphs showing experimental results of a two nanoparticle type self-referencing sensor system, with both particle types containing the same functionalization.
Figure 32B:
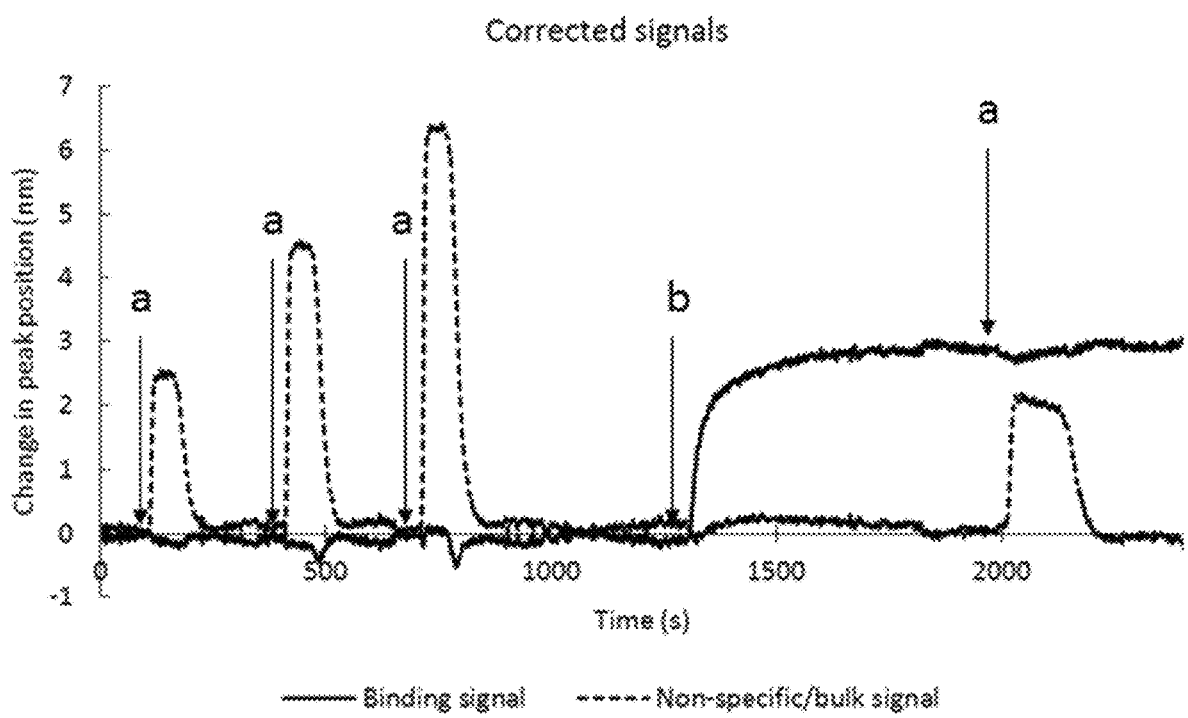

Example 8: Self-Referencing Sensor, Two-Nanoparticle System, Both Particles Functionalized with the Same Capture Molecule FIG. 32 presents experimental data taken from a self-referencing sensor apparatus composed of two nanoparticle types immobilized onto a glass substrate, both having the same functional surface. The two nanoparticle types included gold spheres with a diameter of 40 nm (particle 2) and gold NanoUrchins with a diameter of 90 nm (particle 1), with optical properties of LSPR peak wavelengths around 530 nm and 630 nm respectively. Both nanoparticle types were immobilized onto the same area of the glass substrate similar to that shown in FIG. 28A, and produced two LSPR peaks at 534 nm (particle 2) and 618 nm (particle 1) similar to that shown in FIG. 28B. The LSPR peaks were distinct with some spectral overlap, and could be individually tracked to monitor the LSPR sensing properties of each particle type. In this example, HS-PEG$_{2k}$-MeOH was used as the analyte at a concentration of 0.333 mM (a). As the thiol portion of the analyte binds directly to gold, both nanoparticle types were left as bare gold surfaces in place of additional functionalization with a capture molecule. To produce bulk refractive index shifts (b), solutions containing 8%, 15% or 22% glycerol (w/w in water) were used. The experiment was carried out using an LSPR apparatus in transmission mode similar to that described in FIG. 25 and water was used as the running buffer. To measure the LSPR sensing response of the nanoparticles, both peak positions were simultaneously measured and recorded over time. First, three glycerol solutions (8%, 15%, 22% respectively) were exposed to the surface for approximately 100 seconds (b), followed by introduction of the analyte (a), and a final injection of 8% glycerol for the same period of time. As seen in FIG. 32A, introduction of the glycerol solutions (a) produced temporary sensor responses while the analyte (b) produced a permanent binding shift of both LSPR signals. It is clear that the responses of each particle type are different. Using the characteristic equations of both nanoparticle types, the binding signal was able to be separated from the bulk signals. The resulting separated binding and bulk signals for particle 1 are shown in FIG. 32B.

Example 9: Self Referencing Sensor, Single-Nanoparticle System

Figure 33A:
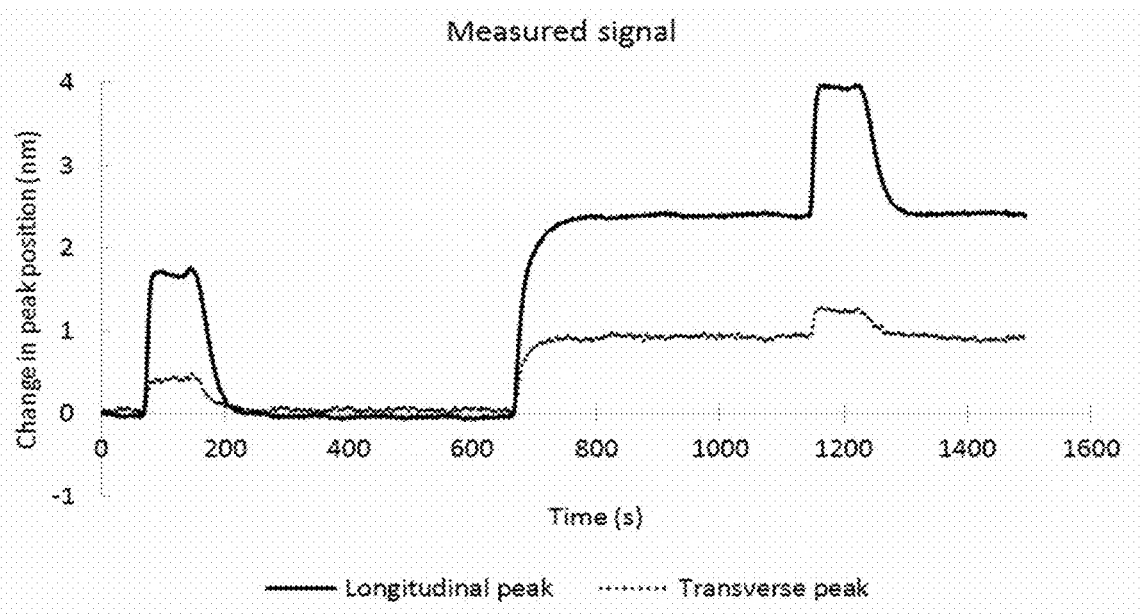
FIG. 33A and FIG. 33B are graphs showing experimental results of a single nanoparticle type self-referencing sensor system, producing two distinct LSPR peaks.
Figure 33B:
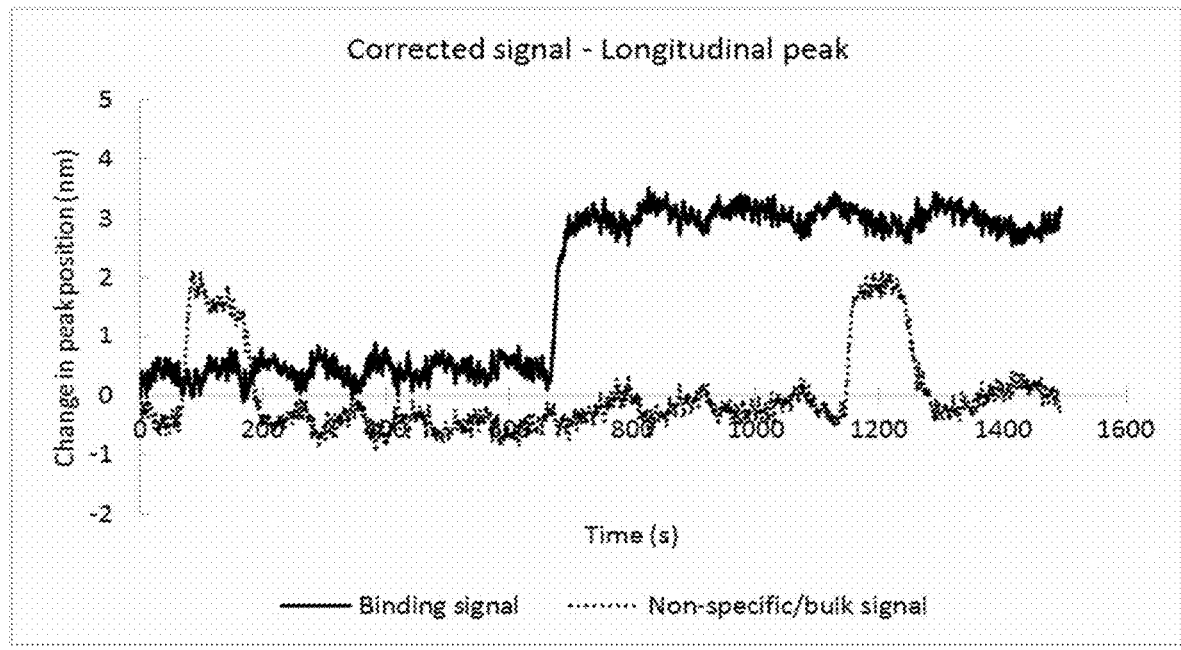

FIG. 33 contains experimental data taken from a self-referencing sensor composed of a single nanoparticle type. In this example, gold nanorods having dimensions of 40 nm×80 nm were used, with longitudinal and transverse LSPR peaks at 660 nm and 527 nm respectively. When immobilized onto a glass substrate, both the transverse and longitudinal signals produced two distinct LSPR peaks at 537 nm and 677 nm respectively, as shown in FIG. 27. The nanorods were functionalized with a thiol-containing biotin capture molecule. The experiment was carried out with a transmission-based self-referencing sensor apparatus described in FIG. 25. As a running buffer, 1×PBS at pH 7.4 with 0.05% Tween20 was used. Streptavidin at a concentration of 1 µM diluted in running buffer was used as the analyte, and 8% glycerol (w/w) was used to produce bulk refractive index shifts. To measure the LSPR sensing response of the nanoparticles, both peak positions were simultaneously measured and recorded over time. All solutions were exposed to the sensor surface for approximately 150 seconds. As shown in FIG. 33A, introduction of the glycerol solution (a) produced temporary sensor responses while the specific sensing molecule (b) produced a permanent binding shift of both LSPR peak positions. Both peaks showed different sensing responses. Using the characteristic equations governing the sensing abilities of both LSPR peaks, the binding signal was able to be distinguished from the bulk signals. The resulting separated signals as sensed from the longitudinal LSPR peak are shown in FIG. 33B.

Example 10: Solution-Phase Self-Referencing Sensor, Two-Nanoparticle System

Figure 37A:
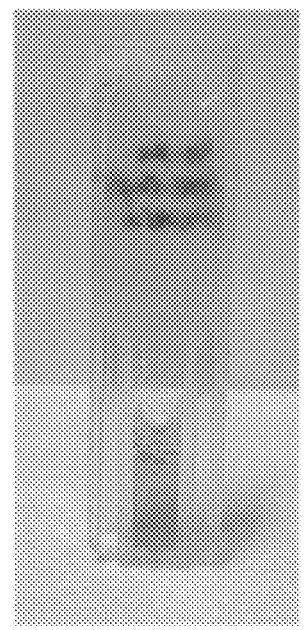
FIG. 37A is a photograph of a self-referencing sensor comprising two nanoparticle types present in solution.
Figure 37B:
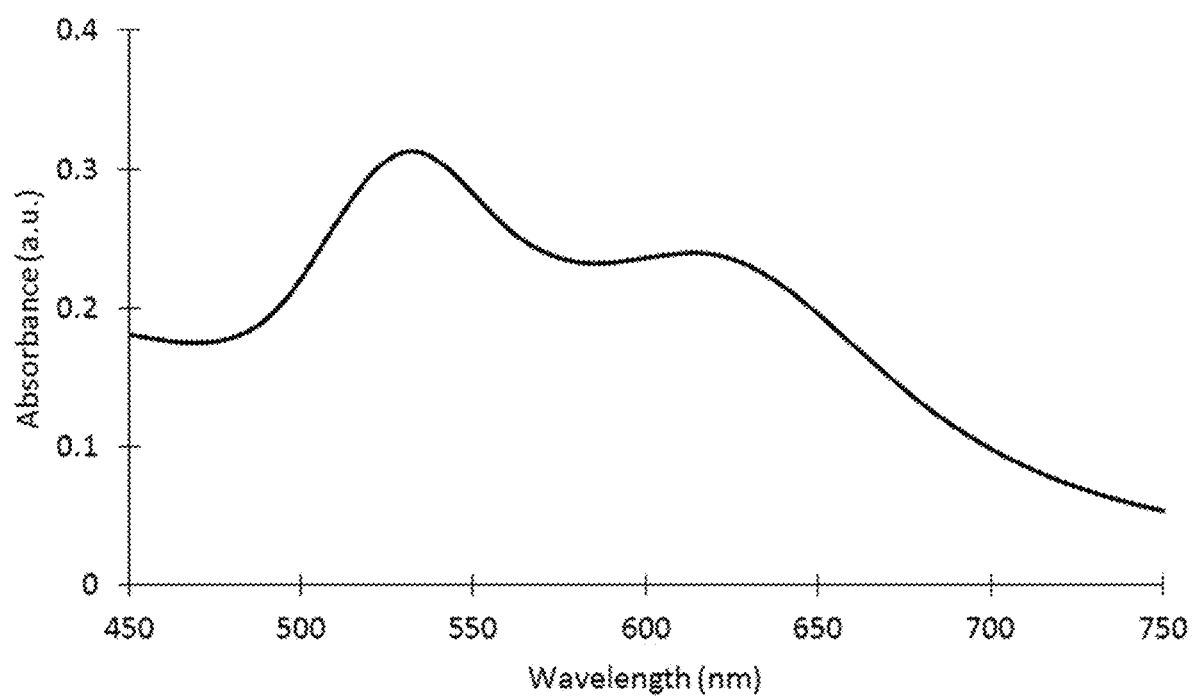
FIG. 37B is the absorbance spectrum of the self-referencing sensor.
Figure 37C:
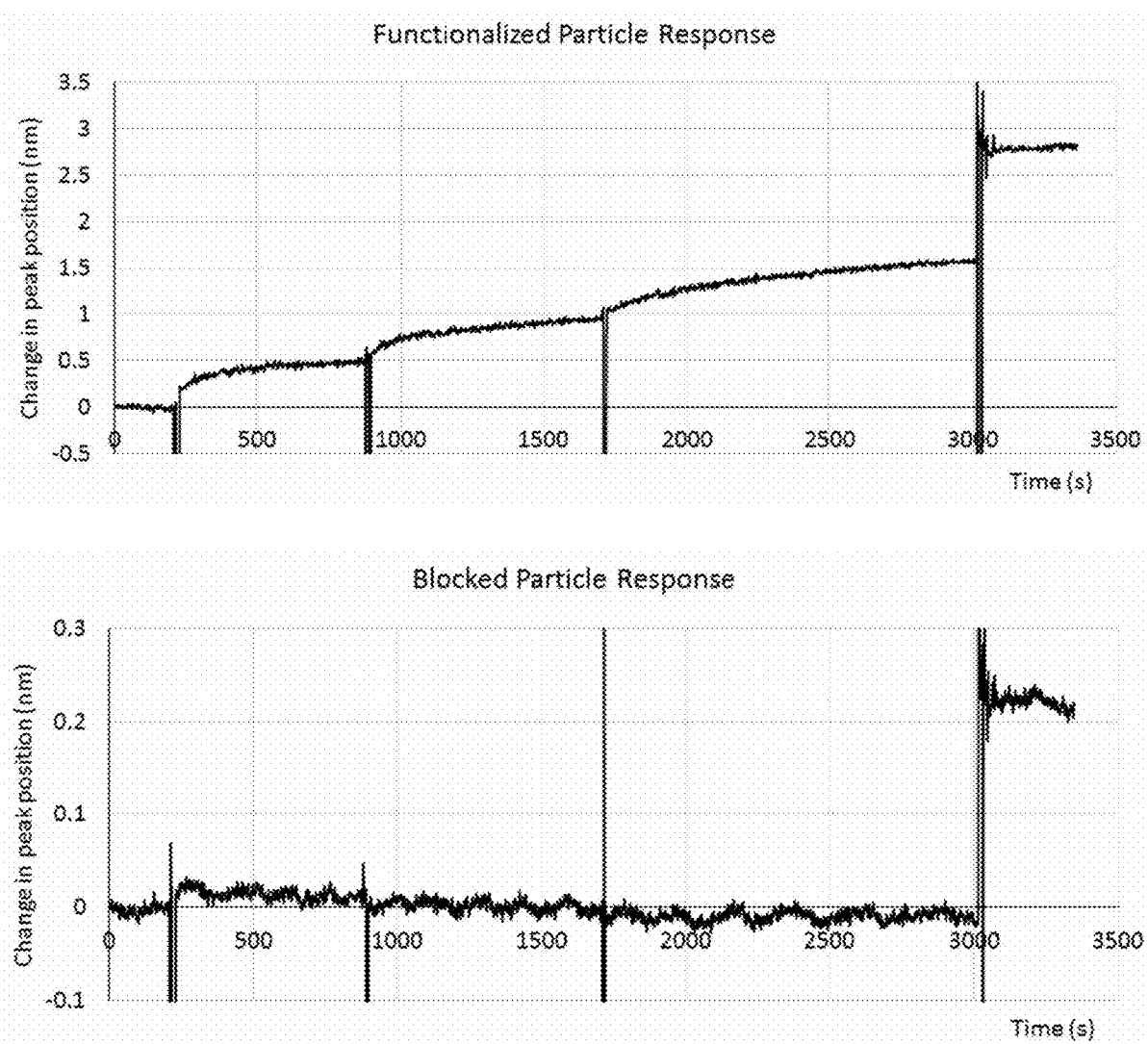
FIG. 37C are graphs showing the LSPR sensor response over time for both the functionalized and blocked nanoparticles.

FIG. 37 presents experimental data taken from a self-referencing sensor apparatus as described herein, using a solution-phase sensor comprising two nanoparticle types. The two nanoparticle types included gold spheres with a diameter of 40 nm and gold NanoUrchins with a diameter of 80 nm. The 40 nm spheres were functionalized with a methoxy-PEG5000-SH blocking molecule (blocked particle) and the 80 nm NanoUrchins were functionalized with streptavidin as a capture molecule (functionalized particle) with LSPR peak wavelengths around 530 nm and 620 nm, respectively. Both nanoparticle types were mixed in a solution of 0.01×PBS and placed into a semi-micro polystyrene cuvette as shown in FIG. 37A, and produced two LSPR peaks at 532 nm and 612 nm as shown in FIG. 37B. The LSPR peaks were distinct and could be individually tracked to monitor the LSPR sensing properties of each particle type. The experiment was carried out using an LSPR apparatus in transmission mode. Biotinylated anti-rabbit IgG (stock concentration 3 mg/mL) was used as the analyte, and a glycerol solution was used to produce nonspecific bulk refractive index shifts. To measure the LSPR sensing response of the nanoparticles, both peak positions were simultaneously measured and recorded over time. The response of both nanoparticles over time is shown in FIG. 37C. The anti-rabbit IgG was added to the sensor solution 2 µg at a time (a), with at least 10 minutes between additions. After the third addition of anti-rabbit IgG, 60% glycerol (w/w in H2O) was added to the sensor solution to produce a final concentration of 3% glycerol, creating a bulk refractive index shift (b). Immediately after each addition, the sensor solution was mixed by pipetting, causing brief interruption of the signal and producing large spikes on the response graphs, which can be ignored. Upon the introduction of the glycerol solution, a similar immediate signal change is seen for both nanoparticle types as it produced a non-specific bulk refractive index change. With addition of the anti-rabbit IgG, the response of the functionalized particle showed a peak shift indicating binding and detection. The peak shifted gradually over time due to effect of diffusion of the analyte, producing final LSPR peak shifts of approximately 500 µm. For the blocked particle, no response was observed upon introduction of anti-rabbit IgG, indicating no binding or specific detection from this particle type. Therefore the blocked particle was able to provide a reference signal for only the non-specific interactions.

Although the above has been described with reference to certain specific example embodiments, various modifications thereof will be apparent to those skilled in the art without departing from the scope of the claims appended hereto.

We claim:

1. An LSPR apparatus comprising:
   at least one self-referencing sensor for detection of an analyte binding signal and simultaneous detection of non-specific signals comprising one or more types of nanoparticles, wherein the one or more types of nanoparticles are configured to simultaneously emit at least two distinct LSPR signals comprising a first LSPR analyte signal and at least a second LSPR reference signal, wherein at least one nanoparticle type of the one or more types of nanoparticles includes a capture molecule to bind to an analyte resulting in the first LSPR analyte signal;
   a light source;
   a detector for simultaneous detection of the first LSPR analyte signal and the second LSPR reference signal in response to light from the light source interacting with the at least one self-referencing sensor; and
   a signal processor in operative communication with the detector to receive the first LSPR analyte signal and the second LSPR reference signal, calculate a difference in a resulting optical spectrum change between the first LSPR analyte signal and the second LSPR reference signal to distinguish the first LSPR analyte signal from non-specific signals comprising the second LSPR reference signal, and to select an output based on the difference in the resulting optical spectrum change between the first LSPR analyte signal and the second LSPR reference signal.

2. An LSPR apparatus according to claim 1 wherein the self-referencing sensor is substantially transparent and is disposed between the light source and apparatus such that the LSPR signal is detected in transmission mode.

3. The self-referencing sensor according to claim 1 wherein there is one type of nanoparticle configured to simultaneously emit at least two distinct LSPR signals.

4. The self-referencing sensor according to claim 1 wherein there are two or more types of nanoparticles and each type of nanoparticle has a distinct LSPR signal that can be distinguished from the LSPR signal of each other type of nanoparticle.

5. The self-referencing sensor according to claim 4 wherein one of the nanoparticle types is functionalized with a capture molecule.

6. The self-referencing sensor according to claim 4 wherein each nanoparticle type is functionalized with a capture molecule.

7. The self-referencing sensor according to claim 6 wherein each nanoparticle type is functionalized with the same capture molecule.

8. A self-referencing sensor according to claim 4 comprising three or more nanoparticle types, wherein at least one nanoparticle type is not functionalized or is functionalized with a blocking molecule and wherein each remaining nanoparticle type is functionalized with a different capture molecule.

9. The self-referencing sensor according to claim 1 wherein the nanoparticles are immobilized on one or more substrates.

10. The self-referencing sensor according to claim 1 wherein the nanoparticles are in solution.

11. The self-referencing sensor according to claim 1 wherein the nanoparticles are 1 to 1000 nm in at least one dimension.

12. The self-referencing sensor according to claim 1 wherein the nanoparticles are a metal, metal coating a second metal or a metal coating a non-metal particle and wherein the metal is gold, silver, platinum, palladium or copper.

13. The self-referencing sensor according to claim 1 wherein the nanoparticles are gold.

14. The self-referencing sensor according to claim 1 wherein the nanoparticles are spheres, rods, urchins, stars, rice, plates, decahedrons, hexagons, prisms, shells, platelets, triangles, cubes, cages, bipyramids or a mixture thereof.

15. The self-referencing sensor according to claim 4 wherein at least one of the nanoparticles types is functionalized with a blocking molecule which blocks binding of an analyte.

16. The self-referencing sensor according to claim 1 wherein the capture molecule is the surface of the nanoparticle.

17. The self-referencing sensor according to claim 1 wherein the capture molecule is an aptamer, antibody, nucleic acid, protein, small molecule or polymer.

18. The self-referencing sensor according to claim 9 wherein the nanoparticles are immobilized onto a single substrate.

19. The self-referencing sensor according to claim 18 wherein the self-referencing sensor has more than one nanoparticle type and the nanoparticle types are immobilized onto the same or different regions of the substrate.

* * * * *